United States Patent [19]

Hashimoto et al.

[11] Patent Number: 4,640,915
[45] Date of Patent: Feb. 3, 1987

[54] 1-AZABICYCLO[3.2.0]HEPT-2-ENE-2-CARBOXYLIC ACID DERIVATIVES

[75] Inventors: Masashi Hashimoto, Takarazuka; Matsuhiko Aratani, Daito; Kozo Sawada, Toyonaka, all of Japan

[73] Assignee: Fujisawa Pharmaceutical Co., Ltd., Osaka, Japan

[21] Appl. No.: 476,860

[22] Filed: Mar. 18, 1983

[30] Foreign Application Priority Data

Mar. 29, 1982 [GB] United Kingdom ................. 8209156
Oct. 18, 1982 [GB] United Kingdom ................. 8229675

[51] Int. Cl.[4] .................... C07D 487/04; A61K 31/40
[52] U.S. Cl. .................................. 514/210; 540/200; 540/300; 540/350
[58] Field of Search ................. 260/245.2 T; 424/270, 424/271; 514/210

[56] References Cited

U.S. PATENT DOCUMENTS

| 4,347,181 | 8/1982 | Small | 260/245.2 T |
| 4,347,367 | 8/1982 | Christensen et al. | 260/245.2 T |
| 4,383,946 | 5/1983 | Christensen et al. | 260/245.2 T |
| 4,435,412 | 3/1984 | Girijavallabhan et al. | 260/245.2 R |
| 4,477,662 | 10/1984 | Corbett et al. | 260/245.2 T |

FOREIGN PATENT DOCUMENTS

| 8497 | 2/1980 | European Pat. Off. . |
| 55-139380 | 10/1980 | Japan . |
| 56-156282 | 12/1981 | Japan . |
| 2071099 | 9/1981 | United Kingdom . |

Primary Examiner—Nicholas S. Rizzo
Attorney, Agent, or Firm—Oblon, Fisher, Spivak, McClelland & Maier

[57] ABSTRACT

Compounds of the formula [I]

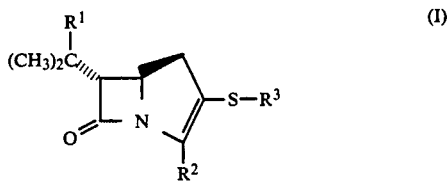

in which $R^1$ is hydroxy, a protected hydroxy or lower alkoxy group, $R^2$ is carboxy or an easily eliminable esterified carboxy group and $R^3$ is pyridyl, and pharmaceutically acceptable salts thereof, having antimicrobial and $\beta$-lactamase inhibiting properties, and pharmaceutical compositions containing the same.

4 Claims, No Drawings

1-AZABICYCLO[3.2.0]HEPT-2-ENE-2-CARBOXYLIC ACID DERIVATIVES

The present invention relates to novel 1-azabicyclo[3.2.0]hept-2-ene-2-carboxylic acid derivatives and pharmaceutically acceptable salts thereof.

More particularly, it relates to novel 1-azabicyclo[3.2.0]hept-2-ene-2-carboxylic acid derivatives and pharmaceutically acceptable salts thereof, which have antimicrobial activity, to processes for the preparation thereof, to a pharmaceutical composition comprising the same, and to a method of using the same therapeutically in the treatment of infectious diseases in human being or animals.

Accordingly, one object of the present invention is to provide novel 1-azabicyclo[3.2.0]hept-2-ene-2-carboxylic acid derivatives and pharmaceutically acceptable salts thereof, which are highly active against a number of pathogenic microorganisms and are useful as antimicrobial agents.

Another object of the present invention is to provide processes for the preparation of novel 1-azabicyclo[3.2.0]hept-2-ene-2-carboxylic acid derivatives and salts thereof.

A further object of the present invention is to provide a pharmaceutical composition comprising, as active ingredients, said 1-azabicyclo[3.2.0]hept-2-ene-2-carboxylic acid derivatives and pharmaceutically acceptable salts thereof.

Still further object of the present invention is to provide a method of using said 1-azabicyclo[3.2.0]hept-2-ene-2-carboxylic acid derivatives and pharmaceutically acceptable salts thereof in the treatment of infectious diseases by pathogenic microorganisms in human being or animals.

The object 1-azabicyclo[3.2.0]hept-2-ene-2-carboxylic acid derivatives are novel and can be represented by the following general formula:

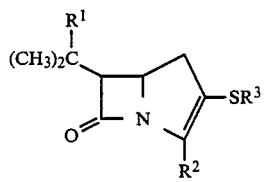

(I)

in which
R$^1$ is hydroxy, a protected hydroxy group or lower alkoxy,
R$^2$ is carboxy or a protected carboxy group and
R$^3$ is aryl having suitable substituent(s), pyridyl which may have suitable substituent(s) or heterocyclic group containing 3 to 5 hetero atoms which may have suitable substituent(s).

In the object compounds (I) and the starting compound (II) mentioned below, it is to be understood that there may be one or more stereoisomeric pair(s) such as optical isomers due to asymmetric carbon atom at the fifth and sixth positions of the 1-azabicyclo[3.2.0]hept-2-ene ring, and such isomers are also included within the scope of the present invention.

Suitable pharmaceutically acceptable salts of the object compounds (I) are conventional non-toxic salts and may include a salt with a base such as an inorganic base salt, for example, an alkali metal salt (e.g. sodium salt, potassium salt, etc.), an alkaline earth metal salt (e.g. calcium salt, magnesium salt, etc.), an ammonium salt, an organic base salt, for example, an organic amine salt (e.g. triethylamine salt, pyridine salt, picoline salt, ethanolamine salt, triethanolamine salt, dicyclohexylamine salt, N,N'-dibenzylethylenediamine salt, etc.); a salt with an acid such as an inorganic acid addition salt (e.g. hydrochloride, hydrobromide, sulfate, phosphate, etc.), an organic acid addition salt (e.g. formate, acetate, trifluoroacetate, maleate, tartarate, methanesulfonate, benzenesulfonate, toluenesulfonate, etc.); a salt with a basic or acidic amino acid (e.g. arginine, aspartic acid, glutamic acid, etc.); an intermolecular or intramolecular quaternary salt, and the like. The said intermolecular quaternary salt can be formed in case that the heterocyclic group in R$^3$ in the compounds (I) contains nitrogen atom(s) (e.g. pyridyl, etc.), and suitable intermolecular quaternary salt may include 1-lower alkylpyridinium lower alkylsulfate (e.g. 1-methylpyridinium methylsulfate, 1-ethylpyridinium ethylsulfate, etc.), 1-lower alkylpyridinium halide (e.g. 1-methylpyridinium iodide, etc.) and the like. The said intramolecular salt can be formed in case that heterocyclic group in R$^3$ in the compounds (I) contains nitrogen atom(s) (e.g. pyridyl etc.) or lower alkanimidoylamino B lower)alkyl as the substituent of said heterocyclic group, and R$^2$ is carboxy, and suitable intramolecular salt may include 1-lower alkylpyridinium carboxylate (e.g. 1-methylpyridinium carboxylate, 1-ethylpyridinium carboxylate, 1-propylpyridinium carboxylate, 1-isopropylpyridinium carboxylate, 1-butylpyridinium carboxylate, etc.); and the like.

According to the present invention, the object compounds (I) and the pharmaceutically acceptable salts thereof can be prepared by the processes as illustrated by the following reaction schemes.

(1) Process 1:

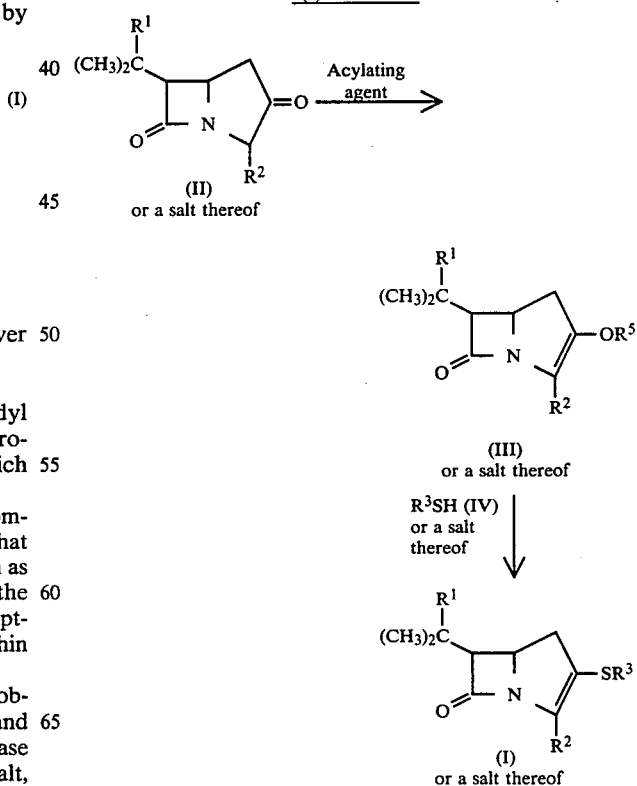

-continued (2) Process 2:

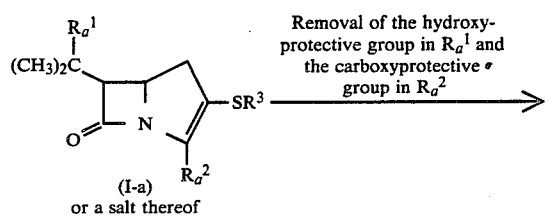

Removal of the hydroxy-protective group in $R_a^1$ and the carboxyprotective group in $R_a^2$

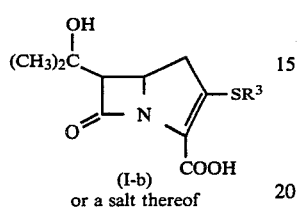

(3) Process 3:

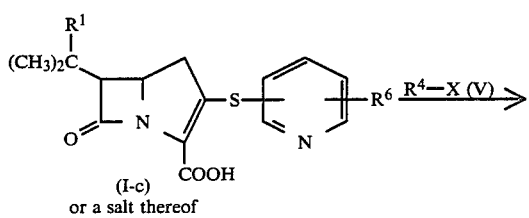

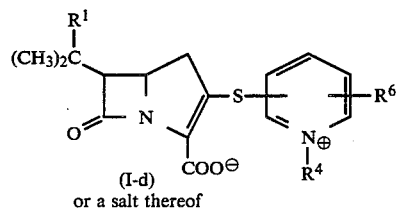

in which
R$^1$, R$^2$ and R$^3$ are each as defined above,
$R_a^1$ is a protected hydroxy group,
$R_a^2$ is a protected carboxy group,
R$^4$ is lower alkyl,
R$^5$ is acyl,
R$^6$ is hydrogen or amino, and
X is an acid residue.

The starting compound (II) used in Process 1 is new and can be prepared, for example, by the following methods.

(A) Method A:

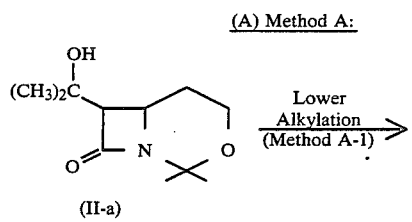 Lower Alkylation (Method A-1)

-continued (A) Method A:

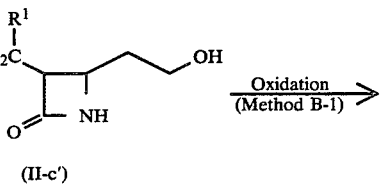

Hydrolysis (Method A-2)

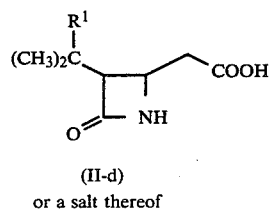

in which $R_b^1$ is lower alkoxy.

(B) Method B:

Oxidation (Method B-1)

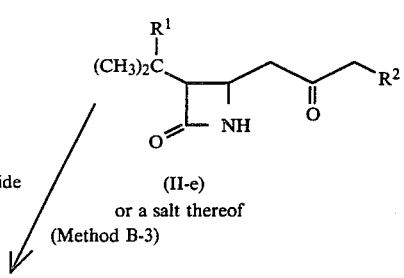

Malonic Acid or its derivative or a salt thereof (Method B-2)

Acid Azide (Method B-3)

(B) Method B:

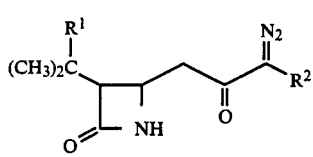

(II-f)
or a salt thereof

↓ Cyclization
(Method B-4)

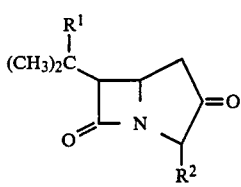

(II)
or a salt thereof in which R¹ and R² are each as defined above.

(C) Method C:

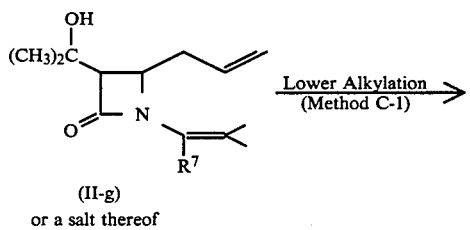

(II-g)
or a salt thereof

→ Lower Alkylation
(Method C-1)

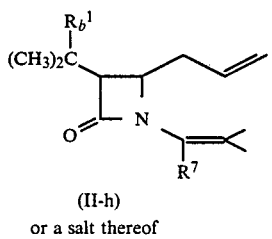

(II-h)
or a salt thereof

↓ (i) Ozonolysis
(ii) Degradation of Ozonide
(iii) Introduction of the formyl-protective group
(iv) Solvolysis
(Method C-2)

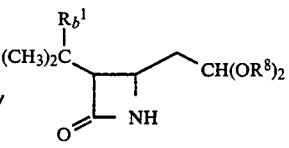

(II-i)

Hydrolysis ↙ (Method C-3)

(C) Method C:

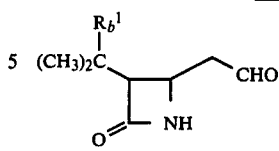

(II-j)

↓ Oxidation
(Method C-4)

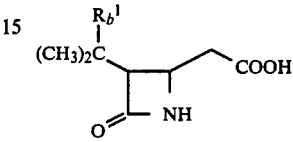

(II-k)
or a salt thereof in which
R⁷ is carboxy or a protected carboxy group,
R⁸ is lower alkyl, and
$R_b^1$ is as defined above.

Among the above starting compound (II), the compound represented by the following formula is especially a useful key intermediate for preparing various 1-azabicyclo[3.2.0]hept-2-ene-2-carboxylic acid derivatives including the object compounds of the present invention.

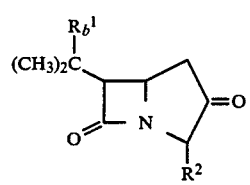

(II')
or a salt thereof in which $R_b^1$ and R² are each as defined above.

In the above and subsequent descriptions of the present specification, suitable examples and illustrations of the various definitions which the present invention include within the scope thereof are explained in details as follows.

The term "lower" is intended to mean 1 to 6 carbon atoms, unless otherwise indicated.

Suitable "a protected hydroxy group" may include a hydroxy group substituted by a conventional hydroxy-protective group, which is commonly used in β-lactam compounds such as thienamycin derivatives or its analogues, for example, acyl as mentioned below, ar(lower-)alkyl such as mono- or di- or triphenyl(lower)alkyl (e.g. benzyl, benzhydryl, trityl, etc.), etc., trisubstituted silyl such as tri(lower)alkylsilyl (e.g. trimethylsilyl, triethylsilyl, isopropyldimethylsilyl, tert-butyl-dimethylsilyl, diisopropylmethylsilyl, etc.), triarylsilyl (e.g. triphenylsilyl, etc.), triar(lower)alkylsilyl (e.g. tribenzylsilyl, etc.), etc., and the like.

Suitable "acyl" may include an aliphatic acyl, an aromatic acyl, a heterocyclic acyl and an aliphatic acyl substituted with aromatic or heterocyclic group(s) derived from carboxylic, carbonic, sulfonic, phosphinic and phosphoric acids.

The aliphatic acyl may include saturated or unsaturated, acyclic or cyclic ones, such as lower alkanoyl (e.g. formyl, acetyl, propionyl, butyryl, isobutyryl, valeryl, isovaleryl, pivaloyl, hexanoyl, etc.), lower alkanesulfonyl (e.g. mesyl, ethanesulfonyl, propanesulfonyl, etc.), lower alkoxycarbonyl (e.g. methoxycarbonyl, ethoxycarbonyl, propoxycarbonyl, butoxycarbonyl, tert-butoxycarbonyl, etc.), lower alkenoyl (e.g. acryloyl, methacryloyl, crotonoyl, etc.), ($C_3$–$C_7$)-cycloalkanecarbonyl (e.g. cyclohexanecarbonyl, etc.), tri(lower)alkylsilyl(lower)alkoxycarbonyl (e.g. 2-trimethylsilylethoxycarbonyl, etc.), di(lower)alkylphosphono (e.g. dimethylphosphono, diethylphosphono, etc.), and the like.

The aromatic acyl may include aroyl (e.g. benzoyl, toluoyl, xyloyl, etc.), arenesulfonyl (e.g. benzenesulfonyl, tosyl, etc.), diarylphosphinoyl (e.g. diphenylphosphinoyl, etc.), diarylphosphono (e.g. diphenylphosphono, ditolylphosphono, dinaphthylphosphono, etc.), and the like.

The heterocyclic aryl may include heterocyclic-carbonyl (e.g. furoyl, thenoyl, nicotinoyl, isonicotinoyl, thiazolylcarbonyl, thiadiazolylcarbonyl, tetrazolylcarbonyl, etc.), and the like.

The aliphatic acyl substituted with aromatic group(s) may include ar(lower)alkanoyl such as phenyl(lower)alkanoyl (e.g. phenylacetyl, phenylpropionyl, phenylhexanoyl, etc.), ar(lower)alkoxycarbonyl such as phenyl(lower)alkoxycarbonyl (e.g. benzyloxycarbonyl, phenethyloxycarbonyl, etc.), phenoxy(lower)alkanoyl (e.g. phenoxyacetyl, phenoxypropionyl, etc.), and the like.

The aliphatic acyl substituted with heterocyclic group(s) may include thienylacetyl, imidazolylacetyl, furylacetyl, tetrazolylacetyl, thiazolylacetyl, thiadiazolylacetyl, thienylpropionyl, thiadiazolylpropionyl, and the like.

These acyl groups may be further substituted with one or more suitable substituents such as lower alkyl (e.g. methyl, ethyl, propyl, isopropyl, butyl, pentyl, hexyl, etc.), halogen (e.g. chlorine, bromine, iodine, fluorine), lower alkoxy (e.g. methoxy, ethoxy, propoxy, isopropoxy, butoxy, pentyloxy, hexyloxy, etc.), lower alkylthio (e.g. methylthio, ethylthio, propylthio, isopropylthio, butylthio, pentylthio, hexylthio, etc.), nitro and the like, and preferable acyl having such substituent(s) may be mono (or di or tri)halo(lower)alkanoyl (e.g. chloroacetyl, bromoacetyl, dichloroacetyl, trifluoroacetyl, etc.), mono (or di tri)halo(lower)alkoxycarbonyl (e.g. chloromethoxycarbonyl, dichloromethoxycarbonyl, 2,2,2-tri-chloroethoxycarbonyl, etc.), nitro (or halo or lower alkoxy)phenyl(lower)alkoxycarbonyl (e.g. nitrobenzyloxycarbonyl, chlorobenzyloxycarbonyl, methoxybenzyloxycarbonyl, etc.), and the like.

More preferred example of the protected hydroxy group thus defined may be mono- or di- or tri-phenyl(lower)alkoxycarbonyloxy which may have nitro, and the most preferred one may be 4-nitrobenzyloxycarbonyloxy.

Suitable "lower alkoxy" may include straight or branched one such as methoxy, ethoxy, propoxy, isopropoxy, butoxy, isobutoxy, pentyloxy, isopentyloxy, hexyloxy, and the like.

Suitable "a protected carboxy group" may include an esterified carboxy group which is commonly used in β-lactam compounds such as penicillin and cephalosporin compounds at their 3rd and 4th positions thereof.

Suitable "ester moiety" in "esterified carboxy group" may include lower alkyl ester (e.g. methyl ester, ethyl ester, propyl ester, isopropyl ester, butyl ester, isobutyl ester, t-butyl ester, pentyl ester, tert-pentyl ester, hexyl ester, etc.), lower alkenyl ester (e.g. vinyl ester, allyl ester, etc.), lower alkynyl ester (e.g. ethynyl ester, propynyl ester, etc.), lower alkoxy(lower)alkyl ester (e.g. methoxymethyl ester, ethoxymethyl ester, isopropoxymethyl ester, 1-methoxyethyl ester, 1-ethoxyethyl ester, etc.), lower alkylthio(lower)alkyl ester (e.g. methylthiomethyl ester, ethylthiomethyl ester, ethylthioethyl ester isopropylthiomethyl ester, etc.), amino- and carboxy-substituted-lower alkyl ester (e.g. 2-amino-2-carboxyethyl ester, 3-amino-3-carboxypropyl ester, etc.), protected amino- and protected carboxy-substituted-lower alkyl ester such as lower alkoxycarbonylamino- and mono(or di or tri)phenyl(lower)alkoxycarbonyl-substituted-lower alkyl ester (e.g. 2-tert-butoxycarbonylamino-2-benzhydryloxycarbonylethyl ester, 3-tert-butoxycarbonylamino-3-benzhydryloxycarbonylpropyl ester, etc.), mono(or di or tri)halo(lower)alkyl ester (e.g. 2-iodoethyl ester, 2,2,2-trichloroethyl ester, etc.), lower alkanoyloxy(lower)alkyl ester (e.g. acetoxymethyl ester, propionyloxymethyl ester, butyryloxymethyl ester, isobutyryloxymethyl ester, valeryloxymethyl ester, pivaloyloxymethyl ester, hexanoyloxymethyl ester, 2-acetoxyethyl ester, 2-propionyloxyethyl ester, 1-acetoxypropyl ester, etc.), lower alkanesulfonyl(lower)alkyl ester (e.g. mesylmethyl ester, 2-mesylethyl ester, etc.), ar(lower)alkyl ester which may have one or more substituent(s) such as mono(or di or tri)phenyl(lower)alkyl ester which may have one or more suitable substituent(s) (e.g. benzyl ester, 4-methoxybenzyl ester, 4-nitrobenzyl ester, phenethyl ester, benzhydryl ester, trityl ester, bis(methoxyphenyl)methyl ester, 3,4-dimethoxybenzyl ester, 4-hydroxy-3,5-di-t-butylbenzyl ester, etc.), aryl ester which may have one or more suitable substituents (e.g. phenyl esters, tolyl ester, t-butylphenyl ester, xylyl ester, mesityl ester, cumenyl ester, salicyl ester, etc.), heterocyclic ester (e.g. phthalidyl ester, etc.), trisubstituted silyl ester (e.g. trimethylsilyl ester, triethylsilyl ester, tert-butyl-dimethylsilyl ester, isopropyl-dimethylsilyl ester, phenyl-dimethylsilyl ester, etc.), and the like.

More preferred example of the protected carboxy group thus defined may be mono- or di- or tri-phenyl(lower)alkoxycarbonyl which may have nitro, and the most preferred one may be 4-nitrobenzyloxycarbonyl.

Suitable "aryl having suitable substituent(s)" may include phenyl, tolyl, xylyl, cumenyl, and the like, which have one or more suitable substituent(s) such as amino, nitro, halogen (e.g. fluorine, chlorine, bromine, iodine, etc.), lower alkoxy as exemplified above, carboxy, a protected carboxy group as exemplified above, hydroxy, and the like.

More preferred example of "aryl having suitable substituent(s)" thus defined may be aminoaryl such as aminophenyl (e.g. 2-aminophenyl, etc.).

Suitable "pyridyl which may have suitable substituent(s)" may include 2-pyridyl, 3-pyridyl, 4-pyridyl, and the like, which may have one or more suitable substituent(s) such as amino, nitro, halogen (e.g. fluorine, chlorine, bromine, iodine, etc.), lower alkoxy as exemplified above, carboxy, a protected carboxy group as exemplified above, hydroxy, and the like.

More preferred example of "pyridyl which may have suitable substituent(s)" thus defined may be pyridyl which may have amino, and the most preferred one may be 2-pyridyl, 3-pyridyl, 4-pyridyl or aminopyridyl (e.g. 3-aminopyridin-4-yl, etc.).

Suitable "heterocyclic group containing 3 to 5 hetero atoms" in the definition of "heterocyclic group containing 3 to 5 hetero atoms which may have suitable substituent(s)" may include saturated or unsaturated, monocyclic or polycyclic heterocyclic group containing 3 to 5 hetero-atoms such as an oxygen, sulfur, nitrogen atom, and the like. And especially preferable heterocyclic group may be heterocyclic group such as:

unsaturated 3 to 8-membered (more preferably 5 or 6-membered)heteromonocyclic group containing 3 to 4 nitrogen atoms, for example, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;

unsaturated 3 to 8-membered (more preferably 5 or 6-membered)heteromonocyclic group containing 1 to 2 oxygen atom(s) and 2 to 3 nitrogen atoms, for example, oxadiazolyl (e.g. 1,2,4-oxadiazolyl, 1,3,4-oxadiazolyl, 1,2,5-oxadiazolyl, etc.), etc.;

unsaturated 3 to 8-membered (more preferably 5 or 6-membered)heterocyclic group containing 1 to 2 sulfur atom(s) and 2 to 3 nitrogen atoms, for example, thiadiazolyl (e.g. 1,2,3-thiadiazolyl, 1,2,4-thiadiazolyl, 1,3,4-thiadiazolyl, 1,2,5-thiadiazolyl, etc.), etc.;

unsaturated condensed heterocyclic group containing 3 to 5 nitrogen atoms, for example, tetrazolopyridazinyl (e.g. tetrazolo[1,5-b]pyridazinyl, etc.), etc., and the like.

Thus defined heterocyclic group may optionally be substituted by one or more, same or different, suitable substituent(s) such as: lower alkyl (e.g. methyl, ethyl, etc.); lower alkoxy (e.g. methoxy, ethoxy, propoxy, etc.); lower alkylthio (e.g. methylthio, ethylthio, etc.); lower alkylamino (e.g. methylamino, etc.); hydroxy; halogen (e.g. chloro, bromo, etc.); amino protected amino as aforementioned; cyano; nitro; carboxy; protected carboxy as aforementioned; sulfo; lower alkanimidoylamino(lower)alkyl (e.g. formimidoylaminomethyl, formimidoylaminoethyl, acetimidoylaminomethyl, etc.); protected lower alkanimidoylamino(lower)alkyl such as nitrophenyl(lower)alkoxycarbonyl(lower)alkanimidoylamino(lower)alkyl (e.g. 4-nitrobenzyloxycarbonylacetamidoylaminomethyl, etc.); heterocyclic group such as pyridyl (e.g. 4-pyridyl, etc.); and the like.

More preferred example of the "heterocyclic group containing 3 to 5 hetero atoms which may have suitable substituent(s)" thus defined may be oxadiazolyl which may have lower alkyl such as 5-lower alkyl-1,3,4-oxadiazol-2-yl (e.g. 5-methyl-1,3,4-oxadiazol-2-yl, etc.), tetrazolyl which may have lower alkyl such as 1-lower alkyl-1H-tetrazol-5-yl (e.g. 1-methyl-1H-tetrazol-5-yl, etc.), thiadiazolyl which may have lower alkyl or lower alkanimidoylamino(lower)alkyl or protected lower alkanimidoylamino(lower)alkyl or heterocyclic group such as 5-lower alkyl-1,3,4-thiadiazol-2-yl (e.g. 5-methyl-1,3,4-thiadiazol-2-yl, etc.), 5-lower alkanimidoylamino(lower)alkyl-1,3,4-thiadiazol-2-yl (e.g. 5-acetimidoylaminomethyl-1,3,4-thiadiazol-2-yl, etc.), 5-nitrophenyl(lower)alkoxycarbonyl(lower)alkanimidoylamino(lower)alkyl-1,3,4-thiadiazol-2-yl [e.g. 5-(4-nitrobenzyloxycarbonylacetimidoylaminomethyl)-1,3,4-thiadiazol-2-yl, etc.], 5-pyridyl-1,3,4-thiadiazol-2-yl [e.g. 5-(4-pyridyl)-1,3-thiadiazol-2-yl, etc.], triazolyl which may have lower alkyl such as 5-lower alkyl-4H-1,2,4-triazol-3-yl (e.g. 5-methyl-4H-1,2,4-triazol-3-yl, etc.), tetrazolopyridazinyl (e.g. tetrazolo[1,5-b]pyridazin-6-yl, etc.).

Suitable "lower alkyl" may include straight or branched one such as methyl, ethyl, propyl, isopropyl, butyl, isobutyl, pentyl, isopentyl, hexyl, or the like, and the more preferred one is $C_1$-$C_4$ alkyl, and the most preferred one is methyl.

Suitable "acyl" for $R^5$ may include the same ones as those given in the hydroxy-protective group in "a protected hydroxy group" and preferred one may be diarylphosphono, arenesulfonyl and lower alkanesulfonyl which may have halogen, and more preferred one is diarylphosphono and halo(lower)alkanesulfonyl (e.g. trifluoromethanesulfonyl, etc.).

Suiteble "an acid residue" may include halogen (e.g. chlorine, bromine, iodine, etc.), mono-substituted sulfo such as mono(lower)alkylsulfo (e.g. methylsulfo, ethylsulfo, etc.), sulfonyl, and the like.

The processes for preparing the object compounds (I) of the present invention are explained in details in the following.

(1) Process 1

The compounds (I) or a salt thereof can be prepared by reacting the compound (II) or a salt thereof with an acylating agent (First Step), and then reacting the resultant compound (III) or a salt thereof with the compound (IV) or a salt thereof (Second Step).

(i) For First Step

The present step can be carried out in a conventional acylation manner.

Suitable salt of the compounds (II) and (III) may include the same one as that for the compounds (I).

Suitable acylating agents may include ones which can introduce the acyl group as mentioned above into the compound (II), and preferable acylating agents may be organic sulfonic, phosphinic or phosphoric acid or its reactive derivative such as acid halide, acid anhydride, and the like, for example, arenesulfonyl halide (e.g. benzenesulfonyl chloride, p-toluenesulfonyl chloride, p-nitrobenzenesulfonyl chloride, p-bromobenzenesulfonyl chloride, etc.), arenesulfonic anhydride, (e.g. benzenesulfonic anhydride, p-toluenesulfonic anhydride, p-nitrobenzenesulfonic anhydride, etc.), lower alkanesulfonyl halide which may have additional halogen (e.g. methanesulfonyl chloride, ethanesulfonyl chloride, trifluoromethanesulfonyl chloride, etc.), lower alkanesulfonic anhydride which may have halogen (e.g. methanesulfonic anhydride, ethanesulfonic anhydride, trifluoromethanesulfonic anhydride, etc.), diarylphosphono halide (e.g. diphenylphosphono chloride, ditolylphosphono chloride, etc.), di(lower)alkylphosphono halide (e.g. diethylphosphono chloride, etc.), diarylphosphinoyl halide (e.g. diphenylphosphinoyl halide, etc.), and the like.

The reaction is usually carried out in a conventional solvent such as water, acetone, dioxane, acetonitrile, chloroform, methylene chloride, hexamethylphosphoramide, ethylene chloride, tetrahydrofuran, ethyl acetate, dimethylsulfoxide, N,N-dimethylformamide, pyridine or any other organic solvents which do not adversely influence the reaction, or a mixture thereof.

When the acylating agent is used in a free acid form or its salt form in this reaction, the reaction is preferably carried out in the presence of a conventional condensing agent such as carbodiimide compounds (e.g. N,N'-diethylcarbodiimide, N,N'-diisopropylcarbodiimide, N,N'-dicyclohexylcarbodiimide, N-cyclohexyl-N'-morpholinoethylcarbodiimide, N-cyclohexyl-N'-(4-diethylaminocyclohexyl)carbodiimide, N-ethyl-N'-(3-dimethylaminopropyl)carbodiimide, etc.); N,N'-carbonyldi(imidazole), N,N'-carbonylbis-(2-methylimidazole); keteneimine compounds (e.g. pentamethyleneketene-N-cyclohexylimine, diphenylketene-N-cyclohexylimine); ethoxyacetylene; 1-alkoxy-1-chloroethylene; ethyl polyphosphate; isopropyl polyphosphate; phosphorus oxychloride; phosphorus trichloride; thionyl chloride; oxalyl chloride; a combination of triphenylphosphine with carbon tetrachloride or diazenedicarboxylate; 2-ethyl-7-hydroxybenzisoxazolium salt; 2-ethyl-5-(m-sulfophenyl)isoxazolium hydroxide intra-molecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; or the like.

The reaction may also be carried out in the presence of an inorganic or organic base such as an alkali metal bicarbonate (e.g. sodium bicarbonate, potassium bicarbonate, etc.), alkali metal carbonate (e.g. sodium carbonate, potassium carbonate, etc.), alkaline earth metal carbonate (e.g. magnesium carbonate, calcium carbonate, etc.), tri(lower)alkylamine (e.g. trimethylamine, triethylamine, N,N-diisopropyl-N-ethylamine, etc.), pyridine compounds (e.g. pyridine, picoline, lutidine, N,N-di(lower)alkylaminopyridine such as N,N-dimethylaminopyridine, etc.), quinoline, N-lower alkylmorpholine (e.g. N-methylmorpholine, etc.), N,N-di(lower)alkylbenzylamine (e.g. N,N-dimethylbenzylamine, etc.), and the like.

The reaction temperature is not critical, and the reaction is usually carried out under from cooling to warming.

With regard to the compound (II), it is to be noted that the 3,7-dioxo-1-azabicyclo[3.2.0]heptane ring system of the following formula (IIA) is well known to lie in tautomeric relation with the 3-hydroxy-7-oxo-1-azabicyclo[3.2.0]hept-2-ene ring system of the following formula (IIB), and accordingly, it is to be understood that both of these ring systems are substantially the same.

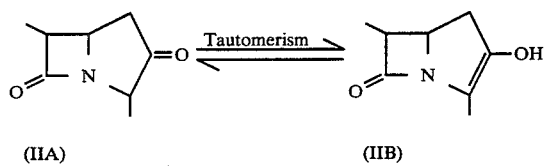

(IIA)    (IIB)

The compound (III) or a salt thereof can be isolated in a conventional manner, but can also be used as the starting compound of the Second Step without any isolation.

(ii) For Second Step

The present step can be carried out in a conventional manner which can be applied to transformation of the acyloxy group to the group: —S—$R^3$, wherein $R^3$ is as defined above.

Suitable salt of the compound (IV) may include the same salt with a base as that for the compounds (I), and further salt of the compound (IV), wherein $R^3$ is pyridyl which may have suitable substituent(s), may include the same salt with an acid as that for the compounds (I) and additionally salt with metallic halide such as stannic chloride or the like.

The reaction is usually carried out in a conventional solvent such as those given in the explanation of the First Step.

The reaction may also be carried out in the presence of an inorganic or organic base such as those given in the explanation of the First Step.

The reaction temperature is not critical, and the reaction is usually carried out under from cooling to warming.

(2) Process (2)

The compound (I-b) or a salt thereof can be prepared by subjecting the compound (I-a) or a salt thereof to removal reaction of the hydroxy-protective group in $R_a{}^1$ and the carboxy-protective group in $R_a{}^2$.

Suitable salt of the compound (I-a) may include the same as that for the object compounds (I).

Suitable salt of the compound (I-b) may include the same one as that for the object compounds (I).

The present reaction is carried out in a conventional method such as hydrolysis, reduction, and the like.

(i) Hydrolysis

Hydrolysis is preferably carried out in the presence of a base or an acid. Suitable base may include an alkali metal hydroxide (e.g. sodium hydroxide, potassium hydroxide, etc.), an alkaline earth metal hydroxide (e.g. magnesium hydroxide, calcium hydroxide, etc.), an alkali metal carbonate (e.g. sodium carbonate, potassium carbonate, etc.), an alkaline earth metal carbonate (e.g. magnesium carbonate, calcium carbonate, etc.), an alkali metal bicarbonate (e.g. sodium bicarbonate, potassium bicarbonate, etc.), and the like.

Suitable acid may include an organic acid (e.g. formic acid, acetic acid, propionic acid, trifluoroacetic acid, benzenesulfonic acid, p-toluenesulfonic acid, etc.) and an inorganic acid (e.g. hydrochloric acid, hydrobromic acid, sulfuric acid, phosphoric acid, etc.). The acidic hydrolysis using trifluoroacetic acid is usually accelerated by addition of cation trapping agent (e.g. phenol, anisole, etc.).

In case that the hydroxy-protective group is tri(lower)alkylsilyl(lower)alkoxycarbonyl, the hydrolysis can be carried out in the presence of tri(lower)alkylammonium halide (e.g. tributylammonium fluoride, etc.).

The reaction is usually carried out in a solvent such as water, methylene chloride, an alcohol (e.g. methanol, ethanol, etc.), tetrahydrofuran dioxane, acetone or any other solvents which do not adversely influence the reaction, or a mixture thereof. A liquid base or acid can be also used as the solvent.

The reaction temperature is not critical and the reaction is usually carried out under from cooling to heating.

(ii) Reduction

The reduction method applicable for this removal reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, sulfuric acid, etc.); and conventional catalytic reduction in the presence of a conventional metallic catalyst such as palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), platinum catalyts (e.g. platinum plate, spongy platinum, platinum black, colloidal platinum, platinum oxide, platinum wire, etc.), and the like.

In case that the catalytic reduction is applied, the reaction is preferably carried out around neutral condition.

The reaction is usually carried out in a conventional solvent such as water, alkanol (e.g. methanol, ethanol, propanol, etc.), dioxane, tetrahydrofuran, acetic acid or any other organic solvents which do not adversely influence the reaction, or a mixture thereof around a neutral condition.

The reaction temperature is not critical, and the reaction is usually carried out under from cooling to warming.

The removal methods can be selected according to the kind of the hydroxy- and carboxy-protective groups to be removed.

In the present process, in case that $R^3$ of the starting compound (I-a) possesses a protected lower alkanimidoylamino(lower)alkyl as a substituent, said substituent is also transformed into a free lower alkanimidoylamino(lower)alkyl during the reaction, and such a case is included within the scope of the present process.

The present process includes within the scope thereof a case that the hydroxy-protective group for $R_a^1$ is firstly removed and then the carboxy-protective group for $R_a^2$ is secondly removed to give the object compound (I-b), or a case that the carboxy-protective group for $R_a^2$ is firstly removed and then the hydroxy-protective group for $R_a^1$ is secondly removed to give the object compound (I-b), or a case that the hydroxy-protective group for $R_a^1$ and the carboxy-protective group for $R_a^2$ are removed at the same time to give the object compound (I-b).

(3) Process 3

The compound (I-d) or a salt thereof can be prepared by reacting the compound (I-c) or a salt thereof with the compound (V).

Suitable salt of the compounds (I-c) and (I-d) may include the same one as that for the compounds (I).

This reaction can be carried out in the presence of a base such as that exemplified for the Process 1.

This reaction is usually carried out in a conventional solvent such as water, dioxane, tetrahydrofuran or any other organic solvents which do not adversely influence the reaction, or a mixture thereof.

The reaction temperature is not critical, and the reaction is usually carried out under from cooling to warming.

It is to be noted that, in the aforementioned reactions in Processes 1 to 3 or the post-treatment of the reaction mixture therein, in case that the starting or object compounds possess an optical isomer(s), it may occasionally be transformed into the other optical isomer(s), and such cases are also included within the scope of the present invention.

In case that the object compounds (I) have a free carboxy group for $R^2$, it may be transformed into its pharmaceutically acceptable salts by a conventional manner.

Methods A to C for preparing the new starting compound (II) used in Process 1 are explained in details in the following.

(A) Method A-1

The compound (II-b) can be prepared by reacting the compound (II-a) with a lower alkylating agent.

Suitable lower alkylating agent used in this reaction may include a conventional one which can be applied to lower alkylation of a hydroxy group such as di(lower)alkyl sulfate (e.g. dimethyl sulfate, diethyl sulfate, etc.), lower alkyl sulfonate (e.g. methyl sulfonate, etc.), lower alkyl halide (e.g. methyl iodide, ethyl iodide, propyl bromide, etc.), or the like.

This reaction is preferably carried out in the presence of an inorganic or organic base such as those given in the explanation of the Process 1, and in addition, lower alkyl lithium (e.g. butyl lithium, etc.), alkali metal hydride (e.g. sodium hydride, potassium hydride, etc.), alkaline earth metal hydride (e.g. calcium hydride, etc.), and the like.

This reaction is usually carried out in a conventional solvent such as tetrahydrofuran, dioxane, N,N-dimethylformamide, dimethylsulfoxide, hexamethylphosphoramide or any other solvents which do not adversely influence the reaction, or a mixture thereof.

The reaction temperature is not critical and the reaction is usually carried out under from cooling to warming.

Method A-2

The compound (II-c) can be prepared by subjecting the compound (II-b) to hydrolysis.

Hydrolysis is preferably carried out in the presence of an acid such as that given for Hydrolysis in the Process 2, and accordingly, reaction conditions (e.g. solvents, reaction temperature, etc.) can be referred to said explanation.

(B) Method B-1

The compound (II-d) or a salt thereof can be prepared by subjecting the compound (II-c) to oxidation.

Suitable salt of the compound (II-d) may include the same salt as that for the compounds (I).

This reaction can be carried out in a conventional manner using an oxidizing agent which can be applied to converting a hydroxymethyl group to a carboxy group such as potassium permanganate, chromic compound (e.g. chromic acid, sodium chromate, dichromic acid, sodium dichromate, pyridinium dichromate, etc.), and the like.

The reaction is usualy carried out in a conventional solvent such as water, acetone, dioxane, dimethylformamide, pyridine or any other organic solvents which do not adversely influence the reaction, or a mixture thereof.

The reaction temperature is not critical, and the reaction is usually carried out under from cooling to warming. .

Method B-2

The compound (II-e) or a salt thereof can be prepared by reacting the compound (II-d) or a salt thereof with malonic acid or its derivative or a salt thereof.

Suitable salt of the compound (II-e) may include the same one as that for the compounds (I).

Suitable salt of the malonic acid or its derivative may include the same salt with a base as that for the compounds (I).

Suitable derivative of the malonic acid may include mono- or di-ester such as those given for the protected carboxy group.

The reaction can be carried out in a conventional solvent such as dioxane, tetrahydrofuran, N,N-dimethylformamide or any other organic solvents which do not adversely influence the reaction, or a mixture thereof, in the presence of a condensing agent such as those given in Process 1.

The reaction temperature is not critical, and the reaction is usually carried out under from cooling to warming.

Method B-3

The compound (II-f) or a salt thereof can be prepared by reacting the compound (II-e) or a salt thereof with acid azide.

Suitable salt of the compound (II-f) may include the same one as that for the compounds (I).

Suitable acid azide may include arenesulfonyl azide which may have substituent (e.g. benzenesulfonyl azide, p-toluenesulfonyl azide, dodecylbenzenesulfonyl azide, p-carboxybenzenesulfonyl azide, naphthalene-2-sulfonyl azide, etc.), lower alkanesulfonyl azide (e.g. methanesulfonyl azide, ethanesulfonyl azide, etc.), and the like.

The reaction is usually carried out in a conventional solvent such as tetrahydrofuran, dioxane, methylene chloride, acetonitrile, N,N-dimethylformamide or any other organic solvents which do not adversely influence the reaction, or a mixture thereof, preferably in the presence of a base such as those given in Process 1.

The reaction temperature is not critical, and the reaction is usually carried out under from cooling to warming.

Method B-4

The compound (II) or a salt thereof can be prepared by subjecting the compound (II-f) or a salt thereof to cyclization.

The reagent used in this cyclization reaction may include metal (e.g. cupper, etc.), metallic acetate (e.g. lead acetate, palladium acetate, rhodium acetate, cupric acetate, etc.), metallic sulfate (e.g. cupric sulfate, etc.), and the like.

The reaction is usually carried out in a conventional solvent such as benzene, toluene, tetrahydrofuran, dioxane, acetonitrile or any other organic solvents which do not adversely influence the reaction, or a mixture thereof.

The reaction temperature is not critical, and the reaction is usually carried out from at ambient temperature to refluxing.

(C) Method C-1

The compound (II-h) or a salt thereof can be prepared by reacting the compound (II-g) or a salt thereof with a lower alkylating agent.

Suitable salts of the compounds (II-g) and (II-h) may include the same one as that for the compounds (I).

This reaction can be carried out in substantially the same manner as that of the Method A-1, and accordingly, the reaction reagents and the reaction conditions (e.g. solvent, reaction temperature, etc.) can be referred to those of said Method A-1.

Method C-2

The compound (II-i) can be prepared by (i) reacting the compound (II-h) or a salt thereof with ozone, (ii) degrading the resultant ozonide in a conventional manner, (iii) introducing the formyl-protective group into the resultant compound, and then (iv) subjecting the resultant compound to solvolysis, if necessary.

The present reaction can be represented by the following reaction schemes.

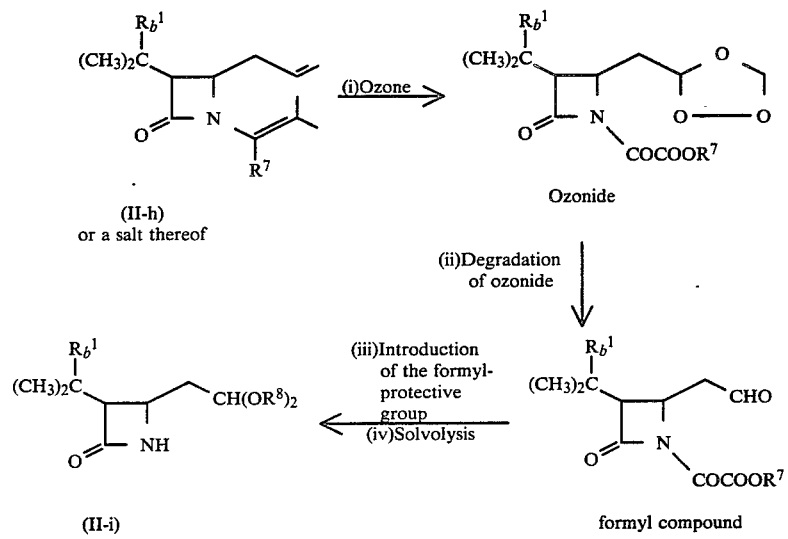

in which $R_b^1$, $R^7$ and $R^8$ are each as defined above.

This reaction can be carried out in a conventional manner which can be applied to conversion of a allyl group to dialkoxyethyl group.

The ozonide produced by the starting compounds with ozone is usually degraded by reduction or heating.

The method of the reduction can be carried out in substantially the same manner as that of Process 2, and therefore the reaction conditions (e.g. solvent, reaction temperature, etc.) can be referred to said explanation, and in addition, as suitable reducing agents, there may be exemplified by trialkyl phosphite (e.g. trimethyl-phosphite, etc.), triphenylphosphine, dimethyl sulfide, sodium bisulfite, sodium sulfite, sodium iodide, stannous chloride, and the like.

Suitable formyl-protective group is di(lower)alkyl acetal which can be prepared by reacting the formyl compound with tri(lower)alkyl orthoformate (e.g. trimethyl orthoformate, etc.), and the like, preferably in the presence of an acid such as that given in Hydrolysis for the Process 2.

Solvolysis is usually carried out in the presence of lower alkanol (e.g. methanol, ethanol, etc.), or in the presence of an inorganic base as exemplified for Hydrolysis in the Process 2 or alkali metal alkoxide (e.g. sodium methoxide, etc.).

This reaction is usually carried out in a conventional solvent such as methanol, ethanol, propanol, or any other solvents which do not adversely influence the reaction, or a mixture thereof.

The reaction temperature is not critical and the reaction is preferably carried out from under cooling to under heating.

Method C-3

The compound (II-j) can be prepared by subjecting the compound (II-i) to hydrolysis.

Hydrolysis is preferably carried out in the presence of an acid such as that given for Hydrolysis in the Process 2, and accordingly, reaction conditions (e.g. solvents, reaction temperature, etc.) can be referred to said explanation.

Method C-4

The compound (II-k) or a salt thereof can be prepared by oxidizing the compound (II-i).

Suitable salt of the compound (II-k) may include the same salt with the base as exemplified for the compounds (I).

Suitable oxidizing agent used in this reaction may include a conventional one which can be applied to conversion of a formyl group to a carboxy group such as those given in the Method B-1.

This reaction is usually carried out in a conventional solvent such as dichloromethane, acetone, dioxane, diethyl ether, benzene, toluene or any other solvents which do not adversely influence the reaction, or a mixture thereof.

The reaction temperature is not critical and the reaction is preferably carried out from under cooling to warming.

The object compounds (I) and the pharmaceutically acceptable salts thereof of the present invention are novel and exhibit high absorption values in urine and bile and high antimicrobial activity, inhibiting the growth of a wide variety of pathogenic microorganisms including Gram-positive and Gram-negative microorganisms and are useful as antimicrobial agents.

In the present invention, the object compounds (I) possessing more potent antimicrobial activity can be represented by the following formula:

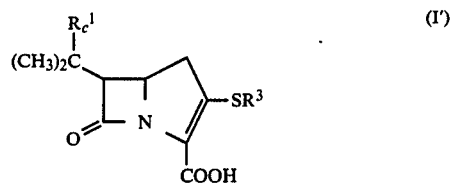

in which
$R_c^1$ is hydroxy or lower alkoxy, and
$R_3$ is as defined above,
and its pharmaceutically acceptable salt.

Particularly, the compounds (I) possessing the most potent antimicrobial activity can be represented by the following formula:

(I″)

in which $R_c^1$ and $R^3$ are each as defined above, and an alkali metal salt thereof.

Further, the object compounds (I) and the pharmaceutically acceptable salts thereof are also useful as β-lactamase inhibitors.

Now, in order to show the utility of the object compounds (I), the test data on antimicrobial activity and inhibitory effect on β-lactamase activity of representative compounds of the object compounds (I) of this invention are shown in the following.

(1) in vitro Antimicrobial Activity

Test Compounds

Sodium (5R, 6R)-3-(4-pyridylthio)-6-(1-hydroxy-1-methylethyl)-7-oxo-1-azabicyclo[3.2.0]hept-2-ene-2-carboxylate (hereinafter referred to as Compound A), Potassium (5R, 6R)-3-(5-methyl-1,3,4-thiadiazol-2-ylthio)-6-(1-hydroxy-1-methylethyl)-7-oxo-1-azabicyclo[3.2.0]hept-2-ene-2-carboxylate. (hereinafter referred to as Compound B),

Test Method

In vitro Antimicrobial activity was determined by the two-fold agar-plate dilution method as described below.

One loopful of an overnight culture of each test strain in Trypticase-soy broth ($10^6$ viable cells per ml) was streaked on heart infusion agar (HI-agar) containing graded concentrations of the test compound, and the minimal inhibitory concentration (MIC) was expressed in terms of μg/ml after incubation at 37° C. for 20 hours.

| Test Results: | | |
|---|---|---|
| | MIC (μg/ml) | |
| | Test Compounds | |
| Test Strains | A | B |
| Staphylococcus aureus 209P JC-1 | 0.10 | 0.20 |
| Esherichia coli NIHJ JC-2 | 0.10 | 0.20 |

(2) Inhibitory Effect on β-Lactamase Activity

1 Inactivation of β-Lactamase

Test Compounds

Sodium (5R,6S)-3-(4-pyridylthio)-6-(1-hydroxy-1-methylethyl)-7-oxo-1-azabicyclo[3.2.0]hept-2-ene-2-carboxylate (hereinafter referred to as Compound C)

Potassium (5R,6R)-3-(1-methyl-1H-tetrazol-5-ylthio)-6-(1-hydroxy-1-methylethyl)-7-oxo-1-azabicyclo[3.2.0]hept-2-ene-2-carboxylate (hereinafter referred to as Compound D)

Test β-Lactamases

R-TEM Penicillinase derived from *Escherichia coli* 18.

Ia Cephalosporinase derived from *Enterobacter cloacae* 91.

Test Method

Test compound solution (100 μg/ml) was incubated for 5 minutes at 37° C. with β-lactamase before determination of enzymatic activity. β-Lactamase activity was measured by direct spectrophotometric assay using a chromogenic cephalosporin as a substrate. The extent of inactivation was expressed as percent ratio of inactivated activity.

| | Test Results | |
|---|---|---|
| | Inactivation (%) Test Compounds | |
| β-Lactamases | Compound C | Compound D |
| R-TEM Penicillinase | >95 | >95 |
| Ia Cephalosporinase | >95 | >95 |

2 Synergistic Protecting Effect on experimental mice infection

Test Compounds (i) Combination of Compound C (Compound of the present invention) and Ceftizoxime (known antimicrobial agent, hereinafter referred to as CZX) (1:1 by weight).

(ii) Combination of Compound C (Compound of the present invention) and Cefazolin (known antimicrobial agent, hereinafter referred to as CEZ) (1:1 by weight).

Test Animals 4-week-old male ICR strain-mice, weighing 21.5±1.5 g.

Test Method $1.1 \times 10^5$ Colony forming unit of *Escherichia coli* 36 suspended in 0.5 ml of 5% mucin were intraperitoneally injected.

One hour after challenge, mice were treated subcutaneously with various doses of test compound. The ED$_{50}$ values were calculated by the probit method from the number of mice surviving 4 days of observation.

| | Test Results | | |
|---|---|---|---|
| | (i) | | |
| Compounds | Compound C per se | CZX per se | Combination of Compound C and CZX |
| ED$_{50}$ values (mg/kg) | >112 | 3.42 | 0.846 |
| | (ii) | | |
| Compounds | Compound C per se | CEZ per se | Combination of Compound C and CEZ |
| ED$_{50}$ values (mg/kg) | >112 | 20.8 | 14.5 |

For therapeutic administration, the object compounds (I) and the pharmaceutically acceptable salts thereof of the present invention are used in the form of conventional pharmaceutical preparation which contains said compounds, as active ingredients, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade, and the like.

If needed, there may be included in the above preparations auxiliary substances, stabilizing agents, wetting agents and other commonly used additives such as lactose, stearic acid, magnesium stearate, terra alba, sucrose, corn starch, talc, gelatin, agar, pectin, peanut oil, olive oil, cacao butter, ethylene glycol, tartaric acid, citric acid, fumaric acid, and the like.

While the dosage of the compounds (I) may very from and also depend upon the age, conditions of the patient, a kind of diseases, a kind of the compounds (I) to be applied, etc. In general, amounts between 1 mg and about 4,000 mg or even more per day may be administered to a patient. An average single dose of about 50 mg, 100 mg, 250 mg, 500 mg, 1000 mg, 2000 mg of the object compounds (I) of the present invention may be used in treating diseases infected by pathogenic microorganisms.

Further, it is to be understood that the object compounds (I) and pharmaceutically acceptable salts thereof are also used in the form of antimicrobial combination which contains said compounds, as β-lactamase inhibitors, in admixture with other antimicrobial agents such as penicillin and cephalosporin compounds.

The preferred combination of the object compounds of the present invention and other antimicrobial agents may be a combination of the compounds (I) and ampicillin, amoxicillin, cefazolin or ceftizoxime.

The combination ratio of the object compounds (I) or its pharmaceutically acceptable salt and other antimicrobial agents or its pharmaceutically acceptable salt in the present antimicrobial combination may vary depending on the kinds of pathogens and the symptoms of the patients, to which the present combination is applied, but may usually be selected within a range of 1:50 to 50:1 by weight, preferably 1:4 to 4:1 by weight and most preferably 1:1 by weight.

Further, it is to be noted that the present antimicrobial combination may be applied to human being and other animals in conventional forms, examples of which are illustrated as follows.

For applying the present antimicrobial combination to human being, it is preferable to apply it in the form of intravenous or intramuscular injection. It may also be applied locally in the form of a powder, a suppository or an ointment. When used as an injection, it may be applied in admixture with a solid or liquid carrier or diluent which is usually used for the conventional antibiotic injections, and further, may also be applied together with other medicines such as analgesics (e.g. lidocaine) which are usually used in injections. The most preferred carrier or diluent is water. When used as a suppository and an ointment, it may be used in admixture with conventional suppository and ointment bases, respectively.

The dosage of the present antimicrobial combination may vary depending on the kinds of the object compounds (I) and other antimicrobial agents, the combination ratio thereof and various factors such as the weight and age of the patient, the kind and severity of the infection, and the kind of the application mode. However, it is to be understood that, as the dosage of the effective ingredient included in the present antimicrobial combination, it may be effectively administered to the patient in a dose of about 0.1 to 50 mg/kg/day. The total daily amount mentioned above may be divisionally given to the patient at the interval of 6–12 hours per day.

The following examples are given for the purpose of illustrating the present invention.

Preparation of the starting compound (II)

Preparation 1

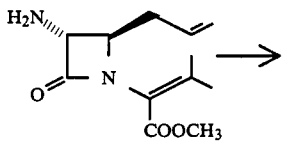

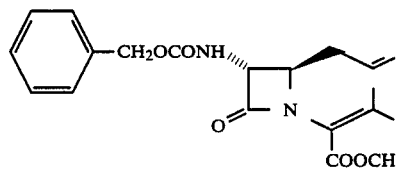

To a solution of methyl [(3R,4R)-3-amino-4-allyl-2-oxoazetidin-1-yl]-3-methylbut-2-enoate (7.0 g) in methylene chloride (110 ml) were added 2,6-lutidine (4.11 ml) and benzyl chloroformate (5.03 ml) at 0° C. and the mixture was stirred for 30 minutes at 0° C. The reaction mixture was diluted with ethyl acetate (800 ml) and the solution was washed with diluted hydrochloric acid, brine, aqueous saturated sodium bicarbonate, and brine. The organic layer was dried over magnesium sulfate and evaporated in vacuo. The residue was chromatographed on silica gel (200 g) eluting with a mixture of methylene chloride and ethyl acetate (20:1–4:1) to give methyl [(3R,4R)-3-benzyloxycarbonylamino-4-allyl-2-oxoazetidin-1-yl]-3-methylbut-2-enoate (10.7 g) as an oil.

IR (CH2Cl2): 3380, 1750, 1720 cm−1.

NMR (CD3OD) δ: 1.95 (s, 3H), 2.17 (s, 3H), 2.44 (t, 2H, J=7 Hz), 3.73 (s, 3H), 4.06 (dt, 1H, J=2.5, 7 Hz), 4.44 (d, 1H, J=2.5 Hz), 4.9–5.2 (m, 2H), 5.10 (s, 2H), 5.5–6.0 (m, 1H), 7.34 (s, 5H).

Preparation 2

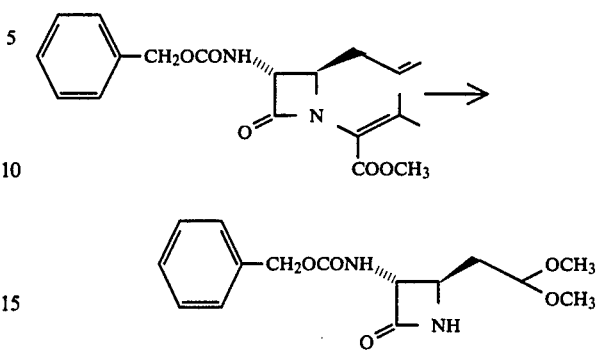

Ozone was bubbled into a solution of methyl [(3R,4R)-3-benzyloxycarbonylamino-4-allyl-2-oxoazetidin-1-yl]-3-methylbut-2-enoate (5 g) in methanol (100 ml) at −60° C. until a blue color was appeared. After stirring for 10 minutes at −60° C., the mixture was purged with nitrogen. Dimethyl sulfide (5 ml) was added to the mixture at −60° C. and the mixture was allowed to warm to 0° C. during 15 minutes. After stirring for an hour at 0° C., the mixture was left for 20 hours at ambient temperature. Dimethyl sulfide (2 ml), trimethyl orthoformate (5 ml), and p-toluenesulfonic acid monohydrate (150 mg) were added to the mixture and the mixture was heated at 50° C. for 6 hours. Pyridine (0.076 ml) was added to the reaction mixture at ambient temperature and the mixture was evaporated in vacuo. The residue was dissolved in ethyl acetate and the solution was washed with water, dilute hydrochloric acid, brine, aqueous sodium bicarbonate, and brine.

The organic layer was dried over magnesium sulfate, and evaporated in vacuo. The residue was dissolved in methanol (100 ml), and the solution was heated at 50° C. for 3 hours and left at ambient temperature for 2 days. The mixture was evaporated in vacuo and the residue was chromatographed on silica gel (100 g) eluting with a mixture of methylene chloride and acetone (10:1–2:1) to give (3R,4R)-3-benzyloxycarbonylamino-4-(2,2-dimethoxyethyl)azetidin-2-one (2.83 g) as an oil.

IR (CH2Cl2): 1770, 1720 cm−1.

NMR (acetone-d6) δ: 1.8–2.2 (m, 2H), 3.30 (s, 6H), 3.66 (dt, 1H, J=3, 7 Hz), 4.42 (dd, 1H, J=3, 9 Hz), 4.51 (t, 1H, J=5.5 Hz), 5.12 (s, 2H), 7.0 (brs, 1H), 7.2 (m, 1H), 7.40 (s, 5H).

Preparation 3

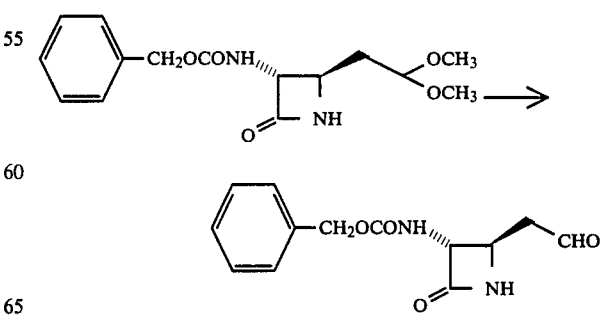

To a solution of (3R,4R)-3-benzyloxycarbonylamino-4-(2,2-dimethoxyethyl)azetidin-2-one (2.15 g) in acetic acid (35.2 ml) were added dimethylsulfide (2 ml) and water (8.8 ml) at ambient temperature and the mixture was heated at 50° C. for 4.5 hours. The reaction mixture was evaporated in vacuo and the residue was dissolved in xylene (40 ml). The mixture was evaporated in vacuo and the residue was chromatographed on silica gel (10 g) eluting with a mixture of methylene chloride and acetone (5:1–2:1) to give a crystalline solid. This crude crystals were washed with ether and dried over phosphorous pentoxide to give (3R,4R)-3-benzyloxycarbonylamino-4-(2-oxoethyl)azetidin-2-one (863 mg).

IR ($CH_2Cl_2$): 1780, 1720 $cm^{-1}$.

NMR (acetone-$d_6$)δ: 2.7–3.1 (m, 2H), 3.8–4.0 (m, 1H), 4.43 (dd, 1H, J=2,8 Hz), 5.07 (s, 2H), 6.9–7.2 (broad, 1H), 7.30 (s, 5H), 9.69 (s, 1H).

Preparation 4

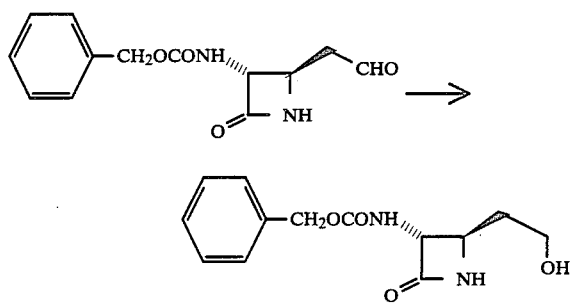

To a solution of (3R,4R)-3-benzyloxycarbonylamino-4-(2-oxoethyl)azetidin-2-one (850 mg) in methanol (17 ml) was added sodium borohydride (123 mg) at 0° C. and the mixture was stirred for 15 minutes at 0° C. Acetic acid (0.37 ml) was added to the mixture at 0° C. After stirring for 15 minutes at 0° C., the mixture was evaporated in vacuo. The residue was chromatographed on silica gel (17 g) eluting with a mixture of methylene chloride and methanol (20:1–10:1) to give a crystalline solid. This crude crystals were washed with ether and dried over phosphorous pentoxide to give (3R,4R)-3-benzyloxycarbonylamino-4-(2-hydroxyethyl)azetidin-2-one (748 mg).

mp. 120°–121° C.

IR ($CH_2Cl_2$): 1770, 1720 $cm^{-1}$.

NMR (acetone-$d_6$) δ: 1.7–2.11 (m, 2H), 2.82 (s, 1H), 3.5–3.8 (m, 3H), 4.39 (dd, 1H, J=3, 8 Hz), 5.05 (s, 2H), 6.9–7.3 (broad, 2H), 7.30 (s, 5H).

Preparation 5

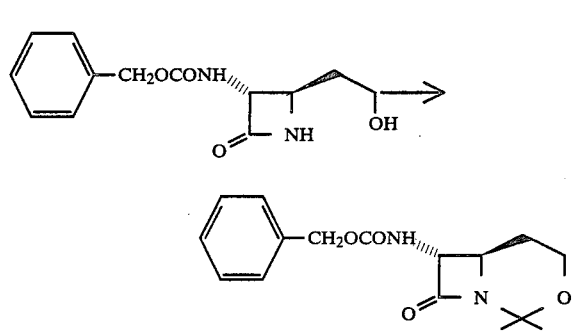

To a suspension of (3R,4R)-3-benzyloxycarbonylamino-4-(2-hydroxyethyl)azetidin-2-one (735 mg) in methylene chloride (30 ml) were added 2,2-dimethoxypropane (0.513 ml) and boron trifluoride etherate (0.026 ml) at 0° C. The mixture was stirred for 10 minutes at 0° C. and for 5 hours at ambient temperature. The reaction mixture was poured into a mixture of methylene chloride (30 ml) and aqueous sodium bicarbonate and sodium chloride (1:1). The organic layer was separated and the aqueous layer was extracted with methylene chloride (20 ml). The combined organic layers were washed with brine, dried over magnesium sulfate, and evaporated in vacuo. The residue was chromatographed on silica gel (16 g) eluting with a mixture of methylene chloride and acetone (10:1–5:1) to give (6R,7R)-7-benzyloxycarbonylamino-2,2-dimethyl-1-aza-3-oxabicyclo[4.2.0]octan-8-one (753 mg) as an oil.

IR ($CH_2Cl_2$): 1760, 1725 $cm^{-1}$.

NMR (acetone-$d_6$) δ: 1.36 (s, 3H), 1.61 (s, 3H), 1.4–2.1 (m, 2H), 3.5–3.9 (m, 3H), 4.38 (dd, 1H, J=2, 8 Hz), 5.08 (s, 2H), 7.0 (broad, 1H), 7.35 (s, 5H).

Preparation 6

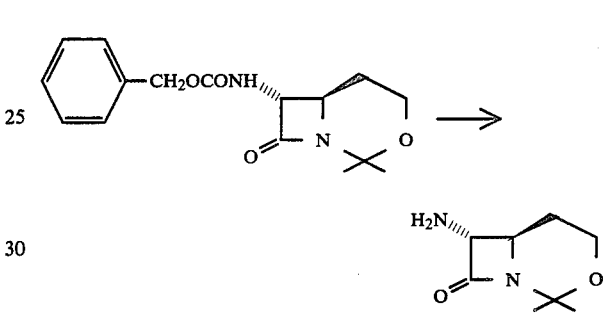

A mixture of (6R,7R)-7-benzyloxycarbonylamino-2,2-dimethyl-1-aza-3-oxabicyclo[4.2.0]octan-8-one (748 mg) and 10% palladium charcoal (180 mg) in ethyl acetate (15 ml) was stirred under a hydrogen atmosphere for 1.5 hours at ambient temperature. The mixture was filtered and the filtrate was evaporated in vacuo to give (6R,7R)-7-amino-2,2-dimethyl-1-aza-3-oxabicyclo[4.2.0]octan-8-one (382 mg) as a crystalline solid.

IR ($CH_2Cl_2$): 1740 $cm^{-1}$.

NMR ($CDCl_3$) δ: 1.42 (s, 3H), 1.72 (s, 3H), 1.5–2.1 (m, 2H), 1.86 (s, 2H), 3.34 (ddd, 1H, J=2, 5, 10 Hz), 3.6–3.9 (m, 3H).

Preparation 7

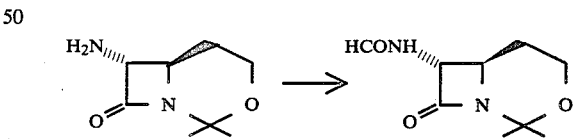

To a solution of (6R,7R)-7-amino-2,2-dimethyl-1-aza-3-oxabicyclo[4.2.0]octan-8-one (300 mg) were added pyridine (0.25 ml) and freshly prepared acetic formic anhydride (0.38 ml) at 0° C. After stirring for 45 minutes at 0° C., the reaction mixture was evaporated in vacuo. The residue was dissolved in xylene and the solution was evaporated in vacuo. The residue was chromatographed on silica gel (6 g) eluting with a mixture of methylene chloride and methanol (25:1–10:1) to give (6R,7R)-2,2-dimethyl-7-formamido-1-aza-3-oxabicyclo[4.2.0]octan-8-one (378 mg) as an oil.

IR ($CH_2Cl_2$): 1755, 1685 $cm^{-1}$.

NMR (CDCl₃) δ: 1.43 (s, 3H), 1.72 (s, 3H), 1.8–2.1 (m, 2H), 3.56 (ddd, 1H, J=2, 5, 10 Hz), 3.7–3.9 (m, 2H), 4.37 (dd, 1H, J=2, 8 Hz), 7.33 (broad d, 1H, J=8 Hz), 8.11 (s, 1H)

Preparation 8

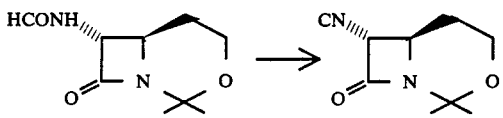

To a solution of (6R,7R)-2,2-dimethyl-7-formamido-1-aza-3-oxabicyclo[4.2.0]octan-8-one (345 mg) were added 2,6-lutidine (2.05 ml) and phosphorus oxychloride (0.52 ml) at 0° C. After stirring for 3 hours at 0° C., the mixture was poured into a mixture of ethyl acetate (80 ml) and ice-water. The organic layer was separated, washed in turn with 10% phosphoric acid, water, brine, an aqueous mixture of sodium bicarbonate and sodium chloride (1:1), and brine, dried over magnesium sulfate, and evaporated in vacuo. The crystalline residue was washed with a mixture of petroleum ether and ether (1:1) and dried over phosphorus pentoxide to give (6R,7R)-2,2-dimethyl-7-isocyano-1-aza-3-oxabicyclo[4.2.0]octan-8-one (205 mg).

IR (CH₂Cl₂): 2140, 1770 cm⁻¹.

NMR (CDCl₃) δ: 1.45 (s, 3H), 1.72 (s, 3H), 1.4–2.1 (m, 2H), 3.7–3.9 (m, 3H), 4.30 (d, 1H, J=2 Hz).

Preparation 9

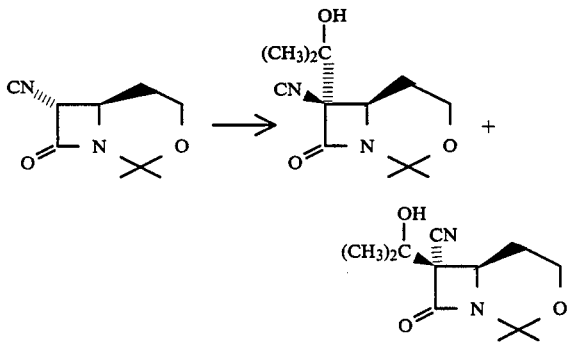

To a solution of (6R,7R)-2,2-dimethyl-7-isocyano-1-aza-3-oxabicyclo[4.2.0]octan-8-one (500 mg) in tetrahydrofuran (15 ml) was added a solution of n-butyllithium in hexane (2.33 ml of 1.55M solution) at −70° C. and the mixture was stirred at −70° C. for 15 minutes. A solution of acetone (0.265 ml) in tetrahydrofuran (2.4 ml) was added to the reaction mixture at −70° C. and the mixture was stirred at −70° C. for 25 minutes. Acetic acid (0.477 ml) was added to the mixture at −70° C. After stirring at −70° C. for 20 minutes, the mixture was evaporated in vacuo. The residue was dissolved in ethyl acetate (80 ml) and the solution was washed with aqueous sodium bicarbonate. The aqueous layer was separated and extracted with ethyl acetate (20 ml). The combined organic layers were washed with brine, dried over magnesium sulfate, and evaporated in vacuo. The crystalline residue was washed with isopropyl ether and filtered to give (6R,7R)-2,2-dimethyl-7-(1-hydroxy-1-methylethyl)-7-isocyano-1-aza-3-oxabicyclo[4.2.0]octan-8-one (460 mg). The mother liquor was chromatographed on silica gel (5 g) eluting with a mixture of hexane and ethyl acetate (20:1–1:1) to give additional (6R,7R)-2,2-dimethyl-7-(1-hydroxy-1-methylethyl)-7-isocyano-1-aza-3-oxabicyclo[4.2.0]octan-8-one (65 mg) [(6R,7R)-isomer] and its (6R,7S)-isomer (103 mg).

For (6R,7R)-isomer:
IR (CH₂Cl₂): 2125, 1765 cm⁻¹.
NMR (CDCl₃) δ: 1.38 (s, 3H), 1.43 (s, 3H), 1.50 (s, 3H), 1.74 (s, 3H), 1.5–2.2 (m, 2H), 2.10 (s, 1H), 3.7–4.0 (m, 3H).

For (6R,7S)-isomer:
IR (CH₂Cl₂): 2125, 1765 cm⁻¹.
NMR (CDCl₃) δ: 1.40 (s, 3H), 1.48 (s, 3H), 1.63 (s, 3H), 1.74 (s, 3H), 1.5–1.9 (m, 1H), 2.21 (s, 1H), 2.6–3.0 (m, 1H), 3.7–4.0 (m, 3H).

Preparation 10

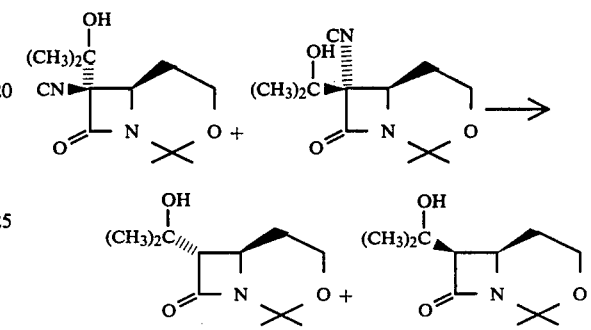

To a mixture of (6R,7R)-2,2-dimethyl-7-(1-hydroxy-1-methylethyl)-7-isocyano-1-aza-3-oxabicyclo[4.2.0]octan-8-one and its (6R,7S)-isomer (2.5 g) in benzene (75 ml) were added tributyltinhydride (3.07 ml) and azobisisobutyronitrile (170 mg) at ambient temperature and the mixture was refluxed for 30 minutes. The reaction mixture was chromatographed on silica gel (65 g) eluting with a mixture of methylene chloride and acetone (10:1–2:1) to give a crude product, which was purified by silica gel (75 g) chromatography (hexane and ethyl acetate) to give (6R,7S)-2,2-dimethyl-7-(1-hydroxy-1-methylethyl)-1-aza-3-oxabicyclo[4,2,0]-octan-8-one (0.545 g) [(6R,7S)-isomer] and its (6R,7R)-isomer (1.406 g).

For (6R,7S)-isomer:
IR (CH₂Cl₂): 1735 cm⁻¹.
NMR (CDCl₃) δ: 1.29 (s, 3H), 1.36 (s, 3H), 1.42 (s, 3H), 1.74 (s, 3H), 1.5–2.0 (m, 2H), 1.96 (s, 1H), 2.81 (d, 1H, J=2 Hz), 3.52 (ddd, 1H, J=2, 5.5, 11 Hz), 3.83 (dd, 2H, J=3, 8.5 Hz).

For (6R,7R)-isomer:
IR (CH₂Cl₂): 1735 cm⁻¹.
NMR (CDCl₃) δ: 1.28 (s, 3H), 1.40 (s, 3H), 1.47 (s, 3H), 1.74 (s, 3H), 1.5–2.0 (m, 1H), 1.98 (s, 1H), 2.5–2.9 (m, 1H), 3.15 (d, 1H, J=5 Hz), 3.6–3.9 (m, 3H).

Preparation 11

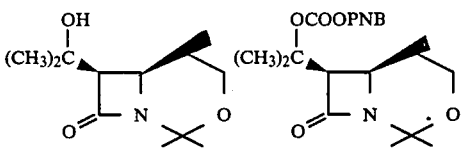

To a solution of (6R,7R)-2,2-dimethyl-7-(1-hydroxy-1-methylethyl)-1-aza-3-oxabicyclo[4.2.0]-octan-8-one (600 mg) in tetrahydrofuran (24 ml) was added a solution of n-butyllithium (2.36 ml of 1.55M solution in hexane) at −70° C. and the mixture was stirred at −70° C. for 15 minutes.

A solution of 4-nitrobenzyl chloroformate (788 mg) in tetrahydrofuran (7 ml) was added to the mixture at −70° C. After stirring at −70° C. for 15 minutes, the reaction mixture was allowed to warm to 0° C. during 50 minutes, stirred at 0° C. for 30 minutes, and evaporated in vacuo. The residue was dissolved in ethyl acetate (100 ml) and the solution was washed with aqueous sodium bicarbonate. The aqueous layer was separated and extracted with ethyl acetate (20 ml). The combined organic layers were washed with aqueous saturated sodium chloride, dried over magnesium sulfate, and evaporated in vacuo. The residue was chromatographed on silica gel (40 g) eluting with a mixture of hexane and ethyl acetate (10:1 to 1:1) to give a crystalline residue.

The residue was washed with isopropyl ether and filtered to give (6R,7R)-2,2-dimethyl-7-[1-(4-nitrobenzyloxycarbonyloxy)ethyl]-1-aza-3-oxabicyclo-[4.2.0]octan-8-one (520 mg).

IR (CH$_2$Cl$_2$): 1740, 1520, 1350 cm$^{-1}$.

NMR (CDCl$_3$) δ: 1.41 (s, 3H), 1.62 (s, 3H), 1.77 (s, 6H), 1.5–1.9 (m, 1H), 2.2–2.5 (m, 1H), 3.42 (d, 1H, J=5.5 Hz), 3.6–4.0 (m, 3H), 5.20 (s, 2H), 7.88 (A$_2$B$_2$, 4H, J=9 Hz).

Preparation 12

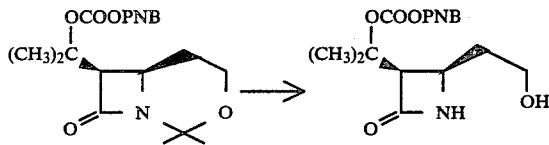

A solution of (6R,7R)-2,2-dimethyl-7-[1-methyl-1-(4-nitrobenzyloxycarbonyloxy)ethyl]-1-aza-3-oxabicyclo[4.2.0]octan-8-one (200 mg) in a mixture of acetic acid (3.2 ml) and water (0.8 ml) was heated at 65° C. for 1 hour. The mixture was cooled to room temperature and evaporated in vacuo. The crystalline residue was washed with ether to give (3R,4R)-4-(2-hydroxyethyl)-3-[1-methyl-1-(4-nitrobenzyloxycarbonyloxy)ethyl]azetidin-2-one (151 mg).

IR (CH$_2$Cl$_2$): 3575, 3375, 1750, 1520, 1350 cm$^{-1}$.

NMR (DMSO-d$_6$) δ: 1.57 (s, 3H), 1.64 (s, 3H), 1.88 (q, 2H, J=7 Hz), 3.1–3.6 (m, 3H), 3.6–3.9 (m, 1H), 4.47 (t, 1H, J=5 Hz), 5.23 (s, 2H), 7.90 (A$_2$B$_2$, 4H, J=9 Hz), 8.08 (s, 1H).

Preparation 13

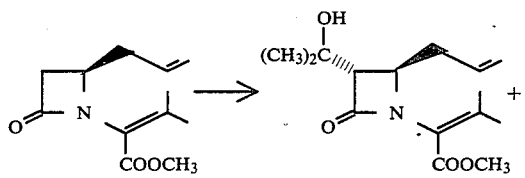

-continued

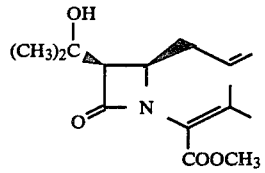

1.55M Butyl lithium-hexane solution (2.82 ml) was added to a solution of N-isopropylcyclohexylamino (0.72 ml) in tetrahydrofuran (6 ml) at −70° C., and the mixture was stirred for 20 minutes at −70° C. This mixture was added to a solution of methyl 3-methyl-2-[(4R)-2-oxo-4-allylazetidin-1-yl]but-2-enoate (247 mg) in tetrahydrofuran (6 ml) at −70° C. and the mixture was stirred for 1 hour at −70° C., and for 30 minutes at −30° C. Acetone (0.12 ml) was added to the reaction mixture at −70° C., and the mixture was stirred for 1 hour at −70° C. and for 30 minutes at −30° C.—−15° C. 3N Hydrochloric acid was added to the reaction mixture at −70° C. and the mixture was diluted with ethyl acetate (200 ml). The solution was washed with water, brine, aqueous sodium bicarbonate and brine, dried over magnesium sulfate, and evaporated in vacuo. Triethylamine (0.15 ml) was added to a solution of the residue in dichloromethane (3 ml) at 0° C. and the mixture was stirred overnight at ambient temperature. The reaction mixture was diluted with ethyl acetate (20 ml) and the solution was washed with 0.1N hydrochloric acid (15 ml) brine, aqueous sodium bicarbonate and brine, dried over magnesium sulfate, and evaporated in vacuo. The residue was chromatographed on silica gel (10 g) eluting with a mixture of benzene and acetone (10:1–2:1) to give methyl 3-methyl-2-[(3S,4R)-3-(1hydroxy-1-methylethyl)-2-oxo-4-allylazetidin-1-yl]but-2-enoate (100 mg);

IR (CH$_2$Cl$_2$): 1740, 1715 cm$^{-1}$.

NMR (CDCl$_3$) δ: 1.31 (s, 3H), 1.38 (s, 3H), 1.96 (s, 3H), 2.18 (s, 3H), 2.2–2.5 (m, 3H), 2.90 (d, 1H, J=3 Hz), 3.76 (s, 3H), 3.81 (dt, 1H, J=3, 7 Hz), 4.9–5.2 (m, 2H), 5.5–6.0 (m, 1H) and methyl 3-methyl-2-[(3R,4R)-3-(1-hydroxy-1-methylethyl)-2-oxo-4-allylazetidin-1-yl]but-2-enoate (50 mg).

NMR (CDCl$_3$) δ: 1.39 (s, 3H), 1.52 (s, 3H), 1.99 (s, 3H), 2.19 (s, 3H), 2.21 (broad s, 1H), 2.74 (t, 2H, J=7 Hz), 3.30 (d, 1H, J=6 Hz), 3.74 (s, 3H), 4.12 (dt, 1H, J=6, 7 Hz), 4.9–5.2 (m, 2H), 5.5–5.9 (m, 1H)

Preparation 14

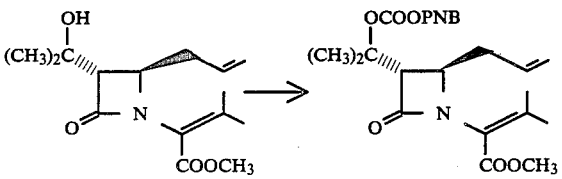

A solution of n-butyl lithium (0.42 ml of 1.55M solution in hexane) was added to a solution of methyl 2-[(3S,4R)-3-(1-hydroxy-1-methylethyl)-2-oxo-4-allylazetidin-1-yl]-3-methylbut-2-enoate (150 mg) in tetrahydrofuran (3 ml) during 3 minutes at −70° C. and the mixture was stirred for 5 minutes at −70° C. A solution of p-nitrobenzyl chloroformate (161 mg) in tetrahydrofuran (1.6 ml) was added to the mixture during 5 minutes at −70° C. and the mixture was stirred for 15 minutes at −70° C. The mixture was allowed to warm to 0° C. during 30 minutes and stirred for 2 hours at 0° C. Acetic acid (0.037 ml) was added to the mixture at 0° C. and the mixture was evaporated in vacuo. The residue was dissolved in ethyl acetate (50 ml), and the sodium was washed with water (10 ml), 10% phosphoric acid (10 ml), phosphate buffer (pH 7.0) (10 ml×2), aqueous sodium bicarbonate and brine. The organic layer was dried over magnesium sulfate and evaporated in vacuo. The residue was chromatographed on silica gel (10 g) eluting with a mixture of hexane and ethyl acetate (5:1–1:1) to give methyl 3-methyl-2-[(3S,4R)-3-[1-methyl-1-(4-nitrobenzyloxycarbonyloxy)ethyl]-2-oxo-4-allylazetidin-1-yl]but-2-enoate (135 mg) as an oil.

IR (CH$_2$Cl$_2$): 1740, 1710, 1520, 1345 cm$^{-1}$.

NMR (CDCl$_3$) δ: 1.66 (s, 3H), 1.69 (s, 3H), 1.97 (s, 3H), 2.19 (s, 3H), 2.2–2.5 (m, 2H), 3.40 (d, 1H, J=2.5 Hz), 3.71 (s, 3H), 4.03 (dt, 1H, J=2.5, 6.5 Hz), 4.9–5.2 (m, 2H), 5.19 (s, 2H), 5.5–5.9 (m, 1H), 7.90 (A$_2$B$_2$, 4H, J=9 Hz).

Preparation 15

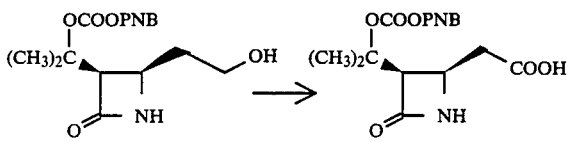

Pyridinium dichromate (3.74 g) was added to a solution of (3R,4R)-4-(2-hydroxyethyl)-3-[1-methyl-1-(4-nitrobenzyloxycarbonyloxy)ethyl]-2-oxo-azetidine (1.00 g) in N,N-dimethylformamide (20 ml) at 0° C., and the stirring mixture was allowed to warm to ambient temperature. After stirring at ambient temperature for 16 hours, the reaction mixture was poured into a mixture of ethyl acetate (150 ml), 10% aqueous sodium bisulfite (40 ml) and 3N hydrochloric acid (15 ml). The organic layer was separated and the remaining aqueous layer was extracted with ethyl acetate (100 ml×2). The organic layers were combined, washed in turn with water and an aqueous sodium chloride, dried over magnesium sulfate, and evaporated in vacuo.

The residue was dissolved in chloroform (30 ml) and the resultant solution was extracted with 5% aqueous sodium bicarbonate (20 ml), 2.5% aqueous sodium bicarbonate (20 ml) and then water (15 ml×2). The aqueous solutions were combined and acidified with 3N hydrochloric acid, followed by re-extraction three times with chloroform (20 ml). The combined extracts were washed with an aqueous sodium chloride, dried over magnesium sulfate, and evaporated to give [(2R,3R)-3-{1-methyl-1-(4-nitrobenzyloxycarbonyloxy)ethyl}-4-oxo-azetidin-2-yl]acetic acid (810 mg).

IR(CH$_2$Cl$_2$): 1735, 1520, 1350 cm$^{-1}$.

Preparation 16

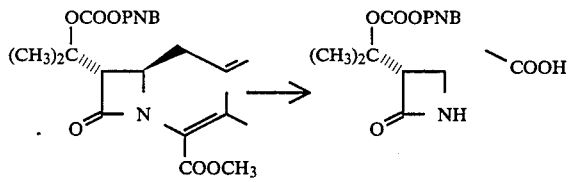

Ozone was bubbled into a solution of methyl 3-methyl-2-[(3S,4R)-3-{1-methyl-1-(4-nitrobenzyloxycarbonyloxy)ethyl}-2-oxo-4-allylazetidin-1-yl]but-2-enoate (50 mg) in ethyl acetate (3 ml) at −70° C. until a blue color appeared. After stirring for 15 minutes at the same temperature, the mixture was purged with nitrogen. The reaction mixture was diluted with ethyl acetate (20 ml) and the solution was washed with an aqueous solution of sodium bisulfite and sodium sulfite (2:1), and brine. The organic layer was dried over magnesium sulfate and evaporated in vacuo. The residue was dissolved in methylene chloride (3 ml) and m-chloroperbenzoic acid (48 mg) was added to the solution at 0° C. The mixture was stirred for 24 hours at ambient temperature. Additional m-chloroperbenzoic acid (48 mg) was added, and the mixture was stirred for 24 hours at ambient temperature. The mixture was evaporated in vacuo. The residue was dissolved in methanol (3 ml) and the mixture was heated for 24 hours at 50° C. The mixture was evaporated in vacuo and the residue was chromatographed on silica gel (4 g) eluting with a mixture of methylene chloride and methanol (20:1–5:1) to give [(2R,3S)-3-{1-methyl-1-(4-nitrobenzyloxycarbonyloxy)ethyl}-4-oxoazetidin-2-yl]acetic acid (43 mg) as an oil.

IR (CH$_2$Cl$_2$): 1740, 1520, 1350 cm$^{-1}$.

NMR (CDCl$_3$) δ: 1.60 (broad s, 6H), 2.3–2.8 (m, 2H), 3.36 (broad s, 1H), 3.7–4.0 (m, 1H), 5.16 (s, 2H), 7.1–7.3 (broad, 1H), 7.84 (A$_2$B$_2$, 4H, J=8 Hz), 9.1–9.6 (broad, 1H).

Preparation 17

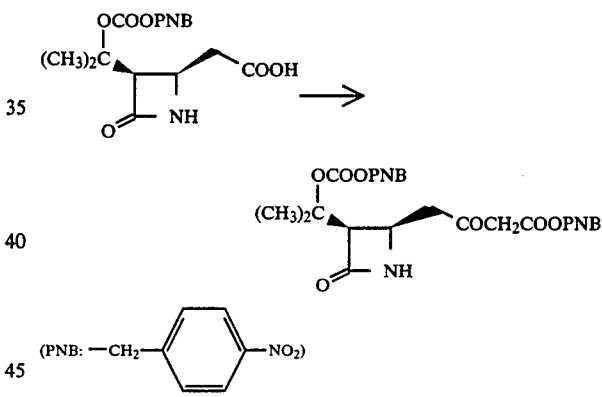

N,N'-Carbonyldiimidazole (540 mg) was added to a solution of [(2R,3R)-3-{1-methyl-1-(4-nitrobenzyloxycarbonyloxy)ethyl]-4-oxoazetidin-2-yl]acetic acid (1.06 g) in tetrahydrofuran (50 ml) at ambient temperature. After stirring for 7 hours at the same temperature, magnesium salt of mono-p-nitrobenzyl malonate (1.45 g) was added thereto, and the resultant mixture was stirred overnight at ambient temperature, The solvent was distilled off in vacuo. The residue was dissolved in ethyl acetate (100 ml) and filtered. The filtrate was washed in turn with 0.1N hydrochloric acid, water, saturated aqueous sodium chloride, aqueous sodium bicarbonate, water, saturated aqueous sodium chloride, 5% aqueous citric acid, water and saturated aqueous sodium chloride. After drying over magnesium sulfate, the solution was evaporated. The residue was chromatographed on silica gel (30 g) eluting with a mixture of methylene chloride and ethyl acetate (50:1 to 2:1) to give formy substance, which was crystallized from a mixture of chloroform and diisopropyl ether, washed with diisopropyl ether and then dried in vacuo to give 4-nitrobenzyl 4-[(2R,3R)-3-{1-methyl-1-(4-nitrobenzyloxycarbonyloxy)ethyl}-4-oxoazetidin-2-yl]-3-oxobutanoate (1.31 g), mp 123°–125° C. (dec.).

IR (CH₂Cl₂): 3400, 1760, 1750, 1720, 1525, 1350 cm⁻¹.

NMR (acetone-d₆) δ: 1.64 (s, 3H), 1.74 (s, 3H), 3.35 (d, 2H, J=6.5 Hz), 3.65 (d, 1H, J=6 Hz), 3.74 (s, 2H), 4.20 (m, 1H), 5.28 (s,2H) 5.31 (s, 2H), 7.18 (s, 1H), 7.93 (A₂B₂, 8H, J=8 Hz).

Preparation 18

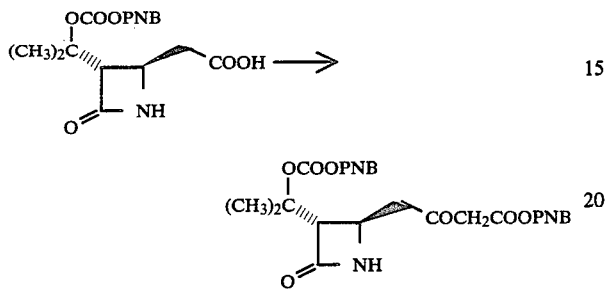

To a solution of [(2R,3S)-3-{1-methyl-1-(4-nitrobenzyloxycarbonyloxy)ethyl}-4-oxoazetidin-2-yl]-acetic acid (56.4 mg) in tetrahydrofuran (1.13 ml) was added N,N'-carbonyldiimidazole (27.5 mg) at ambient temperature. After stirring for 6 hours at ambient temperature, the magnesium salt of the mono-p-nitrobenzyl ester of malonic acid (84.8 mg) was added and the resulting mixture was stirred overnight at ambient temperature. The solvent was distilled off and the residue was dissolved in ethyl acetate (30 ml) and filtered with a diatomaceous earth. The filtrate was washed with 1N hydrochloric acid, water, phosphate buffer solution (pH 6.8), and saturated aqueous sodium chloride. After drying over magnesium sulfate, the ethyl acetate extract was filtered and evaporated in vacuo. The residual oil (78.8 mg) was chromatographed on silica gel (1.6 g) eluting with a mixture of methylene chloride and ethyl acetate (10:1 to 2:1) to give 4-nitrobenzyl 4-[(2R,3S)-3-{1-methyl-1-(4-nitrobenzyloxycarbonyloxy)ethyl}-4-oxoazetidin-2-yl]-3-oxobutanoate (64.2 mg) as an amorphous solid.

IR (CH₂Cl₂): 3380, 1760, 1740, 1720, 1520, 1340 cm⁻¹.

NMR (CDCl₃) δ: 1.62 (s, 3H), 1.66 (s, 3H), 2.86–3.12 (m, 2H), 3.41 (d, 1H, J=2 Hz), 3.65 (s, 2H), 3.94–4.18 (m, 1H), 5.25 (s, 2H), 5.34 (s, 2H), 6.60 (broad s, 1H), 7.63 (d, 4H, J=9 Hz), 8.30 (d, 4H, J=9 Hz).

Preparation 19

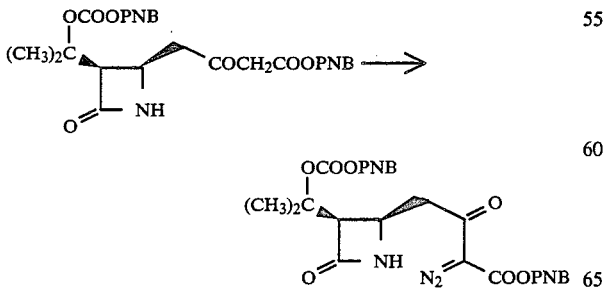

A solution of p-toluenesulfonyl azide (435 mg) in acetonitrile (3.9 ml) was added to a solution of 4-nitrobenzyl 4-[(2R,3R)-3-{1-methyl-1-(4-nitrobenzyloxycarbonyloxy)ethyl}-4-oxoazetidin-2-yl]-3-oxobutanone (1.00 g) in acetonitrile (20 ml) at 0° C. After stirring at 0° C. for 5 minutes, triethylamine (0.923 ml) was added dropwise thereto. After stirring at 0° C. for additional 20 minutes, the reaction mixture was evaporated. The residue was chromatographed on silica gel (20 g) eluting with a mixture of n-hexane and ethyl acetate (10:1 to 1:4) to give 4-nitrobenzyl 2-diazo-4-[(2R,3R)-3-{1-methyl-1-(4-nitrobenzyloxycarbonyloxy)ethyl}-4-oxoazetidin-2-yl]-3-oxobutanoate (1.08 g).

IR (CH₂Cl₂): 3400, 2150, 1765, 1750, 1720, 1655, 1525, 1350 cm⁻¹.

NMR (CDCl₃) δ: 1.68 (s, 3H), 1.79 (s, 3H), 3.4–3.7 (m, 2H), 3.46 (d, 2H, J=4.5 Hz), 4.0–4.3 (m, 1H), 5.20 (s, 2H), 5.35 (s, 2H), 6.22 (s, 1H), 7.80 (A₂B₂, 4H, J=12 Hz), 7.85 (A₂B₂, 4H, J=6 Hz).

Preparation 20

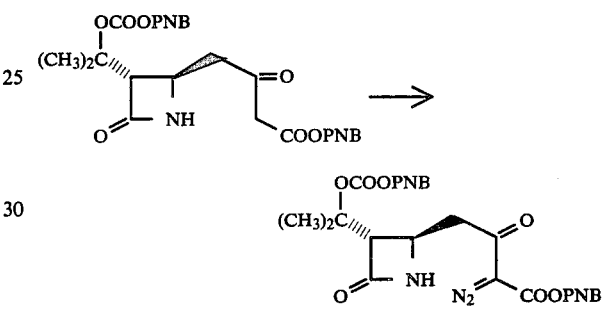

To a solution of 4-nitrobenzyl 4-[(2R,3S)-3-{1-methyl-1-(4-nitrobenzyloxycarbonyloxy)ethyl}-4-oxoazetidin-2-yl]-3-oxobutanoate (58.3 mg) in acetonitrile (1.17 ml) was added a solution of p-toluenesulfonyl azide (25.3 mg) in acetonitrile (0.228 ml) at 0° C. After stirring for 5 minutes at 0° C., a solution of triethylamine (53.7 μl) in acetonitrile (0.483 ml) was added dropwise. The stirring mixture was allowed to warm to ambient temperature during 15 minutes and kept at the same temperature for 20 minutes. The solvent was distilled off and the residue (85.9 mg) was flash-chromatographed on silica gel (1 g) eluting with a mixture of methylene chloride and ethyl acetate (50:1 to 3:1) to give 4-nitrobenzyl 2-diazo-4-[(2R,3S)-3-{1-methyl-1-(4-nitrobenzyloxycarbonyloxy)ethyl}-4-oxoazetidin-2-yl]-3-oxobutanoate (58.4 mg) as an amorphous solid.

IR (CH₂Cl₂): 3380, 2140, 1760, 1740, 1715, 1645, 1520, 1345 cm⁻¹.

NMR (CDCl₃) δ: 1.63 (s, 3H), 1.67 (s, 3H), 2.88–3.34 (m, 2H), 3.46 (d, 1H, J=2 Hz), 3.90–4.20 (m, 1H), 5.26 (s, 2H), 5.45 (s, 2H), 6.48 (broad s, 1H), 7.65 (d, 4H, J=9 Hz), 8.30 (d, 2H, J=9 Hz), 8.34 (d, 2H, J=9 Hz)

Preparation 21

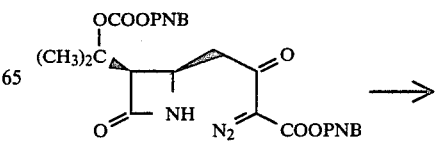

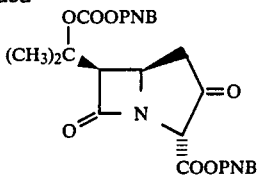

A mixture of 4-nitrobenzyl 2-diazo-4-[(2R,3R)-3-{1-methyl-1-(4-nitrobenzyloxycarbonyloxy)ethyl}-4-oxoazetidin-2-yl]-3-oxobutanoate (1.00 g) and rhodium (II) acetate (5 mg) in benzene (50 ml) was refluxed for 25 minutes. After cooling to ambient temperature, the mixture was filtered through cellulose powder. The filtrate was evaporated to give 4-nitrobenzyl (2R, 5R, 6R)-3,7-dioxo-6-[1-methyl-1-(4-nitrobenzyloxycarbonyloxy)ethyl]-1-azabicyclo[3.2.0]heptane-2-carboxylate (0.94 g) as an amorphous solid.

IR (CH$_2$Cl$_2$): 1770, 1750, 1525, 1350 cm$^{-1}$.

NMR (CDCl$_3$) δ: 1.64 (s, 3H), 1.84 (s, 3H), 2.74 (dd, 1H, J=19 Hz, 8 Hz), 3.34 (dd, 1H, J=19 Hz, 8 Hz), 3.77 (d, 1H, J=6 Hz), 4.34 (dt, 1H, J=6 Hz, 8 Hz), 4.76 (s, 1H), 5.18 (s, 2H), 5.32 (A$_2$B$_2$, 2H, J=16 Hz), 7.88 (A$_2$B$_2$, 4H, J=9 Hz), 7.91 (A$_2$B$_2$, 4H, J=9 Hz).

Preparation 22

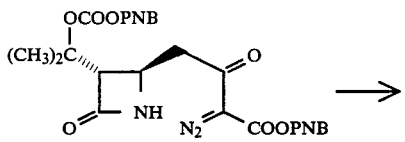

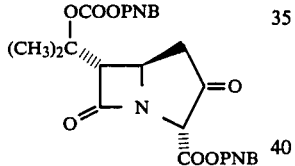

A mixture of 4-nitrobenzyl 2-diazo-4-[(2R,3S)-3-{1-methyl-1-(4-nitrobenzyloxycarbonyloxy)ethyl}-4-oxoazetidin-2-yl]-3-oxobutanoate (58.0 mg) and rhodium (II) acetate (0.1 mg) in benzene (3.4 ml) was refluxed for 30 minutes. After cooling to ambient temperature, the mixture was filtered with a diatomaceous earth and evaporated to give 4-nitrobenzyl (2R,5R,6S)-3,7-dioxo-6-[1-methyl-1-(4-nitrobenzyloxycarbonyloxy)ethyl]-1-azabicyclo[3.2.0]-heptane-2-carboxylate (47.8 mg) as an amorphous solid.

IR (CH$_2$Cl$_2$): 1760, 1735, 1730, 1515, 1345 cm$^{-1}$.

NMR (CDCl$_3$) δ: 1.70 (s, 3H), 2.49 (AB part of ABX system centered at 2.49, 2H, JAB=18 Hz, JAX=JBX=7 Hz), 3.78 (d, 1H, J=2 Hz), 4.21 (dt, 1H, J=2, 7 Hz), 4.79 (s, 1H), 5.21 (s, 2H), 5.30 (ABq, 1H, J=12 Hz), 7.53 (d, 2H, J=9 Hz), 8.22 (d, 2H, J=9 Hz).

Preparation 23

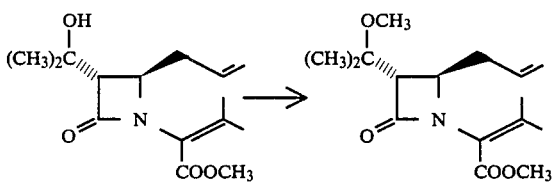

To a solution of methyl-2-[(3S,4R)-3-(1-hydroxy-1-methylethyl)-2-oxo-4-allylazetidin-1-yl]-3-methylbut-2-enoate (2.41 g) in tetrahydrofuran (72.3 ml) was added dropwise a solution of n-butyl lithium (5.41 ml of 1.74M solution in hexane) at −78° C. After stirring for 10 minutes at the same temperature, hexamethylphosphoric triamide (1.64 ml) was added thereto. The resultant solution was stirred for 15 minutes at −78° C. and a solution of dimethyl sulfate (1.62 ml) in tetrahydrofuran (14.6 ml) was added. The mixture was allowed to warm to ambient temperature over a period of 1.5 hours and stirred at ambient temperature overnight. Acetic acid (0.539 ml) was added to the mixture and the solvent was removed by distillation. The residue was dissolved in ethyl acetate (240 ml), and washed with a mixture of 10% aqueous sodium bicarbonate (10 ml) and a saturated aqueous sodium chloride. The aqueous washings were extracted with ethyl acetate and the combined extracts were washed with a saturated aqueous sodium chloride. After drying over magnesium sulfate, the ethyl acetate solution was filtered and evaporated in vacuo. The residue was chromatographed on silica gel (100 g) eluting with a mixture of ethyl acetate and methylene chloride (1:100 to 1:1) to give methyl 2-[(3S,4R)-3-(1-methoxy-1-methylethyl)-2-oxo-4-allylazetidin-1-yl]-3-methylbut-2-enoate (1.66 g) as an oil.

IR (CH$_2$Cl$_2$): 1745, 1720, 1385, 1365 cm$^{-1}$.

NMR (CDCl$_3$) δ: 1.30 (s, 3H), 1.34 (s, 3H), 1.96 (s, 3H), 2.18 (s, 3H), 2.41 (t, 2H, J=7 Hz), 2.97 (d, 1H, J=3 Hz), 3.25 (s, 3H), 3.77 (s, 3H), 4.0 (dt, 1H, J=3, 7 Hz), 4.95–5.4 (m, 2H), 5.5–6.1 (m, 1H).

Preparation 24

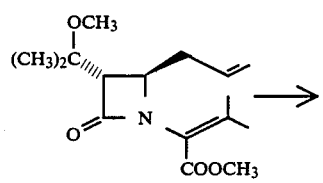

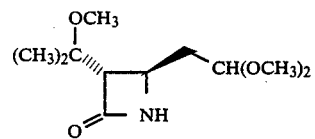

Ozone was passed through a solution of methyl 2-[(3S, 4R)-3-(1-methoxy-1-methylethyl)-2-oxo-4-allylazetidin-1-yl[-3-methylbut-2-enoate (1.45 g) in methanol (87 ml) at −78° C. over a period of 50 minutes. The resultant blue solution was babbled with nitrogen for 20 minutes, and dimethyl sulfide (14.5 ml) was added to the mixture. The mixture was allowed to warm to −20° C. over a period of 20 minutes, stored at −20° C. for 2 hours and at 0° C. for additional 4 hours, followed by allowing to stand at ambient temperature overnight. Trimethyl orthoformate (7.25 ml) and p-toluenesulfonic acid monohydrate (93.3 mg) were added and the resultant mixture was stirred for an hour at 50° C. After cooling to 0° C., pyridine (40.4 μl) was added thereto. After concentration, the residue was dissolved in ethyl acetate (100 ml) and then washed with a mixture of 1N hydrochloric acid (0.5 ml) and a saturated aqueous sodium chloride. The aqueous washings were extracted with ethyl acetate (50 ml) and the combined extracts were washed with a mixture of 10% aqueous sodium bicarbonate and a saturated aqueous sodium chloride, and a saturated aquueous sodium chloride in turn. After drying over magnesium sulfate, the ethyl acetate extract was filtered and evaporated in vacuo. The residue was dissolved in methanol (43.5 ml) and sodium methoxide (4.9M 0.15 ml) was added at 0° C. After stirring for 30 minutes at 0° C., acetic acid (42.2 ml) was added, and then the solvent was distilled off in vacuo. The residue was chromatographed on silica gel (30 g) eluting with a mixture of methylene chloride and ethyl acetate (20:1 to 1:2) to give (3S, 4R)-4-(2,2-dimethoxyethyl)-3-(1-methoxy-1-methylethyl)azetidin-2-one (1.03 g) as an oil.

IR (CH₂Cl₂): 3400, 1755, 1365, 1130, 1070 cm⁻¹.

Preparation 25

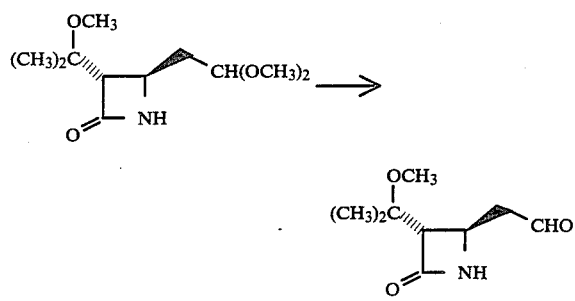

A solution of (3S, 4R)-4-(2,2-dimethoxyethyl)-3-(1-methoxy-1-methylethyl)azetidin-2-one (1.03 g) in 80% aqueous acetic acid (50 ml) was stirred at 50° C. for 4 hours, and the solution was evaporated in vacuo. The residue was dissolved in toluene (8 ml) and evaporated in vacuo to give (3S, 4R)-3-(1-methoxy-1-methylethyl)-4-(2-oxoethyl)azetidin-2-one (760 mg) as an oil.

IR (CH₂Cl₂): 3410, 2930, 1755, 1725, 1380, 1365, 1070 cm⁻¹.

Preparation 26

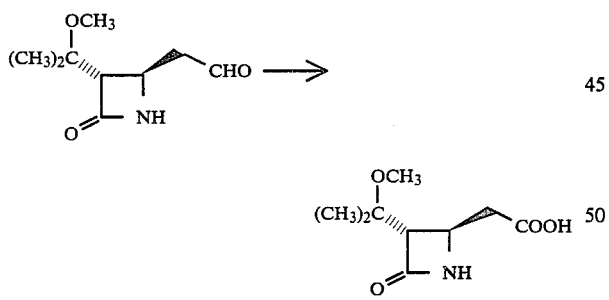

To a solution of (3S, 4R)-3-(1-methoxy-1-methylethyl)-4-(2-oxoethyl)azetidin-2-one (760 mg) in acetone (60 ml) was added dropwise 2N Jones Reagent (4.10 ml) at 0° C. After stirring for 30 minutes at 0° C., isopropyl alcohol (8 ml) was added to the resultant mixture, and then evaporated in vacuo. The residue was dissolved in a saturated aqueous sodium chloride (40 ml) and extracted with chloroform (80 ml×5). After drying over magnesium sulfate, the chloroform extracts were filtered and evaporated in vacuo. The residue was chromatographed on silica gel (30 g) eluting with a mixture of methylene chloride and methanol (10:1 to 1:2), and then a mixture of acetic acid and ethyl acetate (1:50) to give 2-[(2R, 3S)-3-(1-methoxy-1-methylethyl)-4-oxoazetidin-2-yl]acetic acid (545.1 mg) as an amorphous solid.

IR (CH₂Cl₂): 3400, 2940, 1760, 1735, 1385, 1370, 1070 cm⁻¹.

NMR (D₂O) δ: 1.27 (s, 6H), 2.50-3.50 (m, 2H), 2.76 (d, 1H, J=3 Hz), 3.21 (s, 3H), 3.92 (dt, 1H, J=3, 7 Hz).

Preparation 27

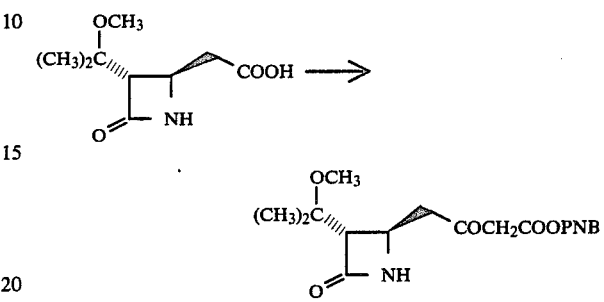

To a solution of 2-[(2R, 3S)-3-(1-methoxy-1-methylethyl)-4-oxoazetidin-2-yl]acetic acid (65.6 mg) in tetrahydrofuran (3.25 ml) was added carbonyldiimidazole (58.1 mg) at ambient temperature. After stirring for 6 hours at ambient temperature, magnesium salt of mono-p-nitrobenzyl malonate (179.7 mg) was added thereto and the resultant mixture was stirred overnight at ambient temperature. The solvent was distilled off and the residue was dissolved in ethyl acetate (10 ml) and filtered. The filtrate was washed in turn with 1N hydrochloric acid, water, 10% aqueous sodium bicarbonate, water, 5% aqueous citric acid, water and a saturated aqueous sodium chloride. After drying over magnesium sulfate, the ethyl acetate extract was filtered and evaporated in vacuo. The residue (101.2 mg) was chromatographed on silica gel (2 g) eluting with a mixture of methylene chloride and acetone (80:1 to 4:1) to give 4-nitrobenzyl 4-[(2R, 3S)-3-(1-methoxy-1-methyl-ethyl)-4-oxoazetidin-2-yl]-3-oxobutanoate (71.0 mg) as an amorphous solid.

IR (CH₂Cl₂): 1755, 1715, 1600, 1520, 1345 cm⁻¹.

NMR (CDCl₃) δ: 1.26 (s, 3H), 1.29 (s, 3H), 2.5-3.4 (m, 2H), 2.87 (d, 1H, J=3 Hz), 3.2 (s, 3H), 3.59 (s, 2H), 3.91 (dt, 1H, J=3, 7 Hz), 5.29 (s, 2H), 6.16 (broad s, 1H), 7.56 (d, 2H, J=9 Hz), 8.26 (d, 2H, J=9 Hz).

Preparation 28

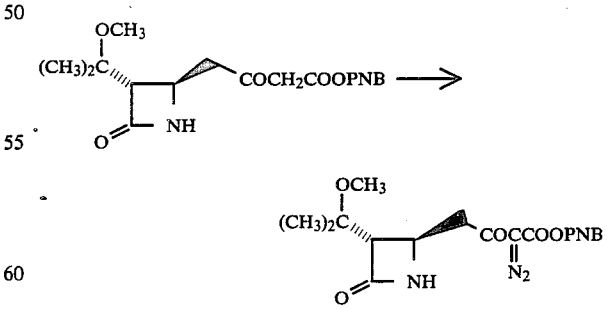

To a solution of 4-nitrobenzyl 4-[(2R, 3S)-3-(1-methoxy-1-methylethyl)-4-oxoazetidine-2-yl]-3-oxobutanoate (61.2 mg) in acetonitrile (1.22 ml) was added a solution of p-toluenesulfonyl azide (38.3 mg) in acetonitrile (0.345 ml) at 0° C. After stirring for 10 minutes at 0° C., a solution of triethylamine (81.3 μl) in acetonitrile (0.732 ml) was added dropwise at 0° C. After the resultant solution was stirred for 30 minutes at 0° C., the solvent was distilled off, and the residue was flash-chromatographed on silica gel (0.9 g) eluting with a mixture of methylene chloride and ethyl acetate (40:1 to 3:1) to give 4-nitrobenzyl 2-diazo-4-[(2R, 3S)-3-(1-methoxy-1-methylethyl)-4-oxoazetidin-2-yl]-3-oxobutanoate (56.5 mg) as an amorphous solid.

IR (CH$_2$Cl$_2$): 3400, 2150, 1760, 1720, 1650, 1610, 1530, 1350 cm$^{-1}$.

NMR (CDCl$_3$) δ: 1.26 (s, 3H), 1.30 (s, 3H), 2.6–3.5 (m, 2H), 2.95 (d, 1H, J=3 Hz), 3.2 (s, 3H), 3.97 (dt, 1H, J=3, 7 Hz), 5.37 (s, 2H), 6.15 (broad s, 1H), 7.55 (d, 2H, J=8 Hz), 8.25 (d, 2H, J=8 Hz).

Preparation 29

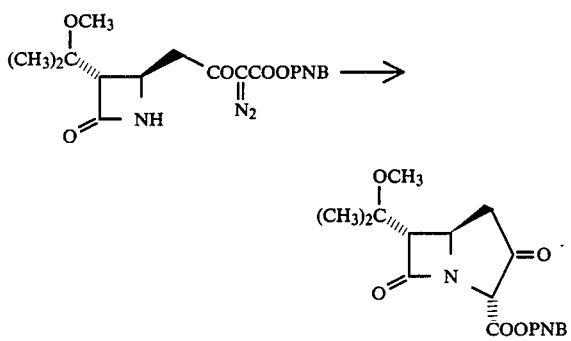

A mixture of 4-nitrobenzyl 2-diazo-4-[(2R, 3S)-3-(1-methoxy-1-methylethyl)-4-oxo-azetidin-2-yl]-3-oxobutanoate (56.5 mg) and a catalytic amount of rhodium (II) acetate (ca. 1 mg) in dry benzene (5.6 ml) was refluxed for 30 minutes. After cooling to ambient temperature, the mixture was filtered and evaporated in vacuo to give 4-nitrobenzyl (2R, 5R, 6S)-3,7-dioxo-6-(1-methoxy-1-methylethyl)-1-azabicyclo[3.2.0]-heptane-2-carboxylate (50.0 mg) as an amorphous solid.

IR (CH$_2$Cl$_2$): 1770, 1750, 1605, 1525, 1350 cm$^{-1}$.

NMR (CDCl$_3$) δ: 1.33 (s, 3H), 1.37 (s, 3H), 2.4 (dd, 1H, J=8, 18 Hz), 2.93 (dd, 1H, J=8, 18 Hz), 3.2 (d, 1H, J=3 Hz), 3.25 (s, 3H), 4.1 (dt, 1H, J=3 and 8 Hz), 4.72 (s, 1H), 5.34 (s, 2H), 7.45 (d, 2H, J=9 Hz), 8.14 (d, 2H, J=9 Hz).

Preparation 30

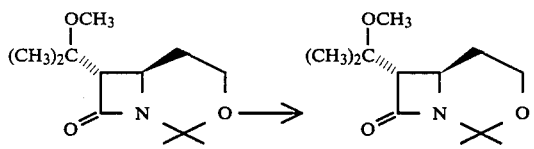

To a suspension of sodium hydride (38.1 mg, 50% in mineral oil) in N,N-dimethylformamide (1.14 ml) was added dropwise a solution of (6R, 7S)-2,2-dimethyl-7-(1-hydroxy-1-methylethyl)-1-aza-3-oxabicyclo[4.2.0]-octan-8-one (84.6 mg) in N,N-dimethylformamide (25.4 ml) at 0° C. After stirring for 30 minutes at 0° C., thereto was added a solution of dimethyl sulfate (75.13 μl) in N,N-dimethylformamide (0.676 ml), and the resultant mixture was stirred for 3 hours at 0° C. and for additional 1.5 hours at ambient temperature. Acetic acid (0.046 ml) was added to the mixture, and the solvent was distilled off in vacuo. The residue was diluted with ethyl acetate (20 ml) and then washed with an aqueous sodium chloride, 10% aqueous sodium bicarbonate, and a saturated aqueous sodium chloride in turn. The aqueous washings were extracted with ethyl acetate, and this extract was washed with an aqueous sodium chloride. The combined extracts were dried over magnesium sulfate, filtered and evaporated in vacuo. The residue (92.9 mg) was chromatographed on silica gel (2.5 g) eluting with a mixture of ethyl acetate and methylene chloride (1:100 to 1:3) to give (6R, 7S)-2,2-dimethyl-7-(1-methoxy-1-methylethyl)-1-aza-3-oxabicyclo[4.2.0]-octan-8-one (69.1 mg) as a pale yellow solid.

IR (CH$_2$Cl$_2$): 1745, 1370, 1350, 1070, 1060 cm$^{-1}$.

NMR (CDCl$_3$) δ: 1.26 (s, 6H), 1.40 (s, 3H), 1.6–2.0 (m, 2H), 1.77 (s, 3H), 2.89 (d, 1H, J=3 Hz), 3.20 (s, 3H), 3.58 (ddd, 1H, J=3, 6, 9 Hz), 3.86 (dd, 2H, J=3, 7 Hz).

Preparation 31

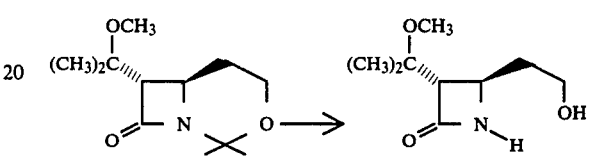

A solution of (6R, 7S)-2,2-dimethyl-7-(1-methoxy-1-methylethyl)-1-aza-3-oxabicyclo[4.2.0]octan-8-one (142.3 mg) in a mixture of acetic acid (2.28 ml) and water (0.57 ml) was heated at 65° C. for 1.5 hours. The mixture was cooled to ambient temperature and then evaporated in vacuo. Xylene was added to the residue and the resultant suspension was evaporated in vacuo. The residue was dissolved in a mixture of methanol and xylene, and the resultant solution was evaporated in vacuo. This operation was repeated once and the residue was chromatographed on silica gel (1.5 g) eluting with a mixture of methylene chloride and acetone (10:1 to 1:1) to give (3S, 4R)-4-(2-hydroxyethyl)-3-(1-methoxy-1-methylethyl)azetidin-2-one (111.3 mg).

IR (CH$_2$Cl$_2$): 3400, 2930, 1760, 1370, 1060 cm$^{-1}$.

NMR (CDCl$_3$) δ: 1.26 (s, 3H), 1.32 (s, 3H), 1.7–2.0 (m, 2H), 3.06 (d, 1H, J=3 Hz), 3.24 (s, 3H), 3.6–3.9 (m, 3H), 6.5 (broad s, 1H).

Preparation 32

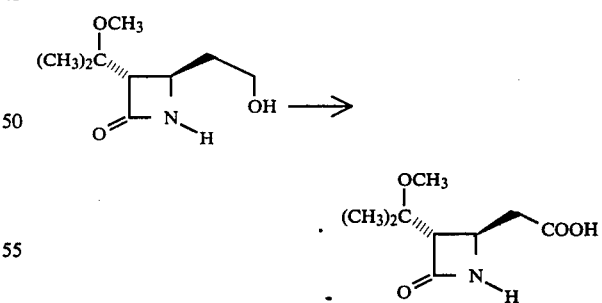

A solution of (3S, 4R)-4-(2-hydroxyethyl)-3-(1-methoxy-1-methylethyl)azetidin-2-one (50.7 mg) in acetone (5.42 ml) was added to a solution of 2N Jones reagent (0.542 ml) in acetone (5.42 ml) at ambient temperature over a period of 30 minutes, and the mixture was stirred for an hour. After addition of an excess of isopropyl alcohol to the mixture, the solvent was removed. The residue was dissolved in chloroform and the resultant solution was washed with a saturated aqueous sodium chloride. The washings were extracted five times with chloroform. The extracts were combined, dried over magnesium sulfate, filtered and evaporated. The crystalline residue was washed with isopropyl alcohol to give 2-[(2R, 3S)-3-(1-methoxy-1-methylethyl)-4-oxoazetidin-2-yl]acetic acid (25.1 mg). The mother liquor was concentrated and the crystalline residue was washed with hexane to give a second crop of the above product (19.4 mg). Total yield is 44.5 mg.

IR (CH$_2$Cl$_2$): 3400, 2940, 1760, 1735, 1385, 1370, 1070 cm$^{-1}$.

Preparation 33

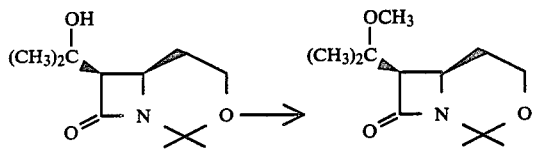

To a solution of (6R, 7R)-2,2-dimethyl-7-(1-hydroxy-1-methylethyl)-1-aza-3-oxabicyclo[4.2.0]octan-8-one (43.0 mg) in tetrahydrofuran (1.29 ml) was added dropwise a solution of n-butyl lithium (0.128 ml of 1.74M solution in hexane) at −78° C. After stirring for 10 minutes at the same temperature, hexamethylphosphoric triamide (38.6 μl) was added to the mixture. The resultant solution was stirred for 10 minutes at −78° C. and a solution of dimethylsulfate (38.2 μl) in tetrahydrofuran (0.344 ml) was added to the mixture. The resultant mixture was allowed to warm to ambient temperature over a period of an hour and stirred at ambient temperature overnight. After acetic acid (12.7 μl) was added, the solvent was distilled off, and the residue was dissolved in ethyl acetate (10 ml) and washed with a mixture of 10% aqueous solution of sodium bicarbonate (0.3 ml) and a saturated aqueous sodium chloride (3 ml). The aqueous washings were extracted with ethyl acetate (10 ml) and the combined ethyl acetate extracts were washed with a saturated aqueous sodium chloride. After drying over magnesium sulfate, the ethyl acetate solution was filtered and evaporated in vacuo. The residue was chromatographed on silica gel (2.2 g) eluting with a mixture of ethyl acetate and methylene chloride (1:100 to 1:1) to give (6R, 7R)-2,2-dimethyl-7-(1-methoxy-1-methylethyl)-1-aza-3-oxabicyclo[4.2.0]octan-8-one (24.0 mg) as a white solid.

IR (CH$_2$Cl$_2$): 2930, 1740, 1370, 1075 cm$^{-1}$.

NMR (CDCl$_3$) δ: 1.21 (s, 3H), 1.37 (s, 3H), 1.39 (s, 3H), 1.5–1.8 (m, 1H), 1.74 (s, 3H), 2.3–3.0 (m, 1H), 3.16 (d, 1H, J=5 Hz), 3.25 (s, 3H), 3.5–4.0 (m, 1H), 3.87 (dd, 2H, J=3, 10 Hz).

Preparation 34

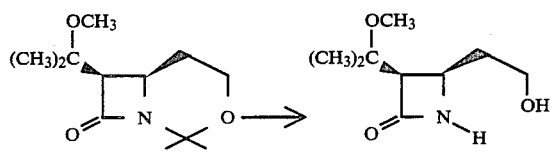

A solution of (6R, 7R)-2,2-dimethyl-7-(1-methoxy-1-methylethyl)-1-aza-3-oxabicylco[4.2.0]octan-8-one (345 mg) in a mixture of acetic acid (5.52 ml) and water (1.38 ml) was heated at 65° C. for 30 minutes. The mixture was cooled to ambient temperature and evaporated in vacuo. Xylene was added to the residue and the resultant suspension was evaporated in vacuo. The crystalline residue was dissolved in a mixture of methanol and xylene and the resultant solution was evaporated in vacuo. This operation was repeated once, and the crystalline residue was washed with hexane to give (3R, 4R)-4-(2-hydroxyethyl)-3-(1-methoxy-1-methylethyl)azetidin-2-one (275 mg).

IR (CH$_2$Cl$_2$): 3600, 2900, 1750 cm$^{-1}$.

NMR (CDCl$_3$) δ: 1.31 (s, 3H), 1.43 (s, 3H), 2.0–2.2 (m, 2H), 1.60 (broad s, 1H), 3.26 (s, 3H), 3.35 (d, 1H, J=6 Hz), 3.6–4.0 (m, 3H), 6.66 (broad s, 1H).

Preparation 35

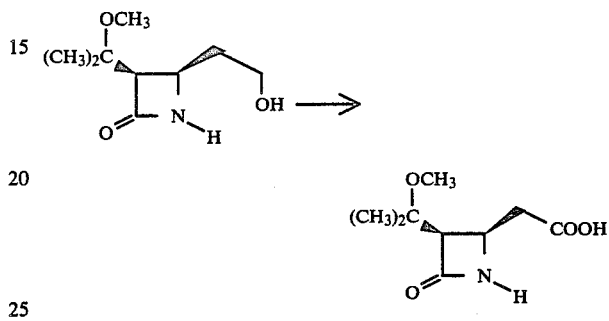

A solution of (3R, 4R)-4-(2-hydroxyethyl)-3-(1-methoxy-1-methylethyl)azetidin-2-one (250 mg) in acetone (26.7 ml) as added to a solution of 2N Jones reagent (2.67 ml) in acetone (24.03 ml) at ambient temperature over a period of 40 minutes and the mixture was stirred for another 40 minutes. After addition of an excess of isopropyl alcohol to the mixture, the solvent was distilled off. The residue was dissolved in chloroform and washed with a saturated aqueous sodium chloride. The aqueous layer was extracted four times with chloroform. The extracts were combined, dried over magnesium sulfate, filtered and evaporated. The crystalline residue was washed with hexane to give 2-[(2R, 3R)-3-(1-methoxy-1-methylethyl)-4-oxoazetidin-2-yl]acetic acid (211 mg).

IR (Nujol): 3280, 3200, 1730, 1710 cm$^{-1}$.

NMR (D$_2$O) δ: 1.25 (s, 3H), 1.36 (s, 3H), 2.98 (d, 2H, J=7 Hz), 3.22 (s, 3H), 3.54 (d, 1H, J=5 Hz), 4.19 (dt, 1H, J=5, 7 Hz).

Preparation 36

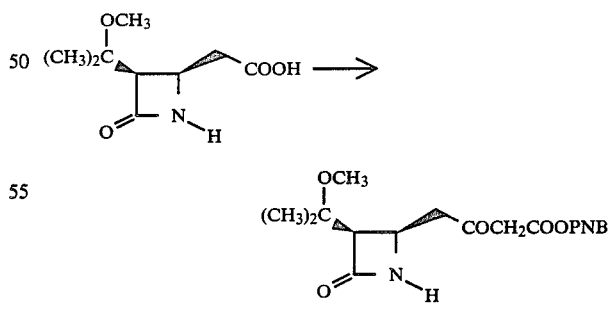

N,N'-Carbonyldiimidazole (487.4 mg) was added to a solution of 2-[(2R, 3R)-3-(1-methoxy-1-methylethyl)-4-oxoazetidin-2-yl]acetic acid (550 mg) in tetrahydrofuran (22 ml) at ambient temperature. After stirring for 5 hours at the same temperature, magnesium salt of mono-p-nitrobenzyl malonate (1.505 g) was added thereto, and the resultant mixture was stirred overnight at ambient temperature. The solvent was distilled off in vacuo.

The residue was dissolved in ethyl acetate and filtered. The filtrate was washed in turn with 0.1N hydrochloric acid, water, 10% aqueous sodium bicarbonate, water, 5% aqueous citric acid, water and saturated aqueous sodium chloride. After drying over magnesium sulfate, the solution was filtered and evaporated. The residue was chromatographed on silica gel (25 g) eluting with a 0–50% mixture of ethyl acetate in methylene chloride to give 4-nitrobenzyl 4-[(2R, 3R)-3-(1-methoxy-1-methylethyl)-4-oxazetidin-2-yl]-3-oxobutanoate (775 mg).

IR (CH$_2$Cl$_2$): 3400, 3020, 1760, 1720, 1610, 1520, 1350 cm$^{-1}$.

NMR (CDCl$_3$) δ: 1.24 (s, 3H), 1.44 (s, 3H), 3.23 (s, 3H), 3.2–3.4 (m, 3H), 3.62 (s, 2H), 4.0–4.2 (m, 1H), 5.32 (s, 2H), 6.20 (broad s, 1H), 7.60 (d, 2H, J=8 Hz), 8.30 (d, 2H, J=8 Hz).

Preparation 37

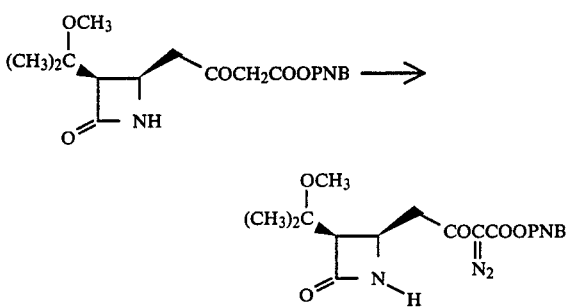

A solution of p-toluenesulfonyl azide (470 mg) in acetonitrile (4.23 ml) was added to a solution of 4-nitrobenzyl 4-[(2R,3R)-3-(1-methoxy-1-methylethyl)-4-oxoazetidin-2-yl]-3-oxobutanoate (752 mg) in acetonitrile (15.04 ml) at 0° C. After stirring at 0° C. for 10 minutes, a solution of triethylamine (0.997 ml) in acetonitrile (8.973 ml) was added dropwise thereto. After stirring at 0° C. for an additional 50 minutes, the reaction mixture was evaporated. The residue was chromatographed on silica gel (11 g) eluting with 0–50% ethyl acetate in methylene chloride to give 4-nitrobenzyl 2-diazo-4-[(2R,3R)-3-(1-methoxy-1-methylethyl)-4-oxoazetidin-2-yl]-3-oxobutanoate (733 mg).

IR (CH$_2$Cl$_2$): 3400, 2930, 2150, 1760, 1720, 1650, 1610, 1530, 1350 cm$^{-1}$.

NMR (CDCl$_3$) δ: 1.27 (s, 3H), 1.44 (s, 3H), 3.26 (s, 3H), 3.35 (d, 1H, J=7 Hz), 3.58 (m, 2H), 4.16 (m, 1H), 5.42 (s, 2H), 6.23 (broad s, 1H), 7.62 (d, 2H, J=9 Hz), 8.33 (d, 2H, J=9 Hz).

Preparation 38

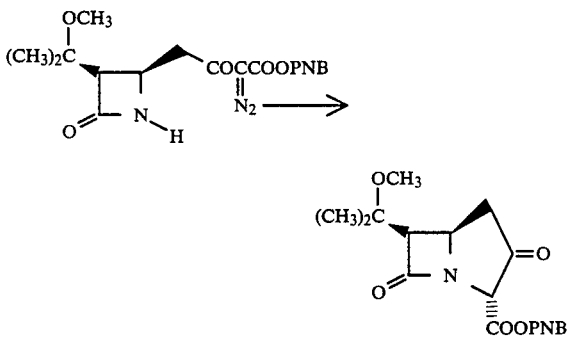

A mixture of 4-nitrobenzyl 2-diazo-4-[(2R,3R)-3-(1-methoxy-1-methylethyl)-4-oxoazetidin-2-yl]-3-oxobutanoate (707 mg) and rhodium (II) acetate (ca. 5 mg) in benzene (20 ml) was refluxed for 30 minutes. After cooling to ambient temperature, the mixture was filtered through cellulose powder. The filtrate was evaporated to give 4-nitrobenzyl (2R,5R,6R)-3,7-dioxo-6-(1-methoxy-1-methylethyl)-1-azabicyclo[3.2.0]heptane-2-carboxylate (680 mg).

IR (CH$_2$Cl$_2$): 1770, 1750, 1610, 1520, 1350 cm$^{-1}$.

NMR (CDCl$_3$) δ: 1.25 (s, 3H), 1.46 (s, 3H), 2.60 (dd, 1H, J=7, 19 Hz), 3.18 (s, 3H), 3.64 (d, 1H, J=5 Hz), 3.96 (dd, 1H, J=7, 19 Hz), 4.18 (dt, 1H, J=5, 7 Hz), 4.68 (s, 1H), 5.30 (ABq, 2H, J=16 Hz), 7.60 (d, 2H, J=8 Hz), 8.26 (d, 2H, J=8 Hz).

Preparation 39

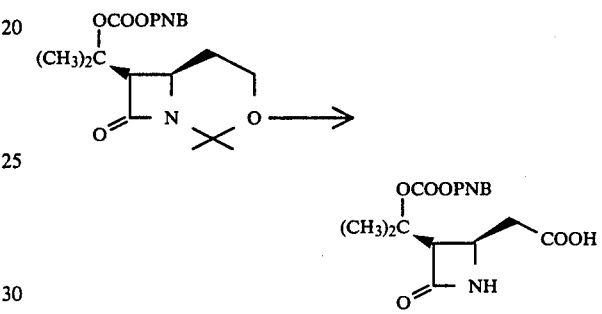

A solution of (6R,7R)-2,2-dimethyl-7-[1-methyl-1-(4-nitrobenzyloxycarbonyloxy)ethyl]-1-aza-3-oxabicyclo[4.2.0]octan-8-one (11.99 g) in acetone (119.9 ml) was added dropwise to a solution of 2N Jones reagent (38.13 ml) in acetone (119.9 ml) at ambient temperature over a period of an hour, and the mixture was stirred for an additional 30 minutes. After addition of an excess of isopropyl alcohol to the mixture, the solvent was removed by evaporation. The residue was dissolved in ethyl acetate (1 l) and the solution was washed with water. The aqueous washings were extracted with ethyl acetate (200 ml). The organic layers were combined, washed with an aqueous sodium chloride, dried over magnesium sulfate, and evaporated to give 2-[(2R,3R)-3-[1-methyl-1-(4-nitrobenzyloxycarbonyloxy)ethyl]-4-oxo-azetidin-2-yl]acetic acid (11.8 g).

IR (CH$_2$Cl$_2$): 1735, 1520, 1350 cm$^{-1}$.

Preparation 40

A solution of N,N-diisopropyl-N-ethylamine (0.0474 ml) in N,N-dimethylformamide (0.426 ml) and benzyl N-(4-nitrobenzyloxycarbonyl)acetimidate (89.4 mg) were added to a solution of 5-aminomethyl-1,3,4-thiadiazole-4-thiol hydrochloride (50 mg) in N,N-dimethylformamide (1 ml) at ambient temperature and the mixture was stirred at the same temperature for 6 hours and allowed to stand at 5° C. for 2 days. The mixture was evaporated in vacuo and the residue was dissolved in ethyl acetate (20 ml), washed with water, dried over magnesium sulfate, and evaporated in vacuo. The crystalline residue was washed with methylene chloride and filtered to give 5-[N-{N-(4-nitrobenzyloxycarbonyl)acetimidoyl}-aminomethyl]-1,3,4-thiadiazole-2-thiol (67 mg) as yellow powder.

IR (Nujol): 3370, 1680, 1340 cm$^{-1}$.

NMR (DMSO-d6) δ: 2.13 (s, 3H), 3.0–3.8 (broad s, 1H) 4.50 (broad s, 2H), 5.20 (s, 2H), 7.62 (d, 2H, J=9 Hz), 8.22 (d, 2H, J=9 Hz), 8.73 (broad s, 1H).

Preparation of the object compounds (I)

EXAMPLE 1

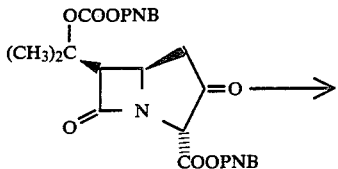

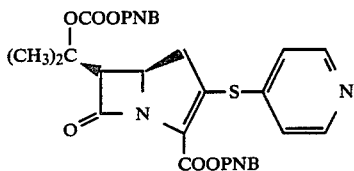

To a solution of 4-nitrobenzyl(2R,5R,6R)-3,7-dioxo-6-[1-methyl-1-(4-nitrobenzyloxycarbonyloxy)ethyl]-1-azabicyclo[3.2.0]heptane-2-carboxylate (940 mg) and 4-(N,N-dimethylamino)pyridine (21.2 mg) in acetonitrile (50 ml) was added a solution of N,N-diisopropyl-N-ethylamine (0.363 ml) in acetonitrile (3.30 ml) at 0° C., followed by a solution of diphenyl-chlorophosphate (0.378 ml) in acetonitrile (3.40 ml) at 0° C. After stirring at 0° C. for an hour, the reaction mixture was cooled to −15° C., and thereto was added a solution of N,N-diisopropyl-N-ethylamine (1.21 ml) in acetonitrile (11.0 ml), followed by 4-mercaptopyridine (212 mg).

After standing overnight at −15° C., the mixture was evaporated in vacuo. The residue was dissolved in ethyl acetate (100 ml) and the solution was washed successively with water and saturated aqueous sodium chloride, dried over magnesium sulfate, and then evaporated in vacuo. The residue was chromatographed on silica gel containing 10% water (23 g). Elution was carried out with a mixture of benzene and acetone (10:1 to 3:1), and the residue was crystallized from a mixture of acetone and diethyl ether to give 4-nitrobenzyl(5R,6R)-3-(4-pyridylthio)-6-[1-methyl-1-(4-nitrobenzyloxycarbonyloxy)ethyl]-7-oxo-1-azabicyclo-[3.2.0]hept-2-ene-2-carboxylate (621 mg), mp 165°–166° C. (dec.).

IR (CH2Cl2): 1785, 1750, 1710, 1610, 1520, 1350 cm⁻¹.

NMR (CDCl3) δ: 1.53 (s, 3H), 1.80 (s, 3H), 1.70 (dd, 1H, J=18 Hz, 10 Hz), 3.50 (dd, 1H, J=18 Hz, 10 Hz), 3.72 (d, 1H, J=6.5 Hz), 4.31 (dt, 1H, J=6.5 Hz, 10 Hz), 5.20 (s, 2H), 5.41 (ABq, 2H, J=9 Hz), 7.88 (A2B2, 4H, J=8 Hz), 7.89 (A2B2, 4H, J=5 Hz), 7.97 (A2B2, 4H, J=8 Hz).

EXAMPLE 2

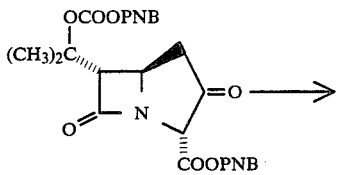

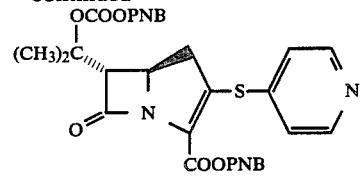

To a solution of 4-nitrobenzyl(2R,5R,6S)-3,7-dioxo-6-[1-methyl-1-(4-nitrobenzyloxycarbonyloxy)ethyl]-1-azabicyclo[3.2.0]heptane-2-carboxylate (145.1 mg) and 4-(N,N-dimethylamino)pyridine (3.27 mg) in acetonitrile (7.3 ml) was added dropwise a solution of N,N-diisopropyl-N-ethylamine (56.0 μl) in acetonitrile (0.504 μl), followed by a solution of diphenyl-chlorophosphate (58.3 μl) in acetonitrile (0.525 ml) at 0° C. After stirring for an hour at 0° C., thereto was added a solution of N,N-diisopropyl-N-ethylamine (186.4 μl) in acetonitrile (1.68 ml), followed by 4-mercaptopyridine (31.3 mg) at −15° C. The mixture was allowed to stand overnight at −15° C. The resultant solution was diluted with ethyl acetate (15 ml) and then washed in turn with water and saturated aqueous sodium chloride. After drying over magnesium sulfate, the solution was filtered and evaporated in vacuo. The residue was chromatographed on silica gel (4 g) eluting with a mixture of benzene and acetone (30:1 to 6:1) to give 4-nitrobenzyl(5R,6S)-3-(4-pyridylthio)-6-[1-methyl-1-(4-nitrobenzyloxycarbonyloxy)ethyl]-7-oxo-1-azabicyclo[3.2.0]hept-2-ene-2-carboxylate (139.1 mg).

IR (CH2Cl2): 1770, 1735, 1730, 1600, 1520, 1350 cm⁻¹.

NMR (CDCl3) δ: 1.65 (s, 6H), 2.89 (d, 2H, J=9 Hz), 3.78 (d, 1H, J=3 Hz), 4.30 (dt, 1H, J=3, 9 Hz), 5.15 (s, 2H), 5.41 (ABq, 2H, J=14 Hz), 7.10–7.82 (m, 6H), 8.00–8.35 (m, 4H), 8.62 (d, 2H, J=4 Hz).

EXAMPLE 3

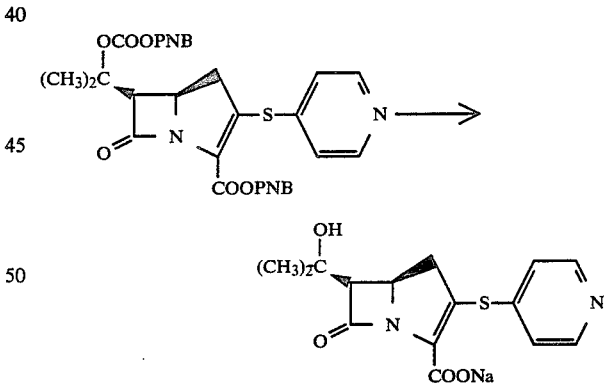

A mixture of 5% palladium on activated charcoal (50 ml), dioxane (3.5 ml) and 1/30M sodium phosphate buffer solution (pH 7.0, 1.5 ml) was shaken for an hour under hydrogen atmosphere (40 psi) at ambient temperature. To this mixture was added a solution of 4-nitrobenzyl(5R,6R)-3-(4-pyridylthio)-6-[1-methyl-1-(4-nitrobenzyloxycarbonyloxy)ethyl]-7-oxo-1-azabicyclo[3.2.0]hept-2-ene-2-carboxylate (43 mg) in a mixture of dioxane (3.5 ml) and 1/30M sodium phosphate buffer solution (pH 7.0, 1.5 ml) at 0° C., and the resultant mixture was shaken under hydrogen atmosphere (40 psi) for 100 minutes, during which time the reaction temperature rose to ambient temperature. After addition of 1% aqueous sodium bicarbonate (0.57 ml) at 0° C., the mixture was filtered through cellulose powder. The filter-cake was washed with water (3×10 ml). The combined filtrates were concentrated to half of the original volume. The concentrate was washed with ethyl acetate (3×20 ml) and evaporated in vacuo. The residue was dissolve in water (60 ml) containing sodium chloride (1.75 g) and then chromatographed on nonionic adsorption resin "Diaion HP-20" (Trade Mark, maker: Mitsubishi Chemical Industries Ltd. (1.5×20 cm) eluting with water (100 ml) and a mixture of water and acetone (10:0 to 7:3, 200 ml). The fractions, whose UV spectra showed λmax 302 nm, were collected and lyophilized to give sodium (5R,6R)-3-(4-pyridylthio)-6-(1-hydroxy-1-methylethyl)-7-oxo-1-azabicyclo[3.2.0]-hept-2-ene-2-carboxylate (13.7 mg) as white powder.

IR (Nujol): 3300, 1750, 1600 cm$^{-1}$.

NMR (D$_2$O) δ: 1.21 (s, 3H), 1.44 (s, 3H), 2.77 (dd, 1H, J=17 Hz, 11 Hz), 3.71 (dd, 1H, J=17 Hz, 11 Hz), 3.76 (d, 1H, J=6 Hz), 4.35 (dt, 1H, J=6 Hz, 11 Hz), 7.95 (A$_2$B$_2$, 4H, J=5 Hz).

UV (H$_2$O): 302 nm (ε=9.922×10$^3$).

EXAMPLE 4

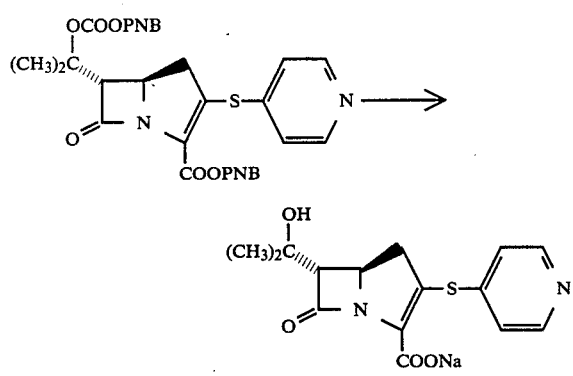

A mixture of 5% palladium on activated charcoal (133 mg), dioxane (14.8 ml) and 1/30M sodium phosphate buffer solution (6.36 ml, pH 7.0) was shaken for an hour under hydrogen atmosphere (40 psi) at ambient temperature. This mixture was added to a solution of 4-nitrobenzyl(5R,6S)-3-(4-pyridylthio)-6-[1-methyl-1-(4-nitrobenzyloxycarbonyloxy)ethyl]-7-oxo-1-azabicyclo[3.2.0]hept-2-ene-2-carboxylate (132.5 mg) in a mixture of dioxane (3.71 ml) and 1/30M sodium phosphate buffer solution (1.59 ml, pH 7.0), and the resultant mixture was shaken for 2.5 hours under hydrogen atmosphere (40 psi) under ice-cooling.

To the mixture was added 1% aqueous sodium bicarbonate (1.75 ml) at 0° C. and filtered through Celite. The filter-cake was washed with water and the combined filtrates were concentrated. To the concentrate was added sodium chloride (2.4 g), and the solution was washed with ethyl acetate (3×20 ml) and concentrated again in vacuo to 50 ml of the original volume. The concentrate was chromatographed on nonionic adsorption resin "Diaion HP-20" (2×21 cm), which was prewashed with 5% aqueous sodium chloride (120 ml), eluting with water (240 ml) and a mixture of water and acetone (10:0 to 7:3, 120 ml). The fractions, whose UV spectra showed λmax 303 nm, were collected, concentrated and lyophilized to give sodium (5R,6S)-3-(4-pyridylthio)-6-(1-hydroxy-1-methylethyl)-7-oxo-1-azabicyclo[3.2.0]hept-2-ene-2-carboxylate (40.0 mg) as a white solid.

IR (KBr): 3380, 1755, 1600, 1575, 1385 cm$^{-1}$.

UV (H$_2$O): 303 nm (ε=1.03×10$^4$).

NMR (D$_2$O) δ: 1.32 (s, 3H), 1.39 (s, 3H), 2.91 (d, 2H, J=9 Hz), 3.48 (d, 1H, J=3 Hz), 4.26 (dt, 1H, J=3, 9 Hz), 7.51 (d, 2H, J=5 Hz), 8.48 (d, 2H, J=5 Hz).

EXAMPLE 5

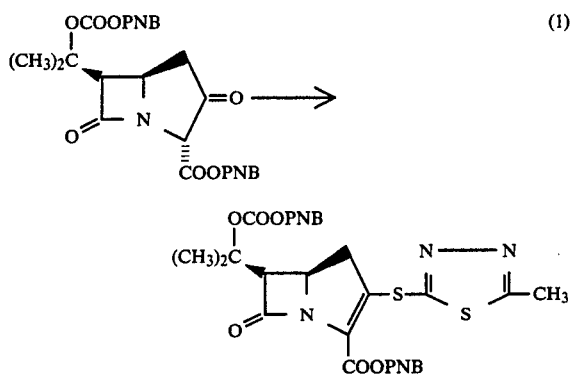

N,N-Diisopropyl-N-ethylamine (0.309 ml) was added to a solution of 4-nitrobenzyl (2R,5R,6R)-3,7-dioxo-6-[1-methyl-1-(4-nitrobenzyloxycarbonyloxy)ethyl]-1-azabicyclo[3.2.0]heptane-2-carboxylate (800 mg) and 4-(N,N-dimethylamino)pyridine (18 mg) in methylene chloride (40 ml) at −30° C. To this mixture was added a solution of trifluoromethanesulfonic anhydride (0.261 ml) in methylene chloride (2.35 ml). After the mixture was stirred at −30° C. for 30 minutes, to the reaction mixture was added N,N-diisopropyl-N-ethylamine (0.772 ml) at −30° C., and further a solution of 5-methyl-1,3,4-thiadiazole-2-thiol (205 mg) in N,N-dimethylformamide (10 ml) was added. The mixture was allowed to warm to ambient temperature over a period of 30 minutes and stirred at the same temperature for 2.5 hours. The resultant mixture was evaporated in vacuo and the residue was dissolved in ethyl acetate (100 ml). The solution was washed with water and a saturated aqueous sodium chloride, dried over magnesium sulfate and evaporated in vacuo. The residue was chromatographed on deactivated silica gel with 10% water (10 g), eluting with a mixture of benzene and acetone (50:1 to 20:1) to give 4-nitrobenzyl (5R,6R)-6-[1-methyl-1-(4-nitrobenzyloxycarbonyloxy)ethyl]-3-(5-methyl-1,3,4-thiadiazol-2-ylthio)-7-oxo-1-azabicyclo[3.2.0]hept-2-ene-2-carboxylate (824 mg) as an oil.

IR (CH$_2$Cl$_2$): 1785, 1750, 1705, 1520, 1350 cm$^{-1}$.

NMR (CDCl$_3$) δ: 1.57 (s, 3H), 1.80 (s, 3H), 2.81 (s, 3H), 3.04 (dd, 1H, J=10, 19 Hz), 3.70 (dd, 1H, J=8, 19 Hz), 3.75 (d, 1H, J=6 Hz), 4.3 (m, 1H), 5.20 (ABq, 2H, J=14 Hz), 5.42 (ABq, 2H, J=14 Hz), 7.57 (d, 2H, J=9 Hz), 7.67 (d, 2H, J=9 Hz), 8.22 (d, 4H, J=9 Hz).

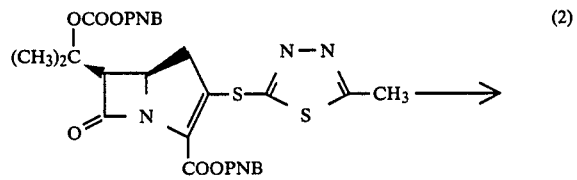

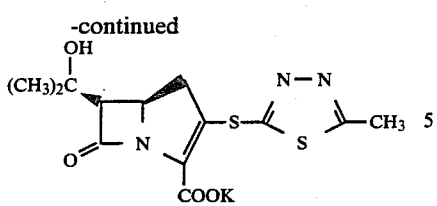

A mixture of 4-nitrobenzyl (5R,6R)-6-[1-methyl-1-(4-nitrobenzyloxycarbonyloxy)ethyl]-3-(5-methyl-1,3,4-thiadiazol-2-ylthio)-7-oxo-1-azabicyclo[3.2.0]hept-2-ene-2-carboxylate (50 mg) and platinum (IV) oxide monohydrate (50 mg) in a mixture of dioxane (6 ml), ethanol (0.5 ml), 0.1M aqueous dipotassium hydrogen phosphate (2.28 ml) and water (2.5 ml) was shaken for 1.5 hours under a hydrogen atmosphere (40 psi) at ambient temperature. The catalyst was filtered off and the filtrate was concentrated to half of the original volume. The aqueous concentrate was washed three times with diethyl ether and evaporated in vacuo. The residue was dissolved in water (25 ml) and potassium chloride (1.25 g) was added. The aqueous solution was chromatographed on non-ionic adsorption resin, "Diaion HP-20 AG" (Trademark, manufactured by Mitsubishi Chemical Industries Ltd.) (1.2×22 cm), eluting with water (150 ml) and aqueous isopropyl alcohol (5 to 30%, 100 ml). The fractions, whose UV spectra showed λmax 293 nm, were combined and lyophilized to give potassium (5R,6R)-6-(1-hydroxy-1-methylethyl)-3-(5-methyl-1,3,4-thiadiazol-2-ylthio)-7-oxo-1-azabicyclo[3.2.0]hept-2-ene-2-carboxylate (16.9 mg).

IR (Nujol): 1750 cm$^{-1}$

NMR (D$_2$O) δ: 1.23 (s, 3H), 1.42 (s, 3H), 2.78 (dd, 1H, J=10, 17 Hz), 2.80 (s, 3H), 3.70 (dd, 1H, J=8, 17 Hz), 3.74 (d, 1H, J=6 Hz), 4.3 (m, 1H).

UV (H$_2$O) λmax: 293 nm (ε=9740).

EXAMPLE 6

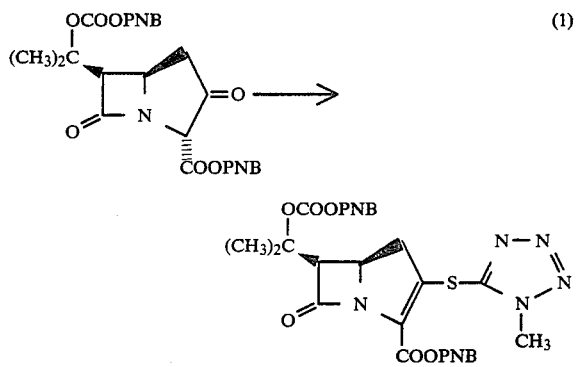

A solution of N,N-diisopropyl-N-ethylamine (0.0386 ml) in methylene chloride (0.347 ml) was added to a solution of 4-nitrobenzyl (2R,5R,6R)-3,7-dioxo-6-[1-methyl-1-(4-nitrobenzyloxycarbonyloxy)ethyl]-1-azabicyclo[3.2.0]heptane-2-carboxylate (100 mg) and 4-(N,N-dimethylamino)pyridine (2.3 mg) in methylene chloride (5 ml) at −30° C. A solution of trifluoromethanesulfonic anhydride (0.0326 ml) in methylene chloride (0.293 ml) was then added thereto at −30° C. After the mixture was stirred at the same temperature for an hour, a solution of N,N-diisopropyl-N-ethylamine (0.129 ml) in methylene chloride (1.16 ml) and a solution of 1-methyl-1H-tetrazole-5-thiol (42.9 mg) in methylene chloride (2.15 ml) were added successively at −30° C.

The mixture was stirred at −30° C. for 30 minutes and allowed to warm to ambient temperature over a period of 30 minutes. After stirring at ambient temperature for 2 hours, the mixture was allowed to stand at 4° C. for 2 days. After removal of the solvent, the residue was dissolved in ethyl acetate. The solution was washed three times with water and an aqueous sodium chloride, dried over magnesium sulfate and then evaporated in vacuo. The residue was chromatographed on deactivated silica gel with 10% water (2 g), eluting with a mixture of benzene and acetone (50:1 to 10:1) to give 4-nitrobenzyl (5R,6R)-6-[1-methyl-1-(4-nitrobenzyloxycarbonyloxy)ethyl]-3-(1-methyl-1H-tetrazol-5-ylthio)-7-oxo-1-azabicyclo[3.2.0]hept-2-ene-2-carboxylate (89 mg) as an oil.

IR (CH$_2$Cl$_2$): 1790, 1750, 1700, 1520, 1350 cm$^{-1}$.

NMR (DMSO-d$_6$) δ: 1.45 (s, 3H), 1.66 (s, 3H), 2.3–2.8 (m, 1H), 3.1–3.7 (m, 1H), 4.00 (s, 3H), 4.02 (d, 1H, J=6 Hz), 4.2–4.4 (m, 1H), 5.24 (broad s, 2H), 5.46 (ABq, 2H, J=15 Hz), 7.67 (d, 2H, J=9 Hz), 7.72 (d, 2H, J=9 Hz), 8.22 (d, 4H, J=9 Hz).

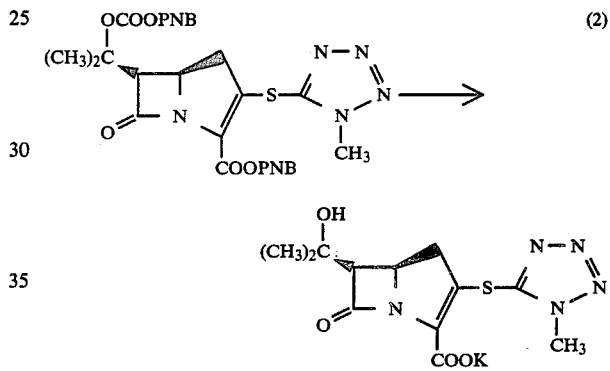

A mixture of 4-nitrobenzyl (5R,6R)-6-[1-methyl-1-(4-nitrobenzyloxycarbonyloxy)ethyl]-3-(1-methyl-1H-tetrazol-5-ylthio)-7-oxo-1-azabicyclo[3.2.0]hept-2-ene-2-carboxylate (50 mg) and platinum (IV) oxide monohydrate (25 mg) in a mixture of dioxane (10 ml), ethanol (0.5 ml), 0.1M aqueous dipotassium hydrogen phosphate (2.35 ml) and water (3.5 ml) was shaken for an hour under a hydrogen atmosphere (40 psi) at ambient temperature. The catalyst was filtered off and the filtrate was concentrated to half of the original volume. The aqueous concentrate was washed three times with diethyl ether and evaporated in vacuo. The residue was dissolved in water (25 ml) and potassium chloride (1.25 g) was added thereto. The aqueous solution was chromatographed on non-ionic adsorption resin "Diaion HP-20 AG" (1.35×17.5 cm), eluting with water (100 ml) and 10% aqueous isopropyl alcohol (100 ml). The fractions, whose UV spectra showed λmax 289 nm, were combined and lyophilized to give potassium (5R,6R)-6-(1-hydroxy-1-methylethyl)-3-(1-methyl-1H-tetrazol-5-ylthio)-7-oxo-1-azabicyclo[3.2.0]hept-2-ene-2-carboxylate (17 mg).

IR (Nujol): 1760 cm$^{-1}$.

NMR (D$_2$O) δ: 1.17 (s, 3H), 1.40 (s, 3H), 2.48 (dd, 1H, J=10, 16 Hz), 3.53 (dd, 1H, J=9, 16 Hz), 3.72 (d, 1H, J=6 Hz), 4.13 (s, 3H), 4.2 (m, 1H)

UV (H$_2$O) λmax: 289 nm (ε=7470).

EXAMPLE 7

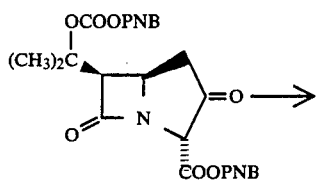

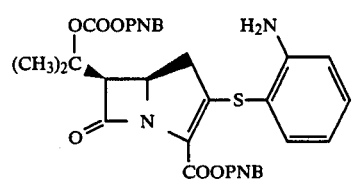

A solution of N,N-diisopropyl-N-ethylamine (0.247 ml) in acetonitrile (2.2 ml) was added to a solution of 4-nitrobenzyl (2R,5R,6R)-3,7-dioxo-6-[1-methyl-1-(4-nitrobenzyloxycarbonyloxy)ethyl]-1-azabicyclo[3.2.0-]heptane-2-carboxylate (640 mg) and 4-(N,N-dimethylamino)pyridine (14.4 mg) in acetonitrile (32 ml) at 0° C. A solution of diphenyl chlorophosphate (0.257 ml) in acetonitrile (2.3 ml) was then added thereto at 0° C. After the mixture was stirred at 0° C. for 30 minutes, N,N-diisopropyl-N-ethylamine (0.824 ml) and a solution of 2-aminobenzenethiol (155 mg) in acetonitrile (1.4 ml) were added at 0° C. After stirring at 0° C. for an hour, the mixture was evaporated in vacuo and the residue was dissolved in ethyl acetate (50 ml). This solution was washed twice with water (X2) and an aqueous sodium chloride, dried over magnesium sulfate, and then evaporated in vacuo. The residue was chromatographed on silica gel (20 g) eluting with a mixture of benzene and acetone (50:1 to 10:1) to give 4-nitrobenzyl (5R,6R)-3-(2-aminophenylthio)-6-[1-methyl-1-(4-nitrobenzyloxycarbonyloxy)ethyl]-7-oxo-1-azabicyclo[3.2.0]hept-2-ene-2-carboxylate (603 mg) as an oil.

IR ($CH_2Cl_2$): 1775, 1750, 1705, 1520, 1350 cm$^{-1}$.

NMR (CDCl$_3$) δ: 1.52 (s, 3H), 1.76 (s, 3H), 2.52 (dd, 1H, J=9, 18 Hz), 3.40 (dd, 1H, J=9, 18 Hz), 3.70 (d, 1H, J=5.5 Hz), 4.0–4.3 (m, 3H), 5.18 (s, 2H), 5.41 (ABq, 2H, J=15 Hz), 6.4–6.7 (m, 2H), 7.0–7.3 (m, 2H), 7.52 (d, 2H, J=8 Hz), 7.70 (d, 2H, J=8 Hz), 8.25 (d, 4H, J=8 Hz).

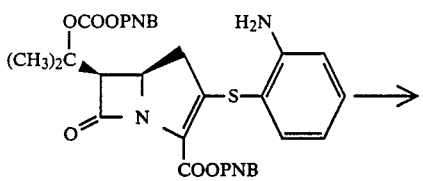

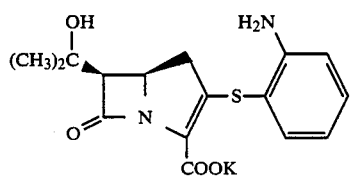

A mixture of 4-nitrobenzyl (5R,6R)-3-(2-aminophenylthio)-6-[1-methyl-1-(4-nitrobenzyloxycarbonyloxy)ethyl]-7-oxo-1-azabicyclo[3.2.0]hept-2-ene-2-carboxylate (490 mg) and platinum (IV) oxide monohydrate (200 mg) in a mixture of dioxane (60 ml), ethanol (5 ml), 0.1M aqueous dipotassium hydrogen phosphate (22.7 ml) and water (25 ml) was shaken for 50 minutes under a hydrogen atmosphere (40 psi) at ambient temperature. The catalyst was filtered off and the filtrate was concentrated to half of the original volume. The aqueous concentrate was washed three times with diethyl ether and evaporated in vacuo. The residue was dissolved in water (250 ml), and potassium chloride (12.5 g) was added thereto. The aqueous solution was chromatographed on non-ionic adsorption resin "Diaion HP-20 AG" (3.1×33 cm) eluting with water (1 liter) and aqueous isopropyl alcohol (5 to 30%, 1 liter). The fractions, whose UV spectra showed λ max 303 nm, were combined and lyophilized to give potassium (5R, 6R)-3-(2-aminophenylthio)-6-(1-hydroxy-1-methylethyl)-7-oxo-1-azabicyclo[3.2.0]hept-2-ene-2-carboxylate (130 mg).

IR (Nujol): 1750 cm$^{-1}$.

NMR (D$_2$O) δ: 1.17 (s, 3H), 1.41 (s, 3H), 2.41 (dd, 1H, J=10, 17 Hz), 3.52 (dd, 1H, J=9, 17 Hz), 3.70 (d, 1H, J=5.5 Hz), 4.0–4.4 (m, 1H), 6.8–7.1 (m, 2H), 7.2–7.7 (m, 2H).

UV (H$_2$O) λ max: 303 nm (ε=11920).

EXAMPLE 8

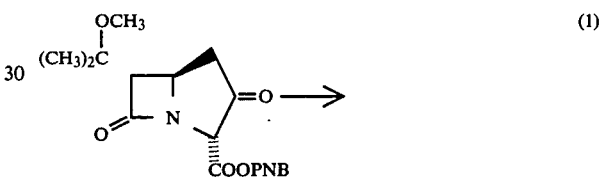

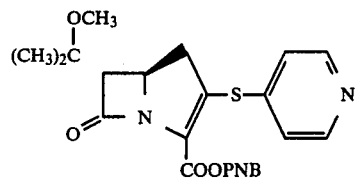

To a solution of 4-nitrobenzyl (2R, 5R, 6S)-3,7-dioxo-6-(1-methoxy-1-methylethyl)-1-azabicyclo[3.2.0]heptane-2-carboxylate (50.0 mg) and 4-(N,N-dimethylamino)pyridine (1.62 mg) in acetonitrile (2.5 ml) was added dropwise a solution of N,N-diisopropyl-N-ethylamine (27.8 μl) in acetonitrile (0.25 ml), followed by addition of a solution of diphenyl chlorophosphate (28.9 μl) in acetonitrile (0.26 ml) at 0° C. After stirring for one hour at 0° C., a solution of N,N-diisopropyl-N-ethylamine (92.7 μl) in acetonitrile (0.834 ml) and pyridine-4-thiol (15.6 mg) were successively added at −15° C., and the mixture was allowed to stand at −15° C. overnight. The resultant solution was concentrated in vacuo. The residue was diluted with ethyl acetate (10 ml) and washed twice with water and a saturated aqueous sodium chloride. After drying over magnesium sulfate, the ethyl acetate solution was filtered and evaporated. The residue (68.7 mg) was chromatographed on deactivated silica gel (1.5 g) with 10% water, eluting with a mixture of benzene and acetone (100:1 to 6:1) to give 4-nitrobenzyl (5R, 6S)-6-(1-methoxy-1-methylethyl)-7-oxo-3-(4-pyridylthio)-1-azabicyclo[3.2.0]hept-2-ene-2-carboxylate (51.7 mg) as an amorphous solid.

IR (CH$_2$Cl$_2$): 1780, 1720, 1705, 1520, 1350 cm$^{-1}$.

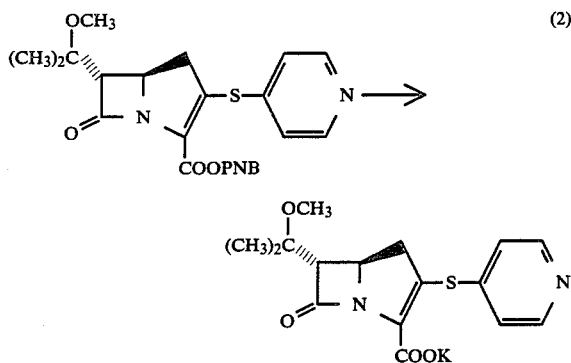

A mixture of 4-nitrobenzyl (5R, 6S)-6-(1-methoxy-1-methylethyl)-7-oxo-3-(4-pyridylthio)-1-azabicyclo[3.2.0]hept-2-ene-2-carboxylate (371.0 mg) and platinum (IV) oxide (123.7 mg) in a mixture of dioxane (44.5 ml), 0.1M aqueous dipotassium hydrogen phosphate (23.7 ml), water (5.98 ml) and ethanol (3.71 ml) was shaken for an hour under a hydrogen atmosphere (50 psi) at ambient temperature. The reaction mixture was filtered using super cell. The filter cake was washed with water, and the combined filtrates were concentrated. The residual aqueous layer was washed three times with diethyl ether at 0° C. and concentrated. After addition of potassium chloride (9 g), the resultant aqueous solution (180 ml) was chromatographed on non-ionic adsorption resin "Diaion HP-20 AG" (24×300 mm) eluting successively with water (420 ml), 5% aqueous isopropyl alcohol (420 ml) and 10% aqueous isopropyl alcohol (420 ml). The fractions, whose UV spectrum showed λ max 303 nm, were collected, concentrated and lyophilized to give potassium (5R, 6S)-6-(1-methoxy-1-methylethyl)-7-oxo-3-(4-pyridylthio)-1-azabicyclo[3.2.0]hept-2-ene-2-carboxylate (208.7 mg) as a white powder.

IR (neat): 3350, 1750, 1615, 1570, 1380 cm$^{-1}$.

NMR (D$_2$O) δ: 1.3 (s, 3H), 1.33 (s, 3H), 2.89 (d, 2H, J=10 Hz), 3.24 (s, 3H), 3.58 (d, 1H, J=3 Hz), 4.2 (dt, 1H, J=3 and 10 Hz), 7.47 (d, 2H, J=6 Hz), 8.43 (m, 2H).

UV (H$_2$O) λmax: 303 nm ($\epsilon$=1.06×10$^4$).

EXAMPLE 9

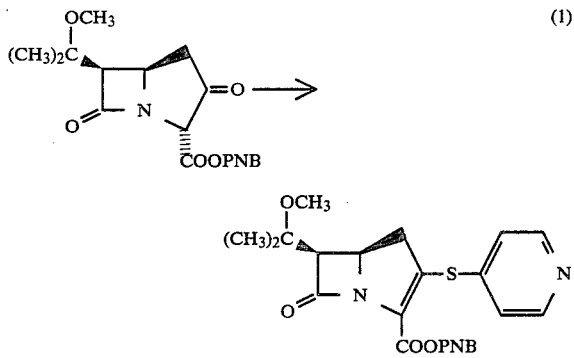

To a solution of 4-nitrobenzyl (2R, 5R, 6R)-3,7-dioxo-6-(1-methoxy-1-methylethyl)-1-azabicyclo[3.2.0]heptane-2-carboxylate (450 mg) and 4-(N,N-dimethylamino)pyridine (14.6 mg) in methylene chloride (22.5 ml) was added a solution of N,N-diisopropyl-N-ethylamine (0.249 ml) in methylene chloride (2.241 ml) at −30° C. To the mixture was added further a solution of trifluoromethanesulfonic anhydride (0.211 ml) in methylene chloride (1.899 ml) at −30° C. After stirring for 30 minutes at the same temperature, a solution of 4-(N,N-dimethylamino)pyridine (2.9 mg) and N,N-diisopropyl-N-ethylamine (0.0498 ml) in methylene chloride (0.448 ml) and then a solution of trifluoromethanesulfonic anhydride (0.0422 ml) in methylene chloride (0.38 ml) were added thereto at −30° C. After stirring for 30 minutes at the same temperature a solution of N,N-diisopropyl-N-ethylamine (0.833 ml) in methylene chloride (7.497 ml) and a solution of pyridine-4-thiol (159.5 mg) in N,N-dimethylformamide (5.63 ml) were added successively thereto at −30° C. The resultant solution was stirred for 30 minutes at the same temperature and for additional 30 minutes at 0° C. The solvent was distilled off and the residue was dissolved in ethyl acetate, washed twice with water and a saturated aqueous sodium chloride. After drying over magnesium sulfate, the solution was filtered and evaporated. The residue was chromatographed on deactivated silica gel with 10% water (13.5 g), eluting with a mixture of benzene and acetone (100:1 to 6:1) to give 4-nitrobenzyl (5R, 6R)-6-(1-methoxy-1-methylethyl)-7-oxo-3-(4-pyridylthio)-1-azabicyclo[3.2.0]-hept-2-ene-2-carboxylate (379 mg) as a pale yellow solid.

IR (CH$_2$Cl$_2$): 1780, 1710 cm$^{-1}$.

NMR (CDCl$_3$) δ: 1.14 (s, 3H), 1.43 (s, 3H), 2.57 (dd, 1H, J=10, 18 Hz), 3.22 (s, 3H), 3.58 (d, 1H, J=8 Hz), 3.83 (dd, 1H, J=10, 18 Hz), 4.22 (ddd, 1H, J=8, 10, 20 Hz), 5.42 (ABq, 2H, J=13 Hz), 7.2–7.5 (m, 2H), 7.6–7.8 (m, 2H), 8.1–8.4 (m, 2H), 8.5–8.7 (m, 2H).

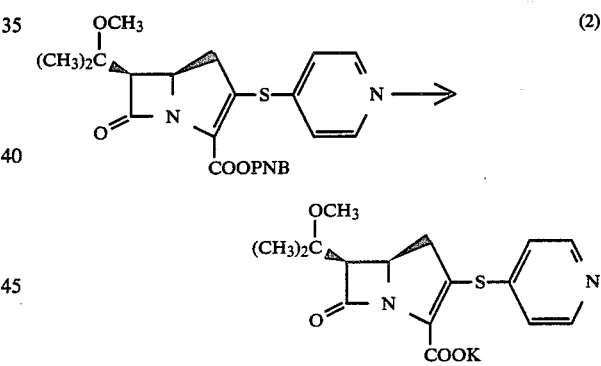

A mixture of 4-nitrobenzyl (5R, 6R)-6-(1-methoxy-1-methylethyl)-7-oxo-3-(4-pyridylthio)-1-azabicyclo[3.2.0]hept-2-ene-2-carboxylate (520 mg) and platinum (IV) oxide (173 mg) in a mixture of dioxane (62.4 ml), 0.1M aqueous dipotassium hydrogen phosphate (33.23 ml), water (8.39 ml) and ethanol (5.2 ml) was shaken for an hour under a hydrogen atmosphere (50 psi) at ambient temperature. After the catalyst was filtered off, the filtrate was concentrated. The residual aqueous layer was washed three times with diethyl ether at 0° C. and concentrated. The residue was dissolved in water (260 ml), and potassium chloride (13 g) was added thereto. The aqueous solution was chromatographed on non-ionic adsorption resin "Diaion HP-20 AG" eluting with water (3 liter) and 5% aqueous isopropyl alcohol (2 liter). The fractions, whose UV spectra showed λ max 303 nm, were combined and lyophilized to give potassium (5R, 6R)-6-(1-methoxy-1-methylethyl)-7-oxo-3-(4-pyridylthio)-1-azabicyclo[3.2.0]hept-2-ene-2-carboxylate (305 mg) as a white powder.

IR (Nujol): 1750, 1600, 1570 cm$^{-1}$.

NMR (D$_2$O) δ: 1.22 (s, 3H), 1.38 (s, 3H), 2.77 (dd, 1H, J=10, 17 Hz), 3.24 (s, 3H), 3.52 (dd, 1H, J=10, 17 Hz), 3.86 (d, 1H, J=7 Hz), 4.33 (ddd, 1H, J=7, 9, 10 Hz), 7.3–7.7 (m, 2H), 8.3–8.7 (m, 2H).

EXAMPLE 10

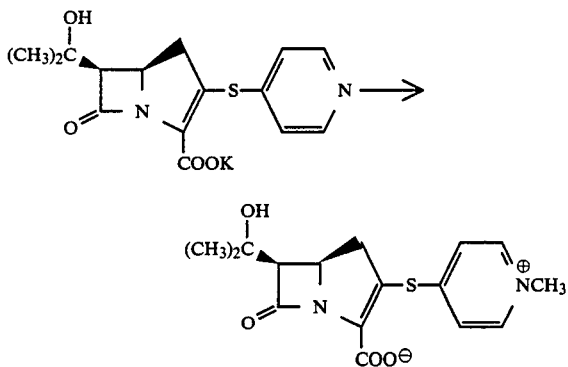

Iodomethane (0.5 ml) was added to a solution of potassium (5R, 6R)-6-(1-hydroxy-1-methylethyl)-7-oxo-3-(4-pyridylthio)-1-azabicyclo[3.2.0]hept-2-ene-2-carboxylate (23 mg) in 50% aqueous dioxane (2 ml) at 0° C., and the mixture was allowed to warm to ambient temperature. After the mixture was stirred at ambient temperature for 2 hours, iodomethane (0.25 ml) and 5% aqueous dioxane (2 ml) were added thereto. After the mixture was stirred at ambient temperature for 2 hours, iodomethane (0.25 ml) was added. The resultant mixture was allowed to stand at 5° C. overnight and stirred at ambient temperature for 4 hours. The mixture was concentrated to half of the original volume, and the aqueous concentrate was washed three times with ethyl acetate. The aqueous layer was concentrated and the residue was dissolved in water (10 ml). The aqueous solution was chromatographed on non-ionic adsorption resin "Diaion HP-20 AG" (0.3×20 cm), eluting with water (50 ml) and 10% aqueous isopropyl alcohol (50 ml). The fractions, whose UV spectra showed λ max 304 nm, were combined and lyophilized to give (5R, 6R)-6-(1-hydroxy-1-methylethyl)-3-(1-methyl-4-pyridiniothio)-7-oxo-1-azabicyclo[3.2.0]hept-2-ene-2-carboxylate (15 mg).

NMR (D$_2$O) δ: 1.31 (s, 3H), 1.48 (s, 3H), 2.97 (dd, 1H, J=11, 18 Hz), 3.80 (dd, 1H, J=9, 18 Hz), 3.83 (d, 1H, J=6 Hz), 4.24 (s, 3H), 4.5 (m, 1H), 7.78 (d, 2H, J=7 Hz), 8.43 (d, 2H, J=7 Hz).

UV (H$_2$O) λ max: 304 nm.

EXAMPLE 11

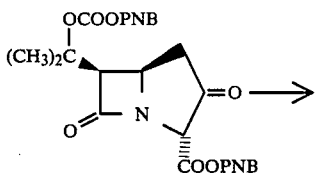 (1)

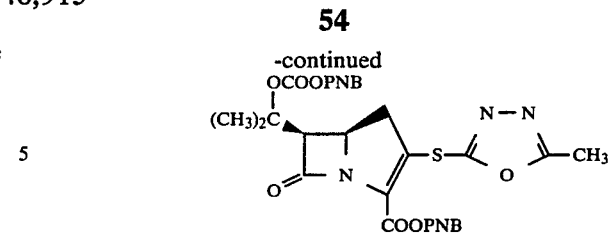

A solution of N,N-diisopropyl-N-ethylamine (0.135 ml) in methylene chloride (1.21 ml) was added to a solution of 4-nitrobenzyl (2R, 5R, 6R)-3,7-dioxo-6-[1-methyl-1-(4-nitrobenzyloxycarbonyloxy)ethyl]-1-azabicyclo[3.2.0]heptane-2-carboxylate (350 mg) and 4-(N,N-dimethylamino)pyridine (7.9 mg) in methylene chloride (17.5 ml) at −30° C. A solution of trifluoromethanesulfonic anhydride (0.114 ml) in methylene chloride (1.02 ml) was added to the mixture and stirring was continued at the same temperature for 30 minutes. A solution of N,N-diisopropyl-N-ethylamine (0.563 ml) in methylene chloride (5.06 ml) and 5-methyl-1,3,4-oxadiazole-2-thiol (225 mg) were then added thereto, and the reaction mixture was stirred at −30° C. for 30 minutes and allowed to warm to ambient temperature over a period of an hour. After stirring at ambient temperature for 4 hours, the mixture was allowed to stand at 5° C. for 14 hours. After the solvent was removed by evaporation, the residue was dissolved in ethyl acetate (20 ml). The organic solution was washed in turn with water and a saturated aqueous sodium chloride, dried over magnesium sulfate and evaporated in vacuo. The residue was chromatographed on deactivated silica gel with 10% water (7 g), eluting with a mixture of benzene and acetone (20:1 to 10:1) to give 4-nitrobenzyl (5R, 6R)-6-[1-methyl-1-(4-nitrobenzyloxycarbonyloxy)ethyl]-3-(5-methyl-1,3,4-oxadiazol-2-ylthio)-7-oxo-1-azabicyclo[3.2.0]hept-2-ene-2-carboxylate (290 mg) as an oil.

IR (CH$_2$Cl$_2$): 1790, 1750, 1520, 1350 cm$^{-1}$.

NMR (CDCl$_3$) δ: 1.59 (s, 3H), 1.80 (s, 3H), 2.57 (s, 3H), 3.22 (dd, 1H, J=11, 18 Hz), 3.75 (dd, 1H, J=8, 18 Hz), 3.76 (d, 1H, J=6 Hz), 4.3–4.6 (m, 1H), 5.18 (ABq, 2H, J=15 Hz), 5.42 (ABq, 2H, J=14 Hz), 7.54 (d, 2H, J=9 Hz), 7.67 (d, 2H, J=9 Hz), 8.22 (d, 2H, J=9 Hz), 8.23 (d, 2H, J=9 Hz).

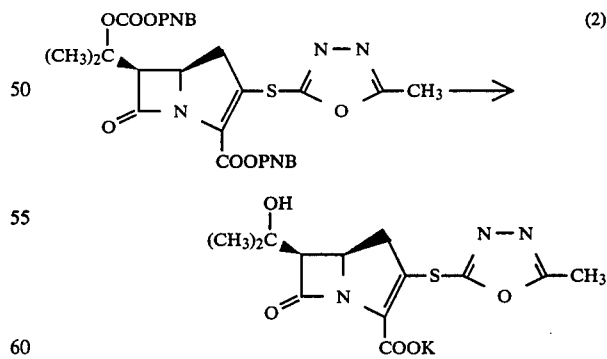 (2)

A mixture of 4-nitrobenzyl (5R, 6R)-6-[1-methyl-1-(4-nitrobenzyloxycarbonyloxy)ethyl]-3-(5-methyl-1,3,4-oxadiazol-2-ylthio)-7-oxo-1-azabicyclo[3.2.0]hept-2-ene-2-carboxylate (50 mg), platinum (IV) oxide monohydrate (50 mg), ethanol (0.5 ml) and 0.1M aqueous solution of dipotassium hydrogen phosphate (2.35 ml) in a mixture of water (2.5 ml) and dioxane (6 ml) was shaken under a hydrogen atmosphere (40 psi) at ambient temperature for an hour. After the catalyst was filtered off, the filtrate was evaporated to half of the original volume. The resultant aqueous solution was washed three times with diethyl ether and then evaporated in vacuo. The residue was dissolved in water (25 ml) and the resultant aqueous solution was chromatographed on nonionic adsorption resin "Diaion HP-20AG" eluting with water (100 ml) and 10% aqueous isopropyl alcohol (100 ml). The fractions, whose UV spectra showed λmax 292 nm, were combined and lyophilized to give potassium (5R, 6R)-6-(1-hydroxy-1-methylethyl)-3-(5-methyl-1,3,4-oxadiazol-2-ylthio)-7-oxo-1-azabicyclo[3.2.0]hept-2-ene-2-carboxylate (14.3 mg) as powder.

NMR (D$_2$O) δ: 1.24 (s, 3H), 1.40 (s, 3H), 2.59 (s, 3H), 3.24 (dd, 1H, J=11, 18 Hz), 3.74 (dd, 1H, J=8, 18 Hz), 3.75 (d, 1H, J=6 Hz), 4.2–4.4 (m, 1H).

UV (H$_2$O): λmax 292 nm.

EXAMPLE 12

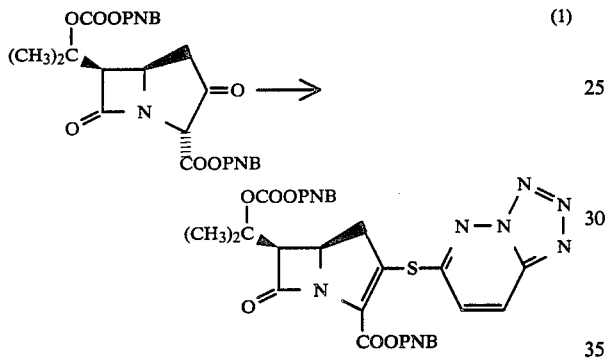

A solution of N,N-diisopropyl-N-ethylamine (0.231 ml) in dichloromethane (2.08 ml) was added to a solution of 4-nitrobenzyl (2R, 5R, 6R)-3,7-dioxo-6-[1-methyl-1-(4-nitrobenzyloxycarbonyloxy)ethyl]1-azabicyclo[3.2.0]heptane-2-carboxylate (600 mg) and 4-(N,N-dimethylamino)pyridine (13.5 mg) in dichloromethane (30.0 ml) at −30° C. To this mixture was added a solution of trifluoromethanesulfonic anhydride (0.196 ml) in dichloromethane (3.72 ml) and stirring was continued at −30° C. for 20 minutes. N,N-Diisopropyl-N-ethylamine (0.680 ml) and a solution of tetrazolo[1,5-b]pyridazine-6-thiol (0.256 g) in N,N-dimethylformamide (2.30 ml) were added to the mixture at −30° C. The resultant mixture was allowed to warm to 20° C. over a period of 2 hours, and then evaporated in vacuo. The residue was dissolved in ethyl acetate (100 ml), washed in turn with cold water (x3) and an aqueaus sodium chloride, dried over magnesium sulfate and evaporated in vacuo. The residue was chromatographed on deactivated silica gel with 15% water (7.5 g), eluting with a mixture of benzene and acetone (20:1 to 6:1). The fractions containing the desired compound were collected and diluted with benzene to result in precipitation of crystals, which, after cooling in a refrigerator, were collected by filtration to give 4-nitrobenzyl (5R, 6R)-6-[1-methyl-1-(4-nitrobenzyloxycarbonyloxy)ethyl]-7-oxo-3-(tetrazolo[1,5-b]pyridazin-6-ylthio)-1azabicyclo[3.2.0]hept-2-ene-2-carboxylate (0.533 g). Crystallization of the mother liquor from ethyl acetate and n-hexane gave the same product (0.0663 g) as a pale yellow powder.

Total yield was 0.5993 g.

mp. 127°–128.5° C.

IR(CH$_2$Cl$_2$): 1790, 1755, 1610, 1530, 1355 cm$^{-1}$.

NMR(CDCl$_3$) δ: 1.65 (s, 3H), 1.83 (s, 3H), 3.5–4.0 (m, 3H), 4.50 (m, 1H), 5.18 (s, 2H), 5.43 (ABq, 2H, J=14 Hz), 7.2–7.8 (m, 6H), 8.0–8.3 (m, 4H).

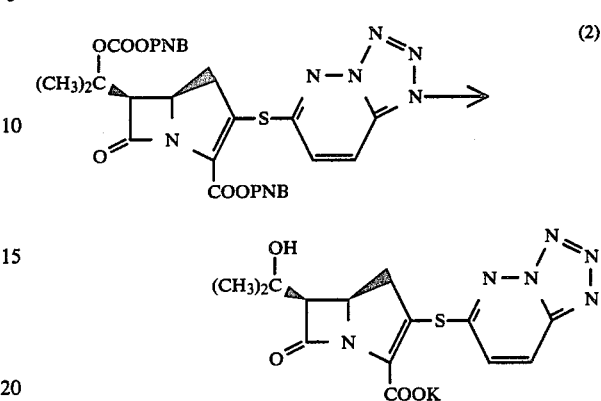

A mixture of 4-nitrobenzyl (5R, 6R)-6-[1-methyl-1-(4-nitrobenzyloxycarbonyloxy)ethyl]-7-oxo-3-(tetrazolo[1,5-b]pyridazin-6-ylthio)-1-aza-bicyclo[3.2.0-]hept-2-ene-2-carboxylate (0.4357 g), platinum (IV) oxide monohydrate (0.2179 g) in 0.047M aqueous dipotassium hydrogen phosphate (41.1 ml), tetrahydrofuran (52.3 ml) and ethanol (4.40 ml) was stirred for 3.7 hours in hydrogen gas under atmospheric pressure at ambient temperature. After the catalyst was filtered off, the filtrate was concentrated to half of the original volume. The aqueous concentrate was washed with diethyl ether (x3) and evaporated in vacuo. The residue was chromatographed on nonionic adsorption resin "Diaion CHP-20P" (Trademark, manufactured by Mitsubishi Chemical Industries) (220 ml) eluting with water (1.50 l), 5% aqueous isopropyl alcohol (400 ml) and 10% aqueous isopropyl alcohol (400 ml). The fractions, whose IV spectra showed λ max 233.0 nm and 282.5 nm, were combined and lyophilized to give crude product (0.1459 g), which was chromatographed again on "Diaion CHP-20P" (130 ml) eluting with water (340 ml), 5% aqueous isopropyl alcohol (360 ml) and 10 aqueous isopropyl alcohol (200 ml). The fractions containing the desired compound were collected and lyophilized to give potassium (5R, 6R)-6-(1-hydroxy-1-methylethyl)-3-(tetrazolo[1,5-b]pyridazin-6-ylthio)-7-oxo-1-azabicyclo[3.2.0]hept-2-ene-2-carboxylate (0.1299 g) as a yellow powder.

IR (Nujol): 1750 cm$^{-1}$.

NMR (D$_2$O) δ: 1.34 (s, 3H), 1.52 (s, 3H), 3.40 (dd, 1H, J=12, 18 Hz), 3.94 (dd, 1H, J=9, 18 Hz), 3.96 (d, 1H, J=6 Hz), 4.64 (m, 1H), 8.00 (d, 1H, J=15 Hz), 8.68 (d, 1H, J=15 Hz).

UV (H$_2$O) λ max: 282.5 nm (ε=9400); 233.0 nm (ε=11500).

EXAMPLE 13

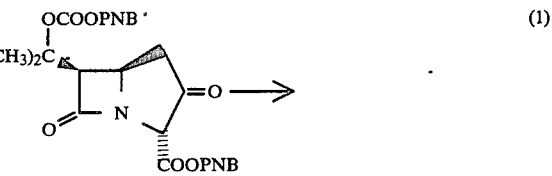

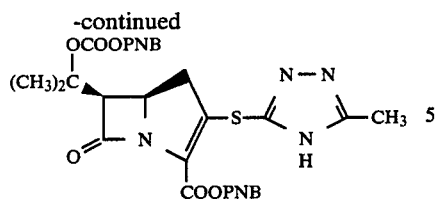

4-Nitrobenzyl (5R, 6R)-6-[1-methyl-1-(4-nitrobenzyloxycarbonyloxy)ethyl]-3-(5-methyl-4H-1,2,4-triazol-3-ylthio)-7-oxo-1-azabicyclo[3.2.0]hept-2-ene-2-carboxylate (622 mg) was obtained by reacting 4-nitrobenzyl (2R, 5R, 6R)-3,7-dioxo-6-[1-methyl-1-(4-nitrobenzyloxycarbonyloxy)ethyl]-1-azabicyclo[3.2.0]heptane-2-carboxylate (600 mg) with trifluoromethanesulfonic anhydride (0.196 ml) and then 5-methyl-4H-1,2,4-triazole-3-thiol (191 mg) according to a similar manner to that of Example 12-(1).

IR ($CH_2Cl_2$): 3420, 1790, 1750, 1710, 1675, 1530, 1350 $cm^{-1}$.

NMR ($CDCl_3$) δ: 1.57 (s, 3H), 1.80 (s, 3H), 2.52 (s, 3H), 3.10 (dd, 1H, J=11, 18 Hz), 3.64 (dd, 1H, J=9, 18 Hz), 3.75 (d, 1H, J=6 Hz), 4.35 (m, 1H), 5.24 (ABq, 2H, J=15 Hz), 5.47 (ABq, 2H, J=15 Hz), 7.64 (d, 2H, J=8 Hz), 7.76 (d, 2H, J=8 Hz), 8.30 (d, 4H, J=8 Hz).

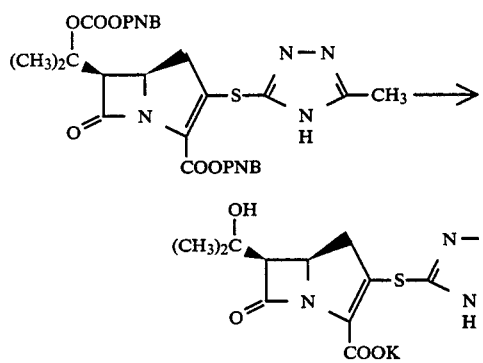

A mixture of 4-nitrobenzyl (5R, 6R)-6-[1-methyl-1-(4-nitrobenzyloxycarbonyloxy)ethyl]-3-(5-methyl-4H-1,2,4-triazol-3-ylthio)-7-oxo-1-azabicyclo[3.2.0]hept-2-ene-2-carboxylate (50 mg) and 5% palladium on activated carbon (50 mg) in 0.048M aqueous dipotassium hydrogen phosphate (4.85 ml), ethanol (0.5 ml), and dioxane (6.0 ml) was shaken for 2 hours under a hydrogen atmosphere (40 psi) at ambient temperature. After the catalyst was filtered off, the filtrate was concentrated to half of the original volume. The aqueous concentrate was washed three times with diethyl ether and evaporated in vacuo. The residue was chromatographed on nonionic adsorption resin "Diaion CHP-20P", eluting with water (100 ml) and 5% aqueous isopropyl alcohol (100 ml). The fractions, whose UV spectra showed λmax 292 nm, were combined and lyophilized to give potassium (5R, 6R)-6-(1-hydroxy-1-methylethyl)-3-(5-methyl-4H-1,2,4-triazol-3-ylthio)-7-oxo-1-azabicyclo[3.2.0]hept-2-ene-2-carboxylate (13.2 mg) as a yellow powder.

IR (Nujol): 1750 $cm^{-1}$.

NMR ($D_2O$) δ: 1.22 (s, 3H), 1.40 (s, 3H), 2.44 (s, 3H), 2.56 (dd, 1H, J=10, 18 Hz), 3.58 (dd, 1H, J=10, 18 Hz), 3.72 (d, 1H, J=7 Hz), 4.28 (dt, 1H, J=7, 10 Hz).

UV ($H_2O$) λmax: 292 nm (ε=5.69×10³).

EXAMPLE 14

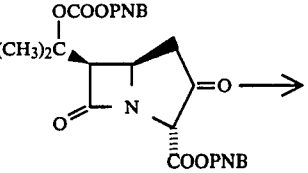

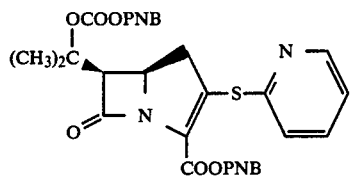

4-Nitrobenzyl (5R, 6R)-6-[1-methyl-1-(4-nitrobenzyloxycarbonyloxy)ethyl]-7-oxo-3-(2-pyridylthio)-1-azabicyclo[3.2.0]hept-2-ene-2-carboxylate (1.57 g) was obtained by reacting 4-nitrobenzyl (2R, 5R, 6R)-3,7-dioxo-6-[1-methyl-1-(4-nitrobenzyloxycarbonyloxy)ethyl]-1-azabicyclo[3.2.0]-heptane-2-carboxylate (1.50 g) with trifluoromethanesulfonic anhydride (0.489 ml) and then 2-mercaptolpyridine (523.6 mg) according to a similar manner to that of Example 12-(1).

IR ($CH_2Cl_2$): 1780, 1750, 1710, 1520, 1350 $cm^{-1}$.

NMR ($CDCl_3$) δ: 1.58 (s, 3H), 1.80 (s, 3H), 3.20 (dd, 1H, J=11, 19 Hz), 3.65 (dd, 1H, J=9, 19 Hz), 3.77 (d, 1H, J=6 Hz), 4.38 (ddd, 1H, J=6, 9, 11 Hz), 5.20 (ABq, 2H, J=14 Hz), 5.43 (ABq, 2H, J=14 Hz), 7.1–7.8 (m, 7H), 8.0–8.4 (m, 4H), 8.5–8.6 (m, 1H).

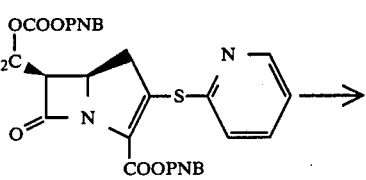

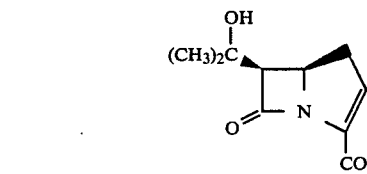

Potassium (5R, 6R)-6-(1-hydroxy-1-methylethyl)-7-oxo-3-(2-pyridylthio)-1-azabicyclo[3.2.0]hept-2-ene-2-carboxylate (21 mg) was obtained by subjecting 4-nitrobenzyl (5R, 6R)-6-[1-methyl-1-(4-nitrobenzyloxycarbonyloxy)ethyl]-7-oxo-3-(2-pyridylthio)-1-azabicyclo[3.2.0]hept-2-ene-2-carboxylate (50 mg) to catalytic reduction under hydrogen atmosphere (40 psi) in the presence of platinum (IV) oxide monohydrate (50 mg) according to a similar manner to that of Example 12-(2).

IR (Nujol): 1750 $cm^{-1}$.

NMR ($D_2O$) δ: 1.22 (s, 3H), 1.44 (s, 3H), 2.70 (dd, 1H, J=10, 17 Hz), 3.66 (dd, 1H, J=9, 17 Hz), 3.78 (d, 1H, J=5 Hz), 4.36 (ddd, 1H, J=5, 9, 10 Hz), 7.4–8.1 (m, 3H), 8.65 (m, 1H).

UV ($H_2O$) λ max: 304 nm (ε=1.17×10⁴).

EXAMPLE 15

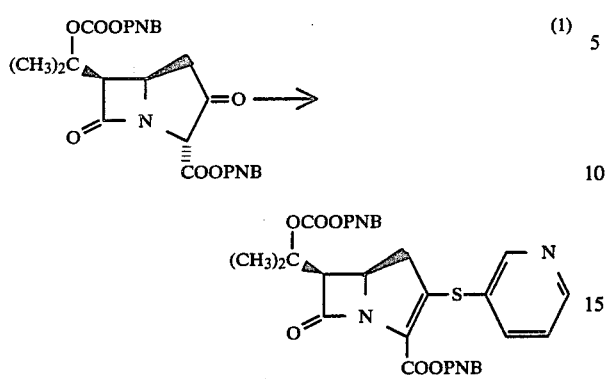

A solution of N,N-diisopropyl-N-ethylamine (0.579 ml) in dichloromethane (5.21 ml) was added to a solution of 4-nitrobenzyl (2R, 5R, 6R)-3,7-dioxo-6-[1-methyl-1-(4-nitrobenzyloxycarbonyloxy)ethyl]-1-azabicyclo[3.2.0]heptane-2-carboxylate (1.50 g) and 4-(N,N-dimethylamino)pyridine (33.8 mg) in dichloromethane (75.0 ml) at −30° C. To this solution was added a solution of trifluoromethanesulfonic anhydride (0.489 ml) in dichloromethane (9.29 ml) and the mixture was stirred at −30° C. for 20 minutes. N,N-Diisopropyl-N-ethylamine (5.31 ml) and a solution of stannic chloride and hydrochloric acid salts of 3-mercaptopyridine (1.70 g) in N,N-dimethylformamide (15.3 ml) were then added to the mixture and the resultant mixture was allowed to warm to 20° C. over a period of 3 hours. After cooling to 0° C., additional N,N-diisopropyl-N-ethylamine (2.89 ml) and a solution of stannic chloride and hydrochloric acid salts of 3-mercaptopyridine (0.570 g) in N,N-dimethylformamide (5.13 ml) were added to the mixture. The resultant mixture was allowed to warm to 20° C. over a period of an hour and evaporated in vacuo. The residue was dissolved in dichloromethane (250 ml), washed in turn with cold water (x6) and an aqueous sodium chloride, dried over magnesium sulfate, and evaporated in vacuo. The residue was chromatographed on deactivated silica gel with 15% water (150 g), eluting with a mixture of benzene and acetone (50:1 to 8:1). Crystallization from a mixture of dichloromethane and diethyl ether gave 4-nitrobenzyl (5R,6R)-6-[1-methyl-1-(4-nitrobenzyloxycarbonyloxy)ethyl]-7-oxo-3-(3-pyridylthio)-1-azabicyclo[3.2.0]hept-2-ene-2-carboxylate (0.9747 g). The mother liquor was purified by column chromatography on silica gel, followed by crystallization to give the same product (0.2680 g) as a pale yellow powder. Total yield is 1.2427 g.

mp. 162°–164° C.

IR (CH$_2$Cl$_2$): 1785, 1755, 1710, 1605, 1570, 1525, 1350 cm$^{-1}$.

NMR (CDCl$_3$)δ: 1.50 (s, 3H), 1.80 (s, 3H), 2.44 (dd, 1H, J=11,18 Hz), 3.42 (dd, 1H, J=11,18 Hz), 3.69 (d, 1H, J=6 Hz), 4.20 (m, 1H], 5.25 (s, 2H), 5.45 (ABq, 2H, J=14 Hz), 7.2–7.4 (m, 1H), 7.5–7.9 (m, 5H), 8.1–8.4 (m, 4H), 8.6–8.8 (m, 2H).

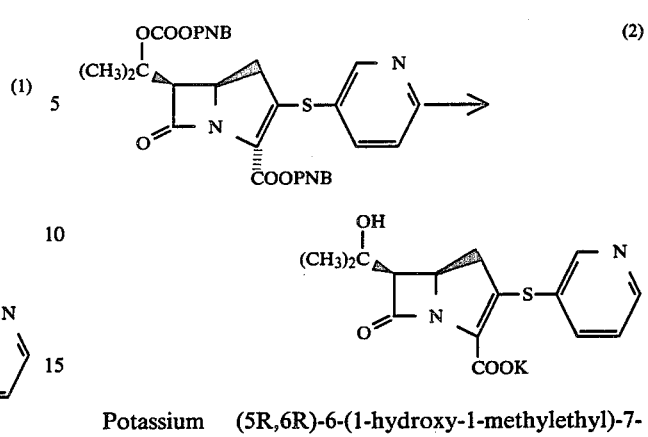

Potassium (5R,6R)-6-(1-hydroxy-1-methylethyl)-7-oxo-3-(3-pyridylthio)-1-azabicyclo[3.2.0]hept-2-ene-2-carboxylate (0.4321 g) was obtained by subjecting 4-nitrobenzyl (5R,6R)-6-[1-methyl-1-(4-nitrobenzyloxycarbonyloxy)ethyl]-7-oxo-3-(3-pyridylthio)-1-azabicyclo[3.2.0]hept-2-ene-2-carboxylate (1.1579 g) to catalytic reduction under hydrogen atmosphere (40 psi) in the presence of platinum (IV) oxide monohydrate (0.260 g) according to a similar manner to that of Example 12-(2).

IR (Nujol): 1745 cm$^{-1}$.

NMR (D$_2$O)δ: 1.18 (s, 3H), 1.42 (s, 3H), 2.47 (dd, 1H, J=10,17 Hz), 3.55 (dd, 1H, J=9,17 Hz), 3.71 (d, 1H, J=6 Hz), 4.20 (ddd, 1H, J=10,9,6 Hz), 7.5–7.7 (m, 1H), 8.0–8.2 (m, 1H), 8.5–8.9 (m, 2H).

UV (H$_2$O) λmax: 301.5 nm (ε=10970).

EXAMPLE 16

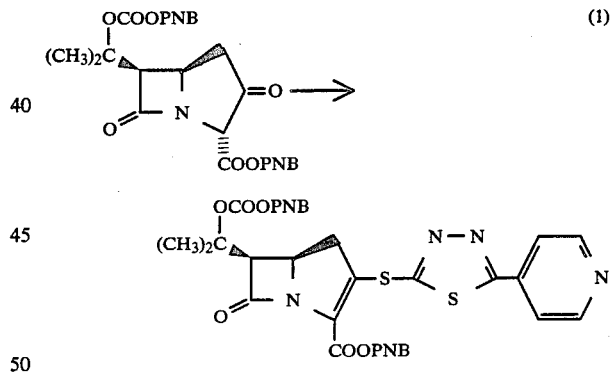

4-Nitrobenzyl (5R,6R)-6-[1-methyl-1-(4-nitrobenzyloxycarbonyloxy)ethyl]-7-oxo-3-[5-(4-pyridyl)-1,3,4-thiadiazol-2-ylthio]-1-azabicyclo[3.2.0]hept-2-ene-2-carboxylate (1.53 g) was obtained by reacting 4-nitrobenzyl (2R,5R,6R)-3,7-dioxo-6-[1-methyl-1-(4-nitrobenzyloxycarbonyloxy)ethyl]-1-azabicyclo[3.2.0]heptane-2-carboxylate (1.50 g) with trifluoromethanesulfonic anhydride (0.489 ml) and then 5-(4-pyridyl)-1,3,4-thiadiazole-2-thiol (919 mg) according to a similar manner to that of Example 12-(1).

IR (CH$_2$Cl$_2$): 1780, 1750, 1700, 1520, 1350 cm$^{-1}$.

NMR (CDCl$_3$) δ: 1.59 (s, 3H), 1.82 (s, 3H), 3.16 (dd, 1H, J=12,19 Hz), 3.74 (d, 1H, J=6 Hz), 4.01 (dd, 1H, J=8,19 Hz), 4.36 (m, 1H), 5.18 (ABq, 2H, J=15 Hz), 5.42 (ABq, 2H, J=14 Hz), 7.54 (d, 2H, J=9 Hz), 7.65 (d, 2H, J=9 Hz), 7.77 (d, 2H, J=6 Hz), 8.23 (d, 4H, J=9 Hz), 8.80 (d, 2H, J=6 Hz).

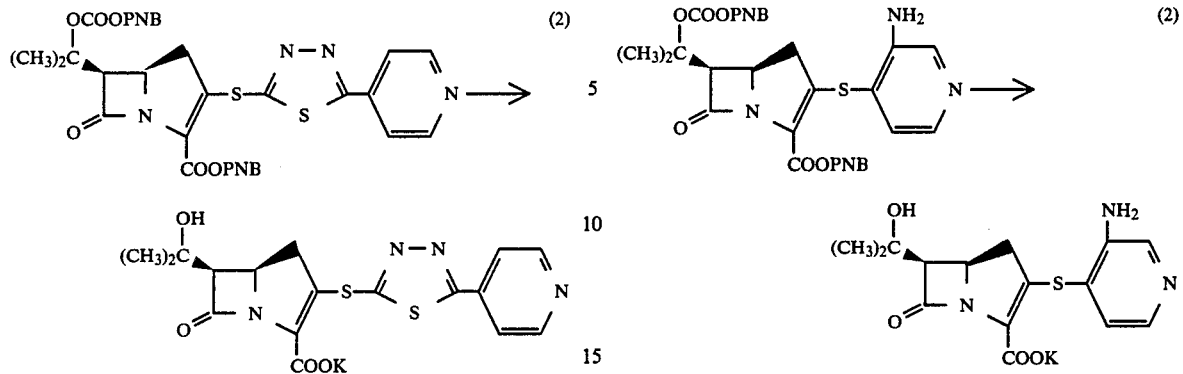

Potassium (5R,6R)-6-(1-hydroxy-1-methylethyl)-7-oxo-3-[5-(4-pyridyl)-1,3,4-thiadiazol-2-ylthio]-1-azabicyclo[3.2.0]hept-2-ene-2-carboxylate (20 mg) was obtained by subjecting 4-nitrobenzyl (5R,6R)-6-[1-methyl-1-(4-nitrobenzyloxycarbonyloxy)ethyl]-7-oxo-3-[5-(4-pyridyl)-1,3,4-thiadiazol-2-ylthio]-1-azabicyclo-[3.2.0]hept-2-ene-2-carboxylate (50 mg) to catalytic reduction under hydrogen atmosphere in the presence of platinum (IV) oxide monohydrate (50 mg) according to a similar manner to that of Example 12-(2).

IR (Nujol): 1750 cm$^{-1}$.

NMR (D$_2$O) δ: 1.25 (s, 3H), 1.47 (s, 3H), 2.87 (dd, 1H, J=10,17 Hz), 3.78 (d, 1H, J=6 Hz), 3.87 (dd, 1H, J=10,17 Hz), 4.37 (m, 1H), 7.77 (dd, 2H, J=1,7 Hz), 8.68 (dd, 2H, J=1,7 Hz).

UV (H$_2$O) λmax: 283 nm (ε=1.38×10$^4$).

EXAMPLE 17

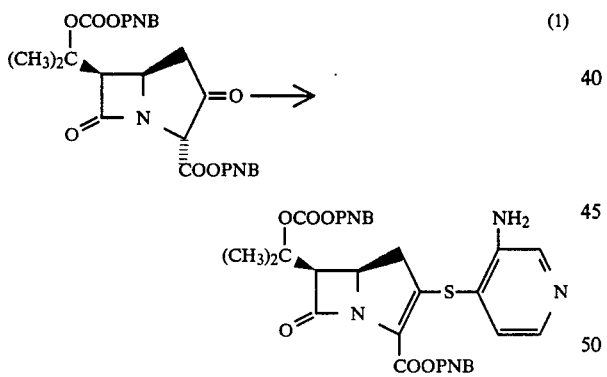

4-Nitrobenzyl (5R,6R)-6-[1-methyl-1-(4-nitrobenzyloxycarbonyloxy)ethyl]-7-oxo-3-(3-aminopyridin-4-ylthio)-1-azabicyclo[3.2.0]hept-2-ene-2-carboxylate (0.904 g) was obtained by reacting 4-nitrobenzyl (2R,5R,6R)-3,7-dioxo-6-[1-methyl-1-(4-nitrobenzyloxycarbonyloxy)ethyl]-1-azabicyclo[3.2.0]heptane-2-carboxylate (0.800 g) with trifluoromethanesulfonic anhydride (0.261 ml) and then 3-amino-4-mercaptopyridine (0.280 g) according to a similar manner to that of Example 12-(1).

IR (CH$_2$Cl$_2$): 1785, 1750, 1610, 1530, 1350 cm$^{-1}$.

NMR (CDCl$_3$) δ: 1.52 (s, 3H), 1.75 (s, 3H), 2.50 (dd, 1H, J=11,18 Hz), 3.43 (dd, 1H, J=9,18 Hz), 3.74 (d, 1H, J=6 Hz), 4.0–4.5 (m, 3H), 5.19 (s, 2H), 5.43 (ABq, 2H, J=14 Hz), 7.0–8.3 (m, 1H).

Potassium (5R,6R)-6-(1-hydroxy-1-methylethyl)-7-oxo-3-(3-aminopyridin-4-ylthio)-1-azabicyclo[3.2.0]hept-2-ene-2-carboxylate (0.245 g) was obtained by subjecting 4-nitrobenzyl (5R,6R)-6-[1-methyl-1-(4-nitrobenzyloxycarbonyloxy)ethyl]-7-oxo-3-(3-aminopyridin-4-ylthio)-1-azabicyclo[3.2.0]hept-2-ene-2-carboxylate (0.900 g) to catalytic reduction under hydrogen atmosphere in the presence of platinum (IV) oxide monohydrate (0.250 g) according to a similar manner to that of Example 12-(2).

IR (Nujol): 1745 cm$^{-1}$.

NMR (D$_2$O) δ: 1.18 (s, 3H), 1.41 (s, 3H), 2.45 (dd, 1H, J=10,18 Hz), 3.53 (dd, 1H, J=8,18 Hz), 3.68 (d, 1H, J=6 Hz), 4.22 (dt, 1H, J=6,15 Hz), 7.40 (br, 1H), 7.90 (br, 2H).

UV (H$_2$O) λmax: 303.0 nm (ε=9700).

EXAMPLE 18

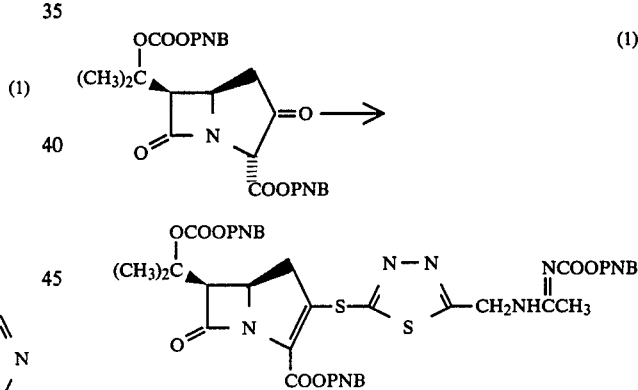

4-Nitrobenzyl (5R,6R)-6-[1-methyl-1-(4-nitrobenzyloxycarbonyloxy)ethyl]-7-oxo-3-[5-[N-{N-(4-nitrobenzyloxycarbonyl)acetimidoyl}aminomethyl]-1,3,4-thiadiazol-2-ylthio]-1-azabicyclo[3.2.0]hept-2-ene-2-carboxylate (914 mg) was obtained by reacting 4-nitrobenzyl 2R,5R,6R)-3,7-dioxo-6-[1-methyl-1-(4-nitrobenzyloxycarbonyloxy)ethyl]-1-azabicyclo[3.2.0]heptane-2-carboxylate (750 mg) with trifluoromethanesulfonic anhydride (0.245 ml) and then 5-[N-{N-(4-nitrobenzyloxycarbonyl)acetimidoyl}aminomethyl]-1,3,4-thiadiazole-2-thiol (496 mg) according to a similar manner to that of Example 12-(1).

IR (CH$_2$Cl$_2$): 1780, 1750, 1690, 1605, 1525, 1350 cm$^{-1}$.

NMR (CDCl$_3$) δ: 1.59 (s, 3H), 1.82 (s, 3H), 2.32 (s, 3H), 3.06 (dd, 1H, J=9,19 Hz), 3.77 (d, 1H, J=5 Hz), 3.80 (dd, 1H, J=10,19 Hz), 4.37 (m, 1H), 5.00 (d, 2H, J=6 Hz), 5.27 (ABq, 2H, J=14 Hz), 5.33 (s, 2H), 5.49

(ABq, 2H, J=13 Hz), 6.32 (t, 1H, J=6 Hz), 7.5–7.8 (m, 6H), 8.1–8.5 (m, 6H).

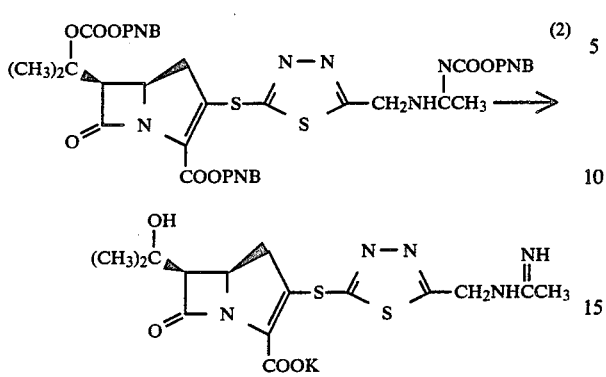

Potassium (5R,6R)-6-(1-hydroxy-1-methylethyl)-7-oxo-3-(5-acetimidoylaminomethyl-1,3,4-thiadiazol-2-ylthio)-1-azabicyclo[3.2.0]hept-2-ene-2-carboxylate (13 mg) was obtained by subjecting 4-nitrobenzyl (5R,6R)-6-[1-methyl-1-(4-nitrobenzyloxycarbonyloxy)ethyl]-7-oxo-3-[5-[N-{N-(4-nitrobenzyloxycarbonyl)acetimidoyl}aminomethyl]-1,3,4-thiadiazol-2-ylthio]-1-azabicyclo[3.2.0]hept-2-ene-2-carboxylate (50 mg) to catalytic reduction under hydrogen atmosphere in the presence of platinum(IV) oxide monohydrate (50 mg) according to a similar manner to that of Example 12-(2).

IR (Nujol): 1750, 1590 cm$^{-1}$.

NMR (D$_2$O) δ: 1.23 (s, 3H), 1.43 (s, 3H), 2.37 (s, 3H), 2.80 (dd, 1H, J=10,18 Hz), 3.74 (dd, 1H, J=9,18 Hz), 3.75 (d, 1H, J=6 Hz), 4.32 (m, 1H), 5.05 (s, 2H).

EXAMPLE 19

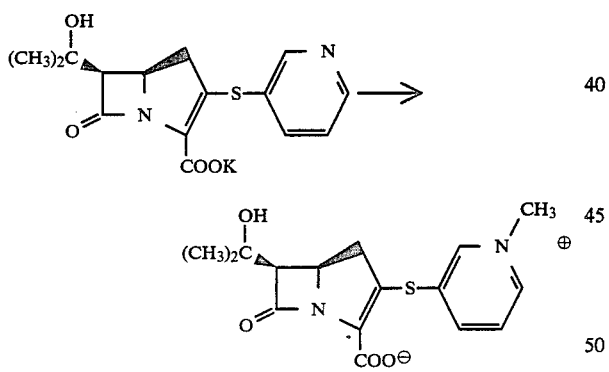

(5R,6R)-6-(1-Hydroxy-1-methylethyl)-3-(1-methyl-3-pyridiniothio)-7-oxo-1-azabicyclo[3.2.0]hept-2-ene-2-carboxylate (0.0278 g) was obtained by reacting potassium (5R,6R)-6-(1-hydroxy-1-methylethyl)-3-(3-pyridylthio)-7-oxo-1-azabicyclo[3.2.0]hept-2-ene-2-carboxylate (0.0400 g) with iodomethane (1.0 ml) in 50% aqueous dioxane (3 ml) according to a similar manner to that of Example 10.

IR (Nujol): 1750 cm$^{-1}$.

NMR (D$_2$O) δ: 1.22 (s, 3H), 1.43 (s, 3H), 2.67 (dd, 1H, J=10,18 Hz), 3.61 (dd, 1H, J=9,18 Hz), 3.74 (d, 1H, J=6 Hz), 4.36 (m, 1H), 4.41 (s, 3H), 8.01 (dd, 1H, J=6,8 Hz), 8.58 (d, 1H, J=8 Hz), 8.70 (d, 1H, J=6 Hz), 8.94 (s, 1H).

UV (H$_2$O) λmax: 273.0 nm (ε=8000), 298.5 nm (ε=7800).

EXAMPLE 20

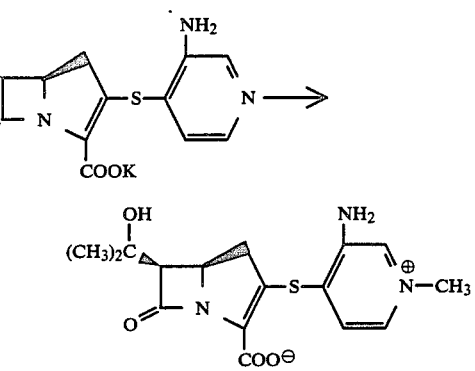

(5R,6R)-6-(1-Hydroxy-1-methylethyl)-3-(3-amino-1-methyl-4-pyridiniothio)-7-oxo-1-azabicyclo[3.2.0]hept-2-ene-2-carboxylate (0.0869 g) was obtained by reacting potassium (5R,6R)-6-(1-hydroxy-1-methylethyl)-3-(3-amino-4-pyridylthio)-7-oxo-1-azabicyclo[3.2.0]hept-2-ene-2-carboxylate (0.1095 g) with iodomethane (10.95 ml) in the presence of N,N-diisopropyl-N-ethylamine (0.051 ml) in 50% aqueous dioxane (44 ml) according to a similar manner to that of Example 10.

IR (Nujol): 1760 cm$^{-1}$.

NMR (D$_2$O) δ: 1.24 (s, 3H), 1.45 (s, 3H), 2.72 (dd, 1H, J=11,18 Hz), 3.66 (dd, 1H, J=8,18 Hz), 3.77 (d, 1H, J=6 Hz), 4.22 (s, 3H), 4.44 (m, 1H), 7.69 (d, 1H, J=6 Hz), 7.92 (d, 1H, J=6 Hz), 8.06 (s, 1H).

UV (H$_2$O) λmax: 220.0 nm (ε=14000), 243.0 nm (ε=11000), 287.0 nm (ε=7100).

EXAMPLE 21

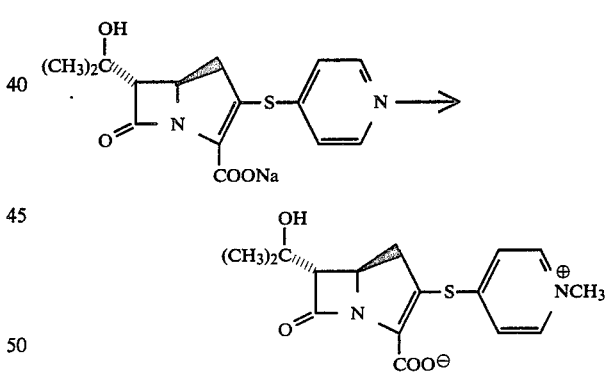

(5R,6S)-6-(1-Hydroxy-1-methylethyl)-3-(1-methyl-4-pyridiniothio)-7-oxo-1-azabicyclo[3.2.0]hept-2-ene-2-carboxylate (26 mg) was obtained by reacting sodium (5R,6S)-6-(1-hydroxy-1-methylethyl)-7-oxo-3-(4-pyridylthio)-1-azabicyclo[3.2.0]hept-2-ene-2-carboxylate (35 mg) with iodomethane (0.4 ml) according to a similar manner to that of Example 10.

NMR (D$_2$O) δ: 1.32 (s, 3H), 1.40 (s, 3H), 3.12 (d, 2H, J=9 Hz), 3.63 (d, 1H, J=3.5 Hz), 4.25 (s, 3H), 4.42 (dt, 1H, J=3.5,9 Hz), 7.78 (d, 2H, J=7 Hz), 8.45 (d, 2H, J=7 Hz).

EXAMPLE 22

A sterile mixture of sodium (5R,6S)-3-(4-pyridylthio)-6-(1-hydroxy-1-methylethyl)-7-oxo-1-azabicyclo[3.2.0-]hept-2-ene-2-carboxylate (125 mg) and sodium salt of Ceftizoxime or sodium salt of Cefazolin (125 mg) was put in a sterile vial and the vial was sealed. And when used, the above mixture was dissolved in a sterile water (2 ml) to give an injection preparation.

What we claim is:

1. A compound of the formula

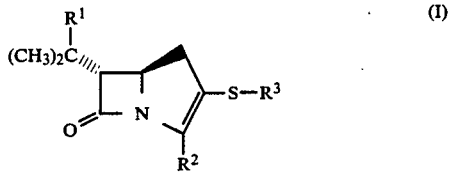

in which $R^1$ is hydroxy, a protected hydroxy or lower alkoxy group, $R^2$ is carboxy or an easily eliminable esterified carboxy and $R^3$ is pyridyl and pharmaceutically acceptable salts thereof.

2. A compound of claim 1, wherein $R^1$ is hydroxy and $R^2$ is carboxy.

3. A pharmaceutical antimicrobial and β-lactamase inhibiting composition which comprises an effective amount of the compound claimed in claim 1 in admixture with pharmaceutically acceptable carriers.

4. A compound of claim 2, which is sodium (5R,6S)-3-(4-pyridylthio)-6-(1-hydroxy-1-methylethyl)-7-oxo-1 azabicyclo[3.2.0]hept-2-ene-2-carboxylate.

* * * * *